(12) United States Patent
Janowski et al.

(10) Patent No.: US 8,540,769 B2
(45) Date of Patent: Sep. 24, 2013

(54) DEVICE FOR SECURING AN IMPLANT TO TISSUE

(75) Inventors: Brian P. Janowski, Marquette, MI (US); John P. Sullivan, Marquette, MI (US)

(73) Assignee: Pioneer Surgical Technology, Inc., Marquette, MI (US)

( * ) Notice: Subject to any disclaimer, the term of this patent is extended or adjusted under 35 U.S.C. 154(b) by 32 days.

(21) Appl. No.: 13/035,732

(22) Filed: Feb. 25, 2011

(65) Prior Publication Data

US 2011/0208311 A1  Aug. 25, 2011

Related U.S. Application Data

(63) Continuation-in-part of application No. 12/324,292, filed on Nov. 26, 2008, now abandoned.

(60) Provisional application No. 60/990,809, filed on Nov. 28, 2007.

(51) Int. Cl.
*A61F 2/44* (2006.01)

(52) U.S. Cl.
USPC ................................ 623/17.11; 623/17.16

(58) Field of Classification Search
USPC ....................................................... 623/17.11
See application file for complete search history.

(56) References Cited

U.S. PATENT DOCUMENTS

| 6,558,424 B2 * | 5/2003 | Thalgott | 623/17.16 |
| 6,770,096 B2 * | 8/2004 | Bolger et al. | 623/17.16 |

\* cited by examiner

*Primary Examiner* — Bruce E Snow
*Assistant Examiner* — Brian Dukert
(74) *Attorney, Agent, or Firm* — Fitch, Even, Tabin & Flannery LLP

(57) ABSTRACT

An implant device is provided for implantation within an intervertebral space between adjacent vertebrae comprising an implant body, a rotatable portion and a piercing portion configured to pierce the adjacent vertebra.

7 Claims, 65 Drawing Sheets

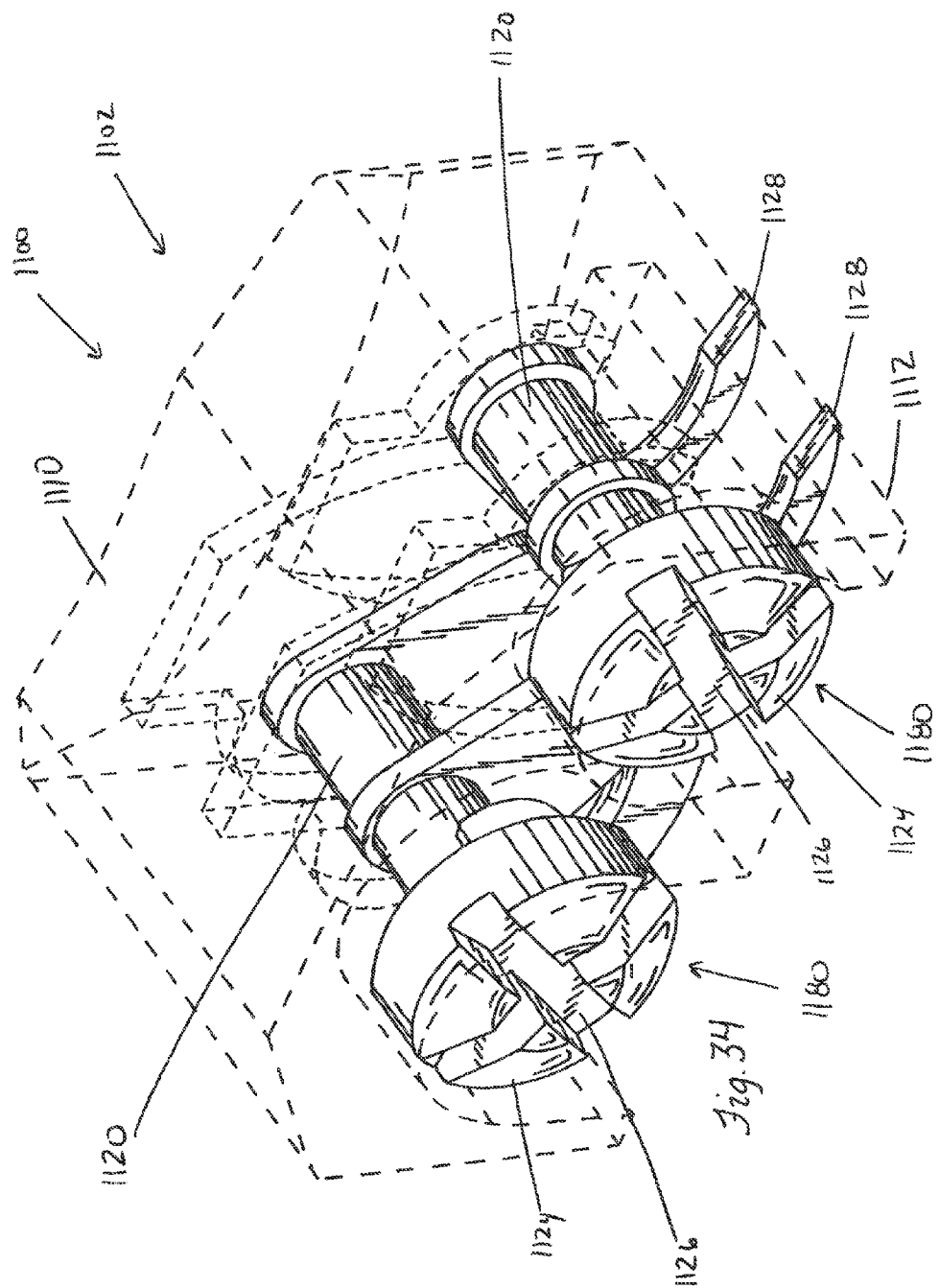

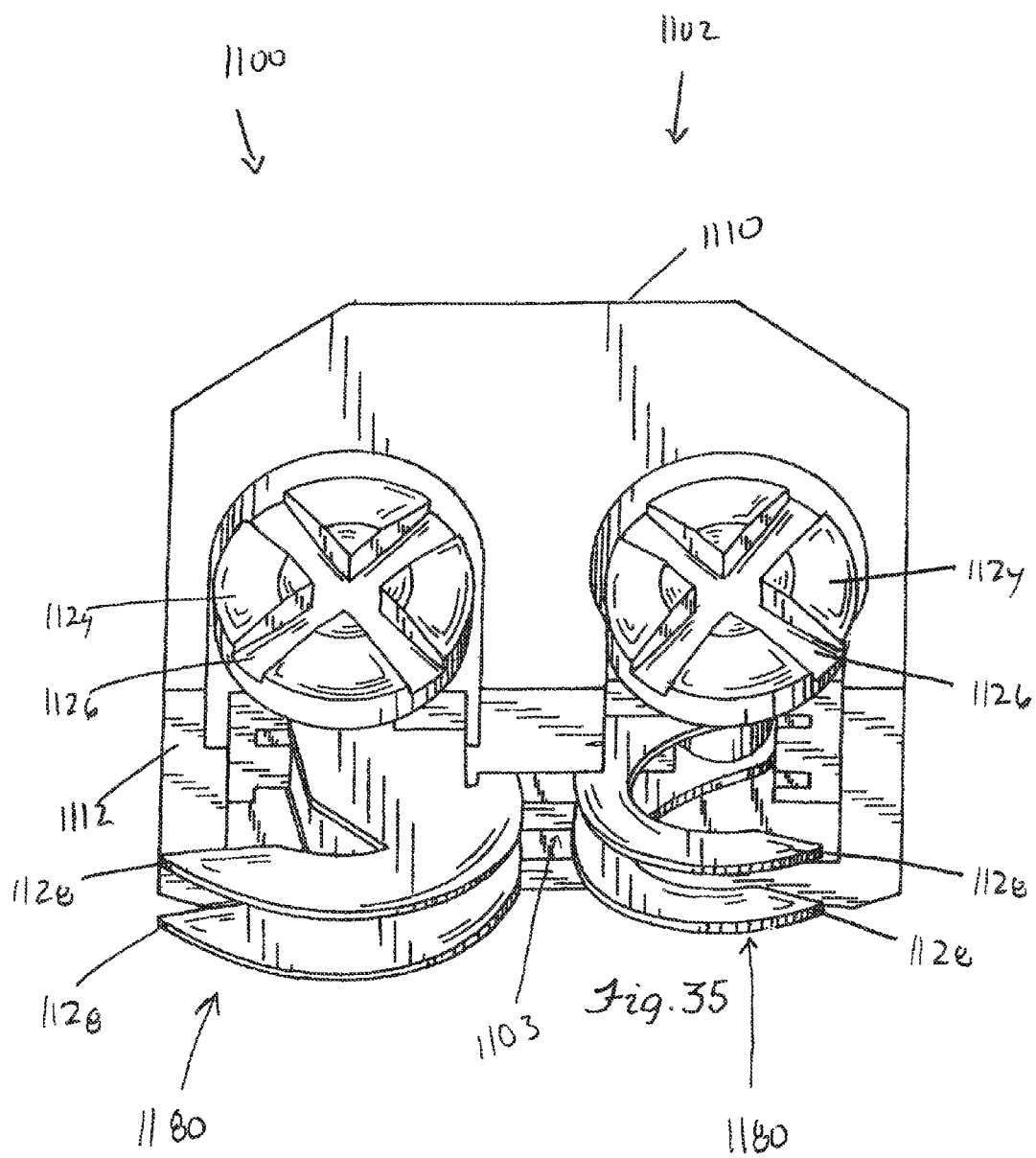

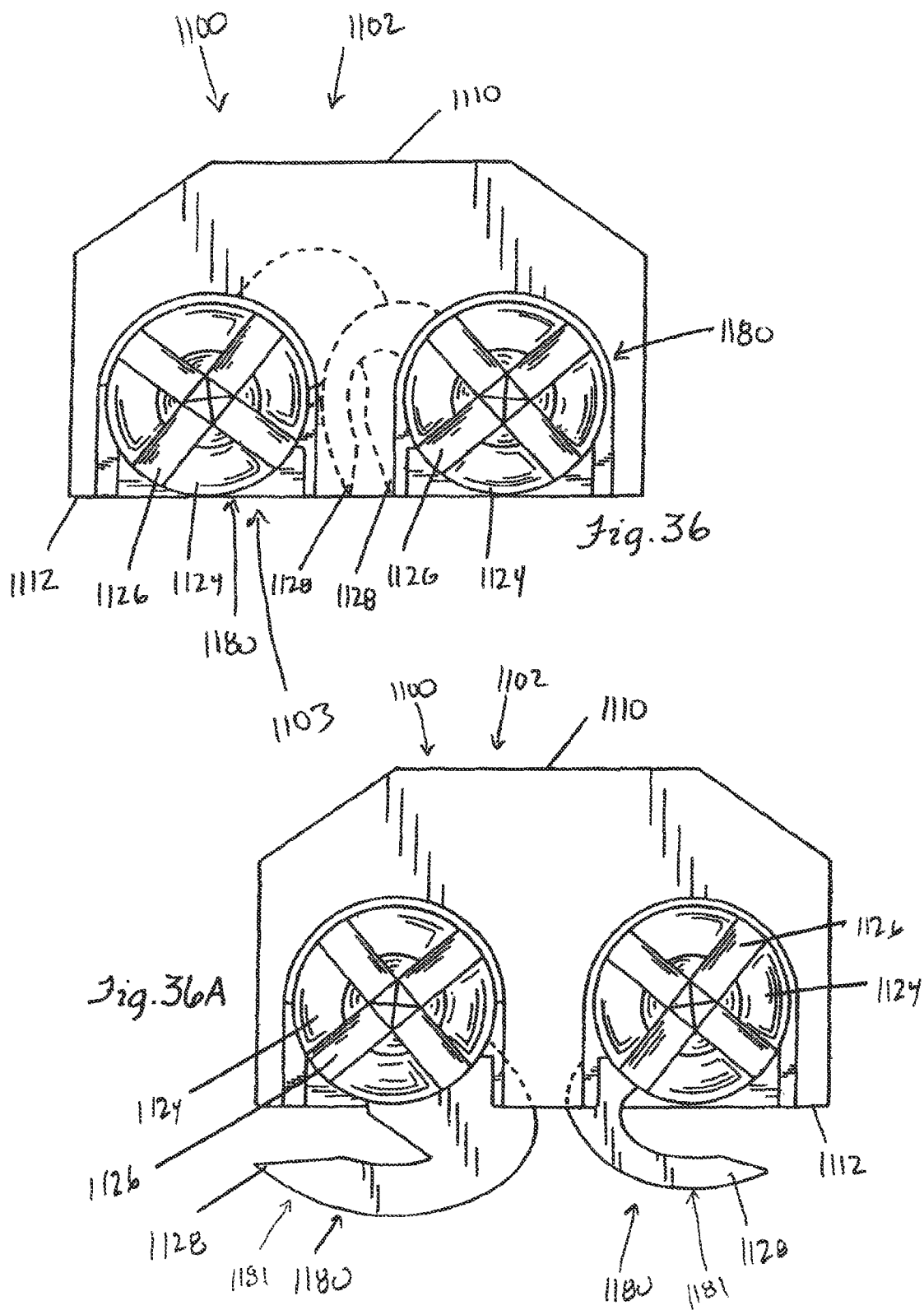

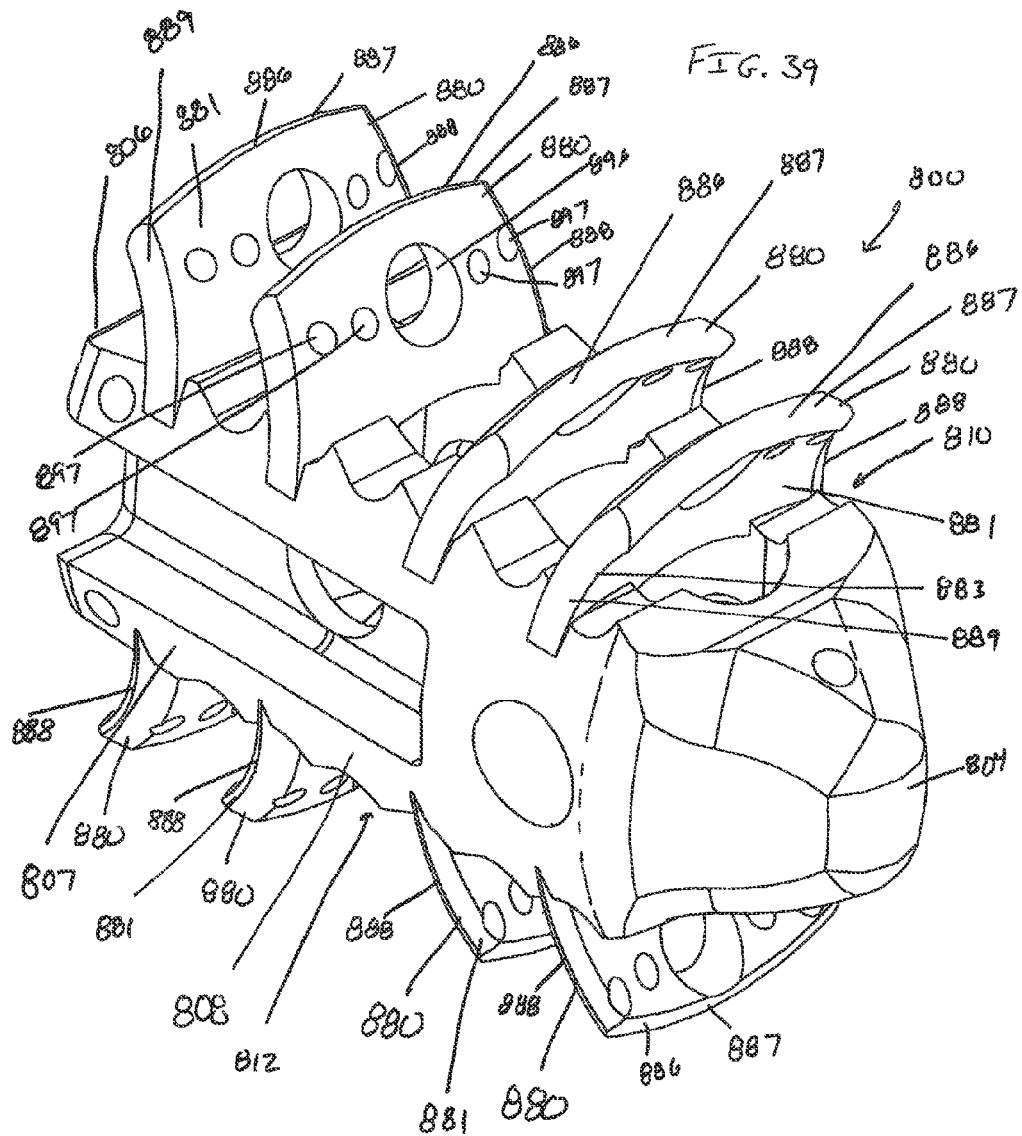

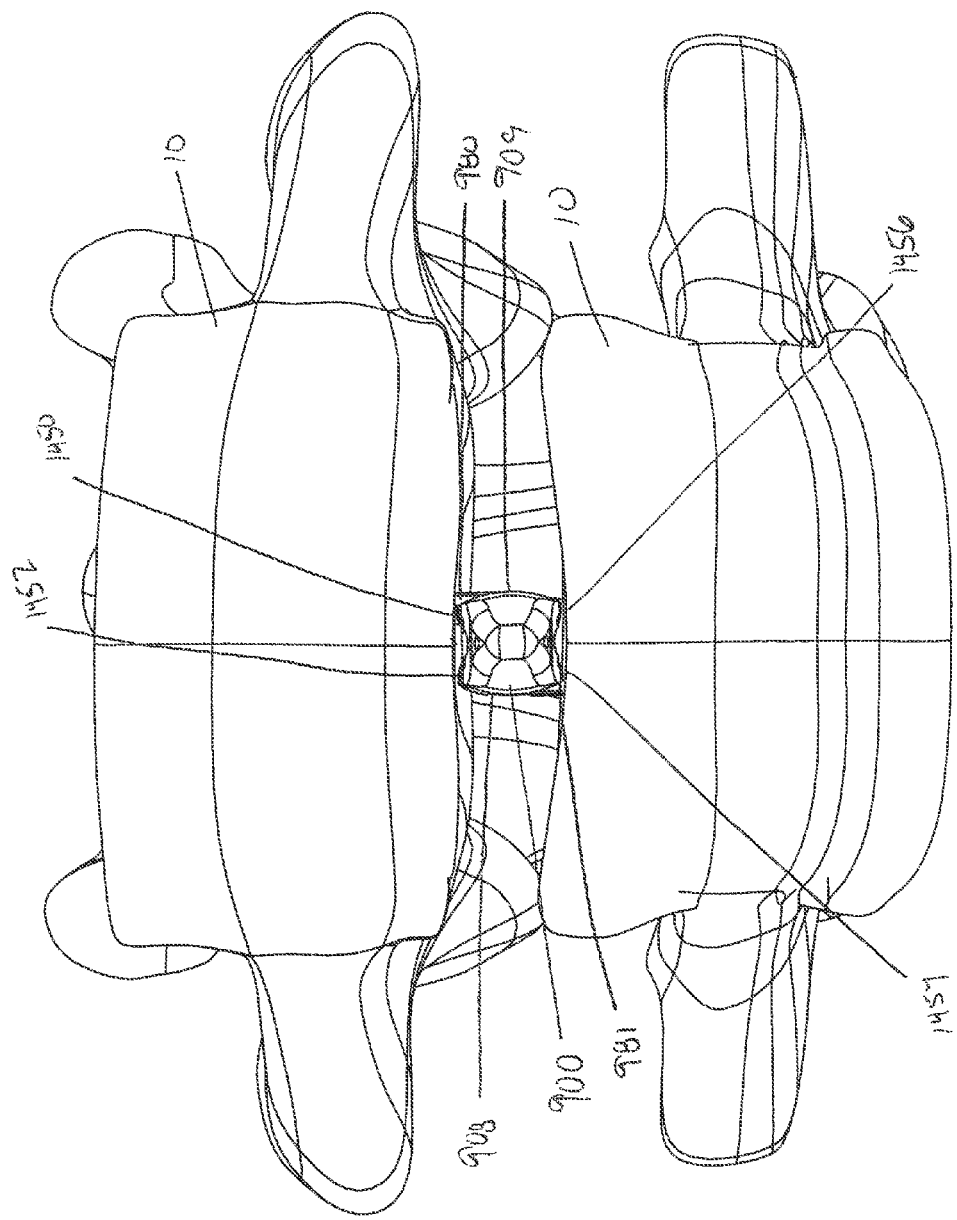

DEVICE FOR SECURING AN IMPLANT TO TISSUE

CROSS REFERENCE TO RELATED APPLICATIONS

This application is a continuation-in-part of U.S. patent application Ser. No. 12/324,292, filed Nov. 26, 2008, which, claims the benefit of the filing date of U.S. Provisional Application 60/990,809, filed Nov. 28, 2007, both of which are hereby incorporated by reference in their entirety herein.

FIELD OF THE INVENTION

The invention relates to implant devices for implantation within an intervertebral space and fixation to the adjacent vertebrae.

BACKGROUND OF THE INVENTION

The spine is the central support column for the human body. It includes a series of vertebrae and intervertebral discs between adjacent vertebrae. The vertebrae are formed of hard bone while the intervertebral discs comprise a comparatively soft annulus and nucleus. The intervertebral discs help to absorb pressure, distribute stress, and keep adjacent vertebrae from grinding against each other.

A variety of spinal conditions including, for example, trauma, deformity, disease, or other degenerative conditions, may result in a person experiencing pain or limited physical mobility. This pain and reduced mobility is often attributed to the rupture or degeneration of the intervertebral discs resulting in compression of spinal nerve roots.

One manner of treating these conditions is through immobilization and fusion of the injured portion of the spine. In spinal fusion surgery, two or more adjacent vertebrae are initially immobilized relative to each other and, over time, become fused in a desired spatial relationship. Often, these procedures require correcting the spacing between adjacent vertebrae by implanting an intervertebral implant.

One problem with existing intervertebral implants is that, once inserted, the implants are explanted from between adjacent vertebrae. To promote immobilization and fusion of adjacent vertebrae, the intervertebral implant should be designed to provide a substantially flush interface with the endplates of the adjacent vertebrae. However, studies have shown that the vertebral endplates of the lumbar spine have varying degrees of concavity. More specifically, the superior endplates show a tendency to be less concave than the inferior endplates. Accordingly, there is a need for implants that resist explantation from between the adjacent vertebrae and provide for flush engagement with the inferior and superior endplates.

The present invention may be used to fulfill these, as well as other needs and objectives, as will be apparent from the following description of embodiments of the present invention.

SUMMARY OF THE INVENTION

Thus, in accordance with one aspect of the invention, an implant device is provided for implantation between adjacent vertebrae. The implant device comprises an implant body, a plurality of gripping portions, a rotatable portion and a piercing portion. The implant body includes a leading edge and a trailing edge. The gripping portions extend from the implant body and are configured to engage at least one of the adjacent vertebrae. The rotatable portion of the implant body extends from the leading edge to the trailing edge and defines an axis. The rotatable portion is further configured to be rotatable about the axis when the implant device is positioned between adjacent vertebrae. The piercing portion of the implant device extends from the implant body and is configured to rotate about the axis and rotatably pierce an adjacent vertebra.

According to another aspect of the invention, an implant device is provided for implantation within an intervertebral device between adjacent vertebrae, which comprises an implant body, a plurality of gripping portions, and a piercing portion. The implant body includes a leading edge and a trailing edge and defines a longitudinal axis therebetween. The gripping portions extend from the implant body and are configured to grip at least one of the adjacent vertebrae. The piercing portion is integral with the implant body and extends generally normal to the longitudinal axis. Further, the implant body is configured to rotate between adjacent vertebrae so that the piercing portion rotatably pierces one of the adjacent vertebrae.

In another aspect of the invention, a spinal implant is provided for being secured to adjacent vertebrae. The spinal implant includes an implant body having teeth to frictionally engage the adjacent vertebrae. The spinal implant further includes a pair of elongate scissor arms.

The scissor arms include opposite end portions, with each opposite end portion having a bone penetrating end configured for piercing the surface of an adjacent vertebrae. A single pivot member such as a pivot pin pivotably interconnects the pair of scissor arms intermediate the opposite end portions thereof and is connected to the implant body. The pivot pin allows the scissor arms to pivot between a reduced profile insertion orientation, in which the bone penetrating ends of the scissor arms do not extend beyond the teeth, to a securing orientation. As each of the scissor anus are pivoted about the single pivot pin toward the securing orientation, one of the bone penetrating ends of each scissor arm penetrates one of the vertebral bodies and the other bone penetrating end of each scissor arm penetrates the other vertebral body.

In one embodiment, the scissor arms are arranged in the insertion orientation so that one of the opposite end portions of each of the scissor arms are adjacent one another. The adjacent end portions each include a tool engagement portion for being engaged by a tool. In particular, the tool engagement portions allow for the tool to pivot the scissor arms about the single pivot member. The scissor arms are configured so that as they are pivoted both bone penetrating ends of each scissor arm pierce the adjacent vertebral bodies.

In another aspect of the present invention, a spinal implant is provided for being secured to adjacent vertebrae. The spinal implant includes sidewall surfaces for providing low-friction engagement with the vertebral bodies as the implant body is inserted. The implant body is configured to be rotatable between the adjacent vertebral bodies to an implanted orientation. A first set of teeth adjacent one side wall surface and a second set of teeth adjacent the other sidewall surface frictionally engage the vertebral bodies with the implant body rotated to the implanted orientation.

An anchoring member of the spinal implant is fixedly connected to the implant body adjacent the first set of teeth. The anchoring member includes a bone piercing portion extending toward the other sidewall surface. The bone piercing portion is sized, however, to extend beyond the first set of teeth to a position generally between the first and second sets of teeth. As such, as the spinal implant body is rotated between the adjacent vertebrae so that the second set of teeth engages the vertebral body before the first set of teeth, the second set of teeth will also engage the vertebral body before the bone piercing portion of the anchoring member.

In another aspect of the present invention, a method is provided for securing an implant body between adjacent vertebral bodies. The method includes inserting an implant body between adjacent vertebral bodies so that opposite smooth surfaces engage corresponding surfaces of the adjacent vertebral body. Once inserted, the implant body is rotated in the intervertebral space between the adjacent vertebral bodies. During rotation, the teeth of the implant body adjacent the smooth surface engage the surfaces of the vertebral bodies. After the teeth engage the surfaces of the vertebral bodies, the implant body continues to rotate so that anchoring members of the implant body pierce the surfaces of the adjacent vertebral bodies to further secure the implant body to the adjacent vertebral bodies.

BRIEF DESCRIPTION OF THE DRAWINGS

FIG. 34 is a top perspective view of an alternative implant device in accordance with another aspect of the invention showing anchoring members extending out from a recess of an implant body in a securing orientation;

FIG. 35 is a bottom perspective view of the implant device of FIG. 34 showing the anchoring members in the securing orientation;

FIG. 36 is a front view of the implant device of FIG. 34 in the insertion orientation showing anchoring members in phantom FIG. 36A is a front view of the implant device of FIG. 34 in the securing orientation showing a portion of anchoring members in phantom;

FIG. 39 is a perspective view of an implant device in accordance with another aspect of the invention showing teeth on a body of the implant device and cutting fins projecting from the body beyond the teeth;

FIG. 66 is a front end elevational view of the implant device of FIG. 44 showing the implant body in the securing orientation between adjacent vertebral bodies with the teeth engaging the surfaces of the adjacent vertebral bodies and the anchor members having penetrated the adjacent vertebral bodies.

DETAILED DESCRIPTION OF THE PREFERRED EMBODIMENTS

With reference to FIGS. 1-31 and 34-60, implant devices are shown configured in accordance with various aspects of the invention for being implanted within the spine 6 between adjacent vertebral bodies 10 and secured to at least one of those bodies 10. Further contemplated embodiments include artificial discs, annulus plugs, and other implants, such as those described in U.S. Patent Application Publication No. 2006/0129238 to Paltzer, U.S. Patent Application Publication No. 2007/0282441 to Stream et al., and U.S. Patent Application Publication No. 2008/0103598 to Trudeau et al., which are hereby incorporated in their entirety herein.

Figure 1:
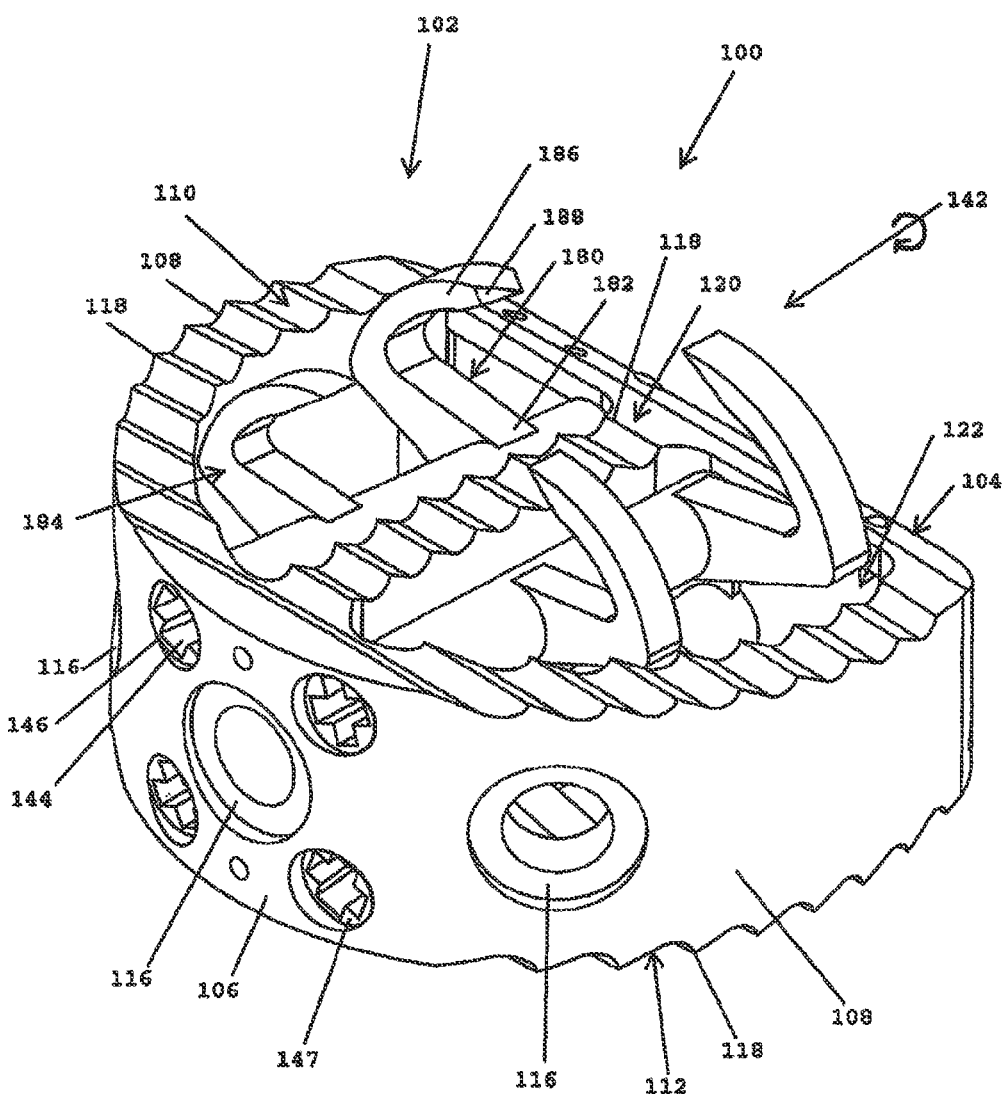
FIG. 1 is a perspective view of an implant device in accordance with one aspect of the invention showing rotatable portions connected to an implant body rotated so that piercing portions extending beyond upper and lower surfaces of the implant body in the securing orientation.
Figure 2:
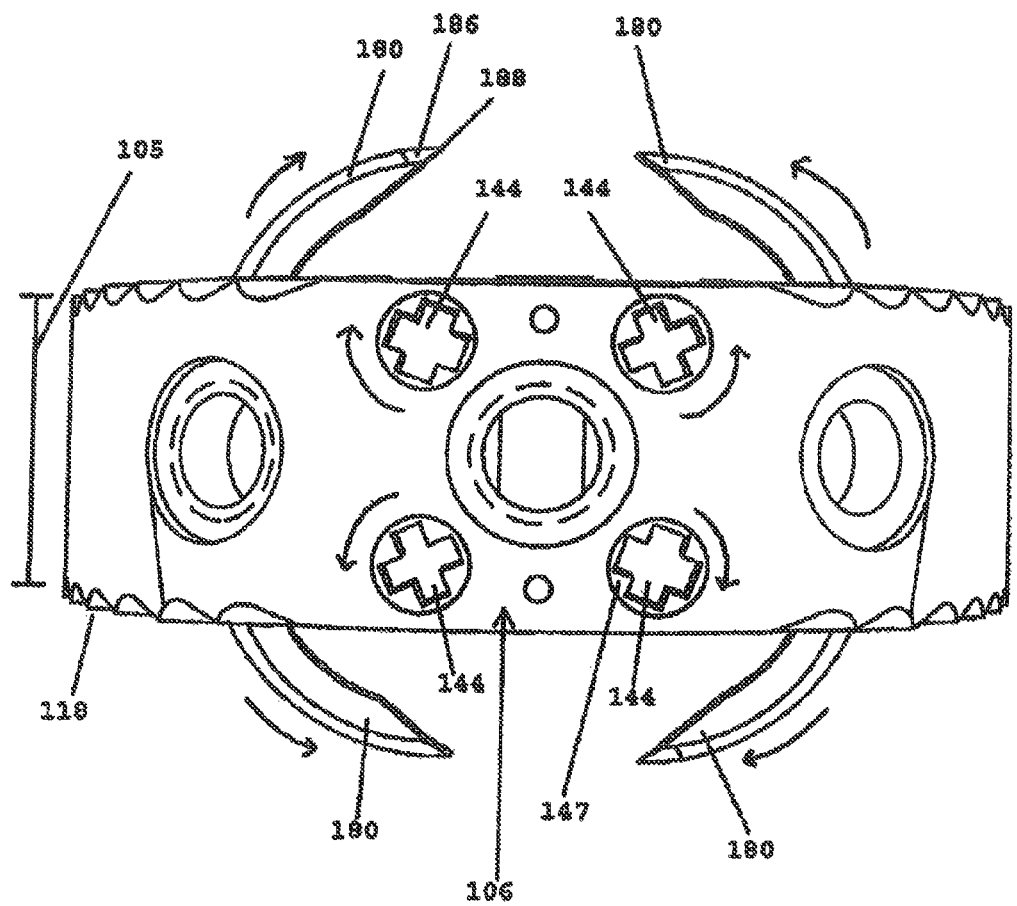
FIG. 2 is an end view of the trailing edge of the implant device of FIG. 1 showing the piercing portions in the securing orientation.
Figure 3:
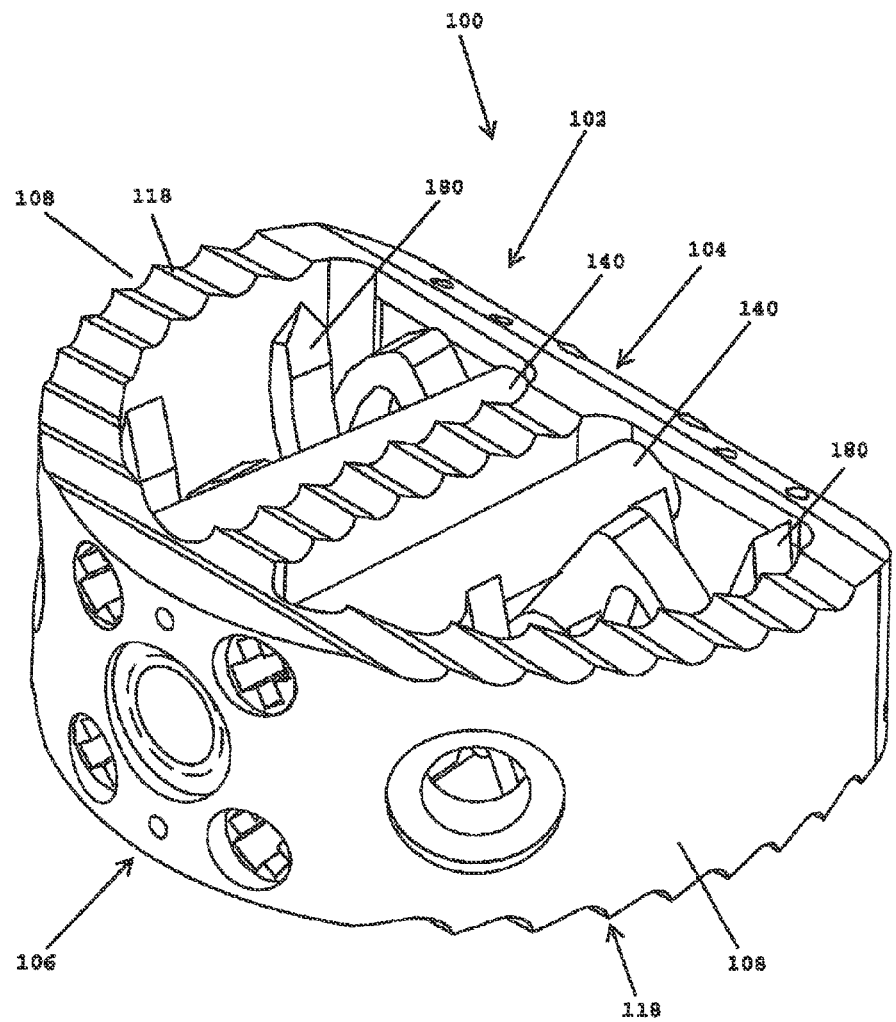
FIG. 3 is a perspective view of the implant device of FIG. 1 with the piercing portions rotated into the central cavity in an insertion orientation.

With reference to FIGS. 1-8, the implant device 100 is shown in accordance with one aspect of the invention. The implant device 100 includes an implant body 102, a rotatable portion 140 and a piercing portion 180 extending from the rotatable portion 140. The rotatable portion 140 and piercing portion 180 can be arranged in a compact orientation, as shown in FIG. 3, an extended orientation, as shown in FIG. 1, or an intermediate orientation. The rotatable portion 140 and piercing portion 180 are configured to provide adequate structural strength to the implant device 100 so that adequate torque can be applied so the piercing portion 180 can penetrate the adjacent vertebral body 10.

The rotatable portion 140 extends from the leading edge 104 of the implant body 102 to the trailing edge 106 of the implant body 102 and defines a longitudinal axis 142. In one embodiment, the rotatable portion 140 extends parallel to one of the upper and lower surfaces 110, 112 of the implant body 102. In an alternative embodiment, the rotatable portion 140 extends across the implant body 102 in a direction which is not parallel to either the upper or lower surfaces 110, 112. As shown in FIGS. 1-8, the rotatable portion 140 preferably extends through a throughbore 146 in the trailing edge 106 and a throughbore 148 in the leading edge 104. The throughbores 146 and 148 are preferably located generally centrally between the lateral edges 108 of the implant body 102, as shown in FIG. 2. Further, the throughbores 146, 148 can be located along the height 105 of the implant body 102. In one embodiment, as shown in FIGS. 1-4, the throughbores 146, 148 are adjacent either the upper surface 110 or lower surface 112 of the implant body 102.

The rotatable portion 140 and the throughbores 146 and 148 are configured to permit rotation of the rotatable portion 140 within the throughbores 146 and 148. Preferably, the throughbores 146 and 148 include a smooth annular surface, as shown in FIGS. 2, 3, and the rotatable portion 140 includes corresponding annular surfaces at either end. In the illustrated embodiment, the rotatable portion 140 includes a tubular shaft which includes an annular surface along its entire length. Other configurations, such as the use of a bearing or bushing between the rotatable portion 140 and throughbores 146 and 148, are contemplated to ease and enable rotation of the rotatable portion 140.

Preferably, the trailing end 147 of the rotatable portion or shaft 140 includes a tool engagement portion 144. The tool engagement portion 144 is configured to be engaged by a tool apparatus 1000 to rotate the rotatable portion 140 and the piercing portion 180 extending therefrom about the longitudinal axis 142. The rotatable portion 140 and tool engagement portion 144 are configured to deliver sufficient torque to the piercing portion 180 to permit the piercing portion 180 to rotatably penetrate the adjacent vertebral body 10. In one embodiment, as shown in FIGS. 1-4, the tool engagement portion 144 includes an X-shaped aperture in the trailing end 147 of the rotatable portion 140.

The rotatable portion 140 and implant body 102 are further configured to permit the rotatable portion 140 to be positioned within the implant body 102. Various configurations include, for example, a collapsible rotatable portion 140, an expandable implant body 102, and one or both of the rotatable portion 140 and implant body 102 comprising more than one member thereby allowing for disassembly prior to positioning of the rotatable portion 140 within the implant body 102 and reassembly upon positioning of the rotatable portion 140 in the desired location.

Figure 5:
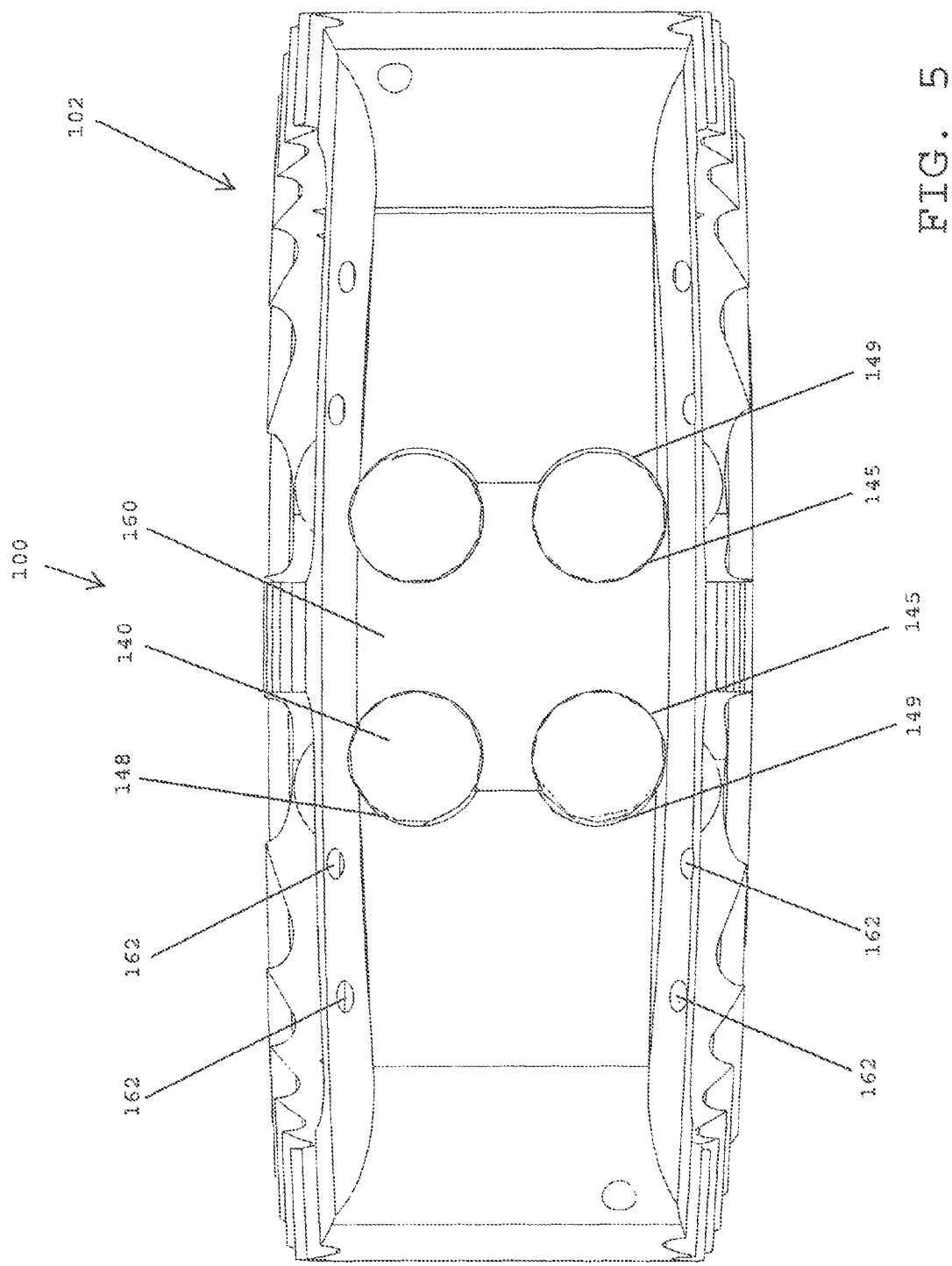
FIG. 5 is an end view of the implant device of FIG. 1 showing a leading edge of the implant body.
Figure 6:
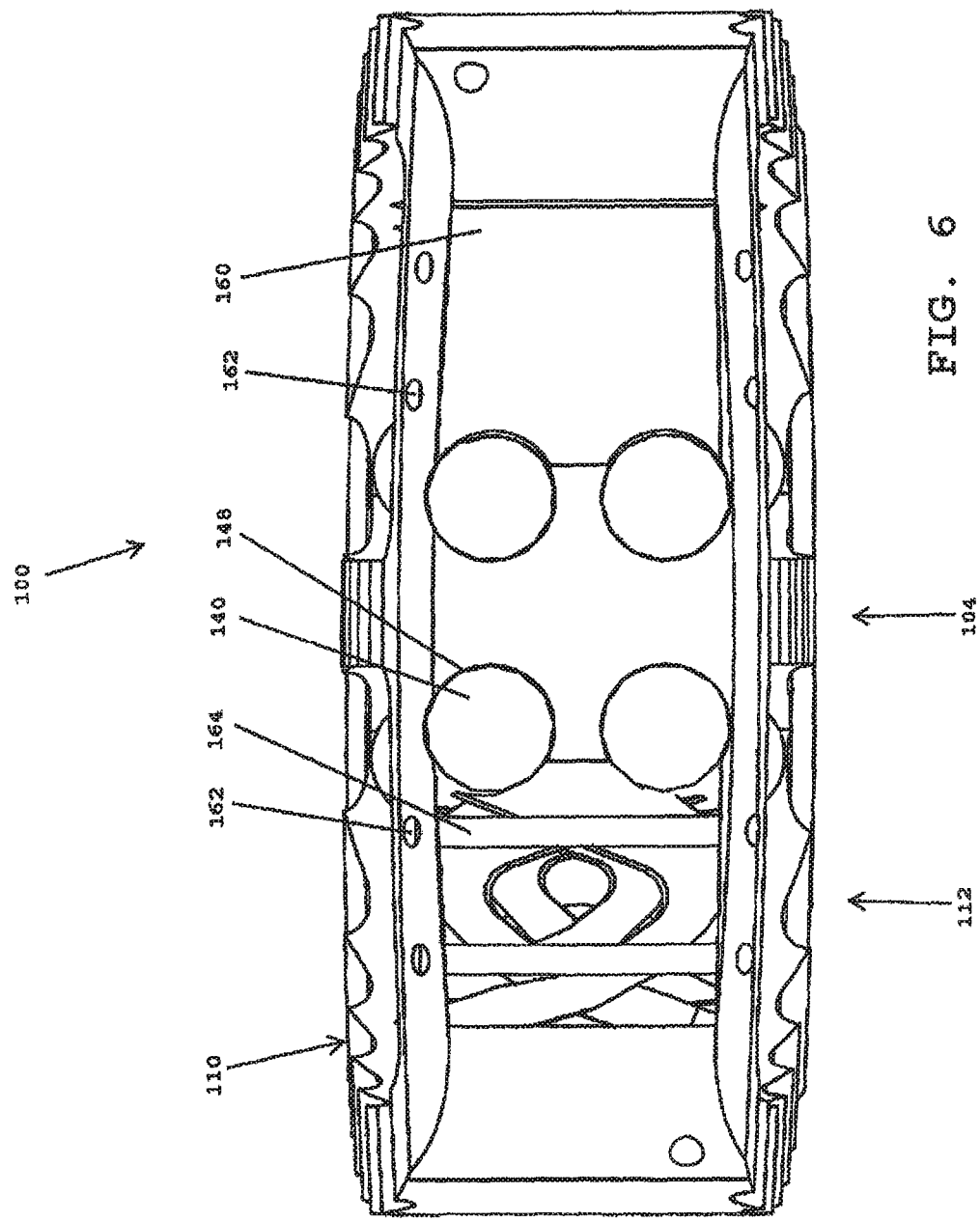
FIG. 6 is an end view of the implant device of FIG. 1 showing the leading edge of the implant body with one of the securing wall portions removed.

As shown in FIGS. 5 and 6, the leading edge 104 of the implant body includes a removable securing wall portion 160. The leading edge 104 and removable securing wall portion 160 define the throughbore 148. Preferably, the throughbore 148 is defined by a penannular portion 145 configured to accept the rotatable portion 140 and a rounded portion 149 configured to secure the rotatable portion 140 in the penannular portion 145. In a preferred embodiment, the leading edge 104 includes the penannular portion 145 to permit the rotatable portion 140 to be positioned within both the throughbore 146 of the trailing edge 106 and the penannular portion 145 of throughbore 148 before the securing wall 160 is secured to the leading edge 104. The removable securing wall portion 160 is configured to be secured onto the leading edge 104 by any known means. Preferably, as shown in FIGS. 5,6, the leading edge 104 includes securing throughbores 162, and the removable securing wall portion 160 includes corresponding securing throughbores 163, the securing throughbores 162, 163 configured to receive a securing member 164, such as a pin, therein, to secure the removable securing wall portion 160 to the leading edge 104.

More particularly, the implant body 102 includes two removable wall portions 160 to allow an end of the rotatable portions 140 to be removably captured within the throughbore 148 of the trailing edge 106 of the implant body 102. The other end of the rotatable portions 140 can then be received in a rounded pennannular portion 145 of the leading edge 104. A removable wall portion 160 the can then be secured to the leading edge 104 of the implant body 102. As shown in FIGS. 5 and 6, the removable wall portion 160 includes a rounded edge 149 configured to cooperate with the rounded portion 145 of the leading edge 104 to provide a rounded opening 148 for the end of the shaft or rotatable portion 140.

The piercing portion 180 includes a proximal base portion 182, which extends from the rotatable portion 140, and a distal end portion 186. In one embodiment, the proximal portion 182 is integral with the rotatable portion 140. In an alternative embodiment, the proximal portion 182 is secured to the rotatable portion 140 by any known means, such as, for example, a screw, an interlocking mechanism of the proximal portion 182 and the rotatable portion 140, or by an adhesive. Preferably, the distal end portion 186 includes a tapered end portion 188 to ease the penetration of the distal end portion 186 of the piercing portion 180 into the vertebral body 10.

In the insertion orientation, the piercing portion 180 is located within a central cavity 122 of the implant body 102, which extends from the upper surface 110 of the implant body 102 to the lower surface 112 of the implant body 102, and from the leading edge 104 to the trailing edge 106. More particularly, in the insertion orientation, as shown in FIGS. 3-7, the piercing portions 180 do not extend beyond gripping members 118 or teeth of the upper and lower surfaces 110 and 112 of the implant body 102, and are confined between the leading edge 104, trailing edge 106 and lateral walls 108 of the implant body 102. The central cavity 122 can extend from one lateral edge 108 to the other lateral edge 108. Referring to FIG. 8, the central cavity 122 extends from one lateral edge 108 to a central support portion 120 in the form of an internal wall. More particularly, the central cavity 122, extending between lateral edges 108, includes a central support portion or internal wall 120 bisecting the central cavity 122. The central support portion or internal wall 120 extends from the leading edge 104 to the trailing edge 106 and is generally intermediate the lateral edges 108. Preferably, the central support portion or internal wall 120 extends from the upper surface 110 of the implant body 102 to the lower surface 112 of the implant body 102 and is configured to engage and support the adjacent vertebral bodies 10.

In the securing orientation, the piercing portion 180 extends away from one of the upper and lower surfaces 110, 112 of the implant body 102. The piercing portion 180 is configured to extend above the upper surface 110 or lower surface 112 a distance sufficient to secure the implant body 102 to the vertebral body 10 without compromising the integrity of the vertebral body 10. More particularly, the piercing portion 180 is configured so that sufficient bone structure remains intact between the tapered end portion 188 and the vertebral surfaces so that the bone structure is not compromised during normal loading or flexion of the spine as described hereinafter.

As the rotating portion 140 and piercing portion 180 are rotated between adjacent vertebral bodies 10, the piercing portion 180 extends, for example, above the upper surface 110, out of the central cavity 122 toward the adjacent vertebral body 10 and, as it does so, penetrates the vertebral body 10. As the piercing portion 180 rotatably penetrates the vertebral body 10, at least one of the implant body 102 and the penetrated vertebral body 10 are urged toward the other until, preferably, the upper surface 110 firmly engages the vertebral body 10. Similarly, as the rotatable portions or shafts 140 are rotated so that piercing portions extend beyond the lower surface 112, the piercing portions 180 penetrate the adjacent vertebral body 10. As the vertebral body is penetrated by the piercing portions 180, at least one of the implant body 102 and the penetrated vertebral body 10 are urged toward the other until the lower surface 112 of the implant body 102 firmly engages the vertebral body.

As shown, the implant device 100 includes one piercing portion 180 extending from one rotatable portion 140. Preferably, the implant device 100 includes at least two piercing portions 180 extending from a rotatable portion 140, the piercing portions 180 preferably extending in parallel from the rotatable portion 140. In a further preferable embodiment, and as shown in FIGS. 1-4, the implant device 100 includes at least two rotatable portions 140, with one or more piercing portions extending from each rotatable portion 140. In another embodiment, the implant device 100 includes two rotatable portions 140 with corresponding piercing portions 180 configured to extend beyond one of the upper and lower surfaces 110, 112 of the implant body 102. In a preferable embodiment, the implant device 100 includes at least two rotatable portions 140 with corresponding piercing portions 180, at least one rotatable portion 140 with corresponding piercing portions 180 configured to extend from each of the upper and lower surfaces 110, 112 of the implant body 102.

As shown in FIGS. 1, 3, 8, the rotatable portions 140 and piercing portions 180 are configured to not interfere with one another in the insertion orientation or the securing orientation. In particular, the piercing portions 140 can be positioned within the central cavity 122 with the piercing portions 180 staggered along the longitudinal axis 142 of the rotatable portions 140 so that all of the piercing portions 180 can be disposed within the central cavity 122 in the insertion orientation, preferably with the piercing portions 180 positioned generally between the upper and lower surfaces 110, 112 of the implant body 102 to assist in insertion of the implant body 102 between adjacent vertebral bodies 10.

The configuration of the piercing portion 180 is dependent on multiple variables and is coordinated with multiple structural features of the implant device including, for example, the width, depth and height of the central cavity 122, the location of the rotatable members 140 and corresponding throughbores 146, 148 within the central cavity 122, and the number of rotatable members 140 and piercing portions 180 of the implant device 100. Additional variables include the shape, length, width and depth of the piercing portions 180 and the direction in which the piercing portions 180 extend. In particular, repositioning the rotatable members 140 and throughbores 146, 148 along the height and width of the central cavity 122 can be used to accommodate varying piercing portion 180 configurations including, for example, differences in shape, length, depth, width, and direction in which the piercing portions 180 extend.

Additionally, the particular shape of the piercing portion 180 can depend on factors such as the density of the bone to he penetrated, the degree of compression required between the device and the bone, the static and dynamic loading on the implant and bone, as well as the strength of the materials used.

Figure 9:
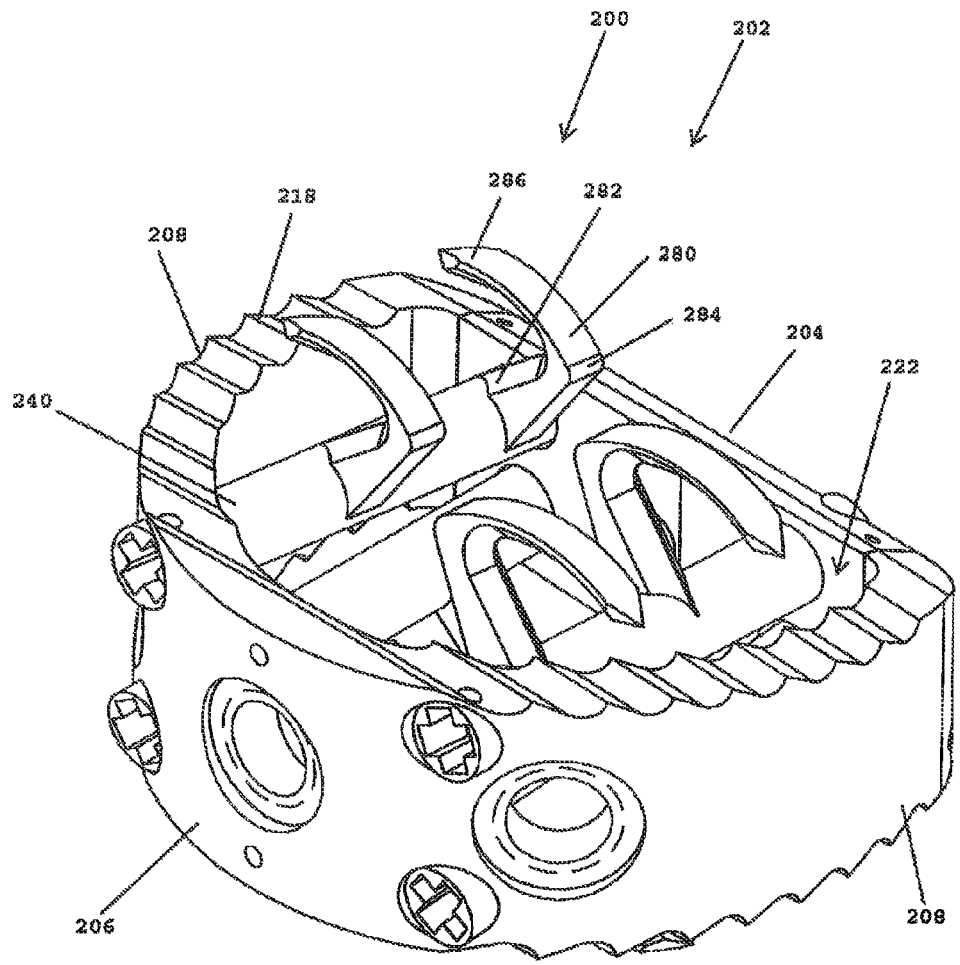
FIG. 9 is a perspective view of an implant device in accordance with another aspect of the invention showing piercing portions rotated out from within a central cavity of an implant body in a securing orientation.
Figure 10:
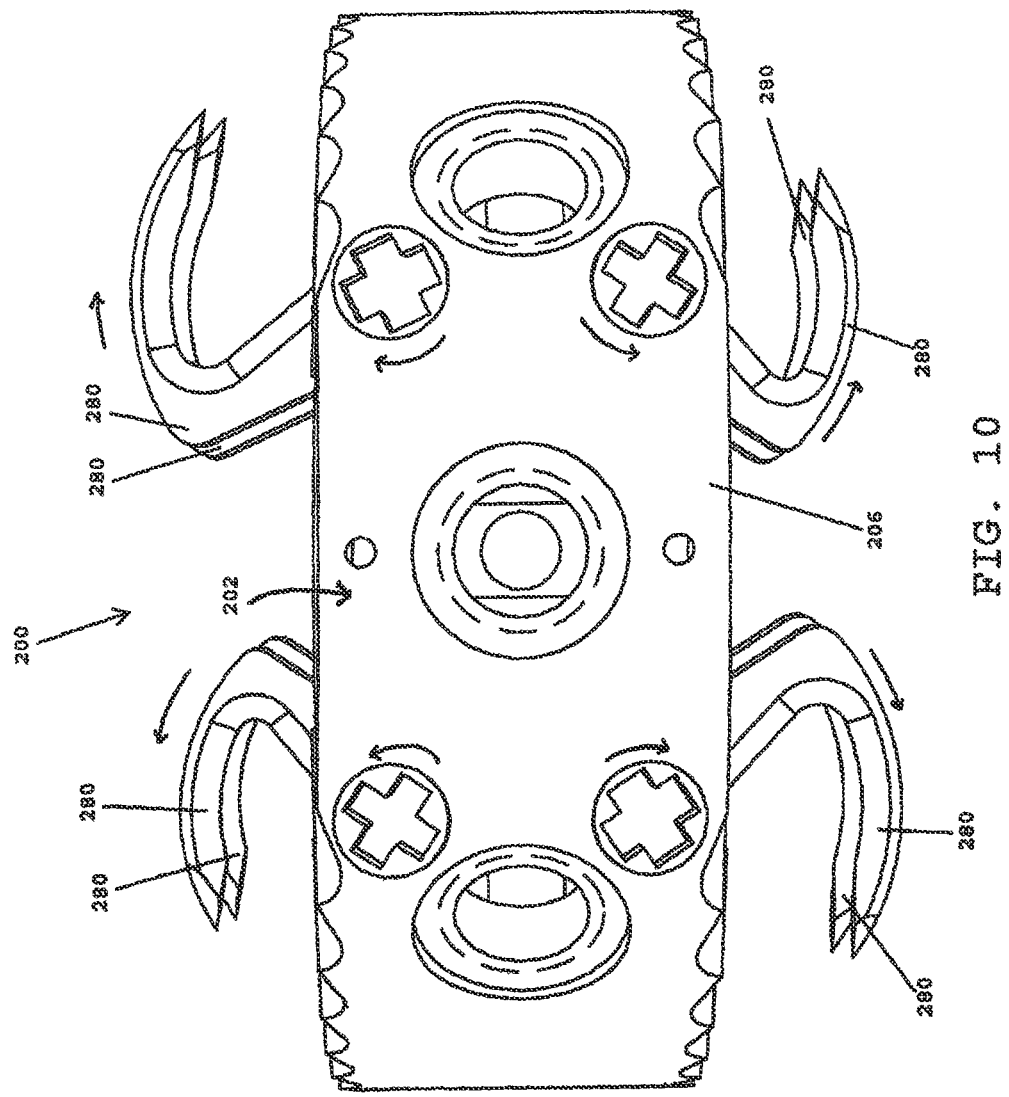
FIG. 10 is an end view of the trailing edge of the implant device of FIG. 9 showing the piercing portions in the securing orientation.

As shown in FIGS. 1, 2, the piercing portions 180 extend generally away from the nearest lateral edge 108 and toward the center of the implant body 102. Alternative embodiments include, for example, piercing portions 180 extending away from the center of the implant body 102 (as shown in FIGS. 9, 10), all the piercing portions 180 extending in the same direction, or the piercing portions 180 extending in a plurality of directions. Preferably, the piercing portions 180 extend in at least two different directions to provide additional stability in securing the implant device 100 to the adjacent vertebrae. In particular, having piercing portions 180 extending in at least two different and preferably generally opposite directions toward each other allows the implant body 102 to be secured to the adjacent vertebral body 10 without urging the vertebral body 10 in one of these directions, thereby avoiding potential damage to the spine and allowing the implant device 100 to be secured in the desired location.

In a preferred embodiment, as shown in FIGS. 1-9, the rotatable portions 140 are positioned adjacent the upper and lower surfaces 110, 112 and toward the lateral edges 108 of the implant body 102. By positioning the rotatable portions 140 away from the center of the implant body 102, the implant device 100 engages the vertebral bodies at four distinct, spaced locations, providing for a more secure engagement which does not require additional securing methods, such as a pedicle screw or lumbar plate, thereby simplifying the process of securing the vertebral bodies 10 with an implant device 100.

Figure 19:
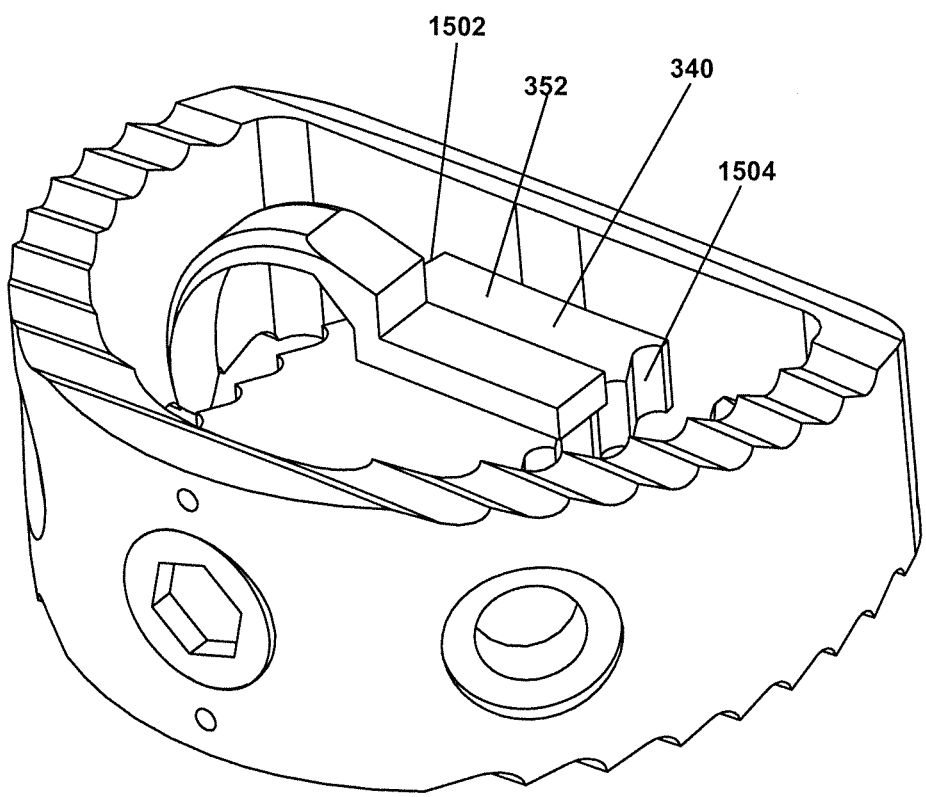
FIG. 19 is a perspective view of the implant device of FIG. 17 showing the piercing portions rotated into the central cavity in an insertion orientation.
Figure 20:
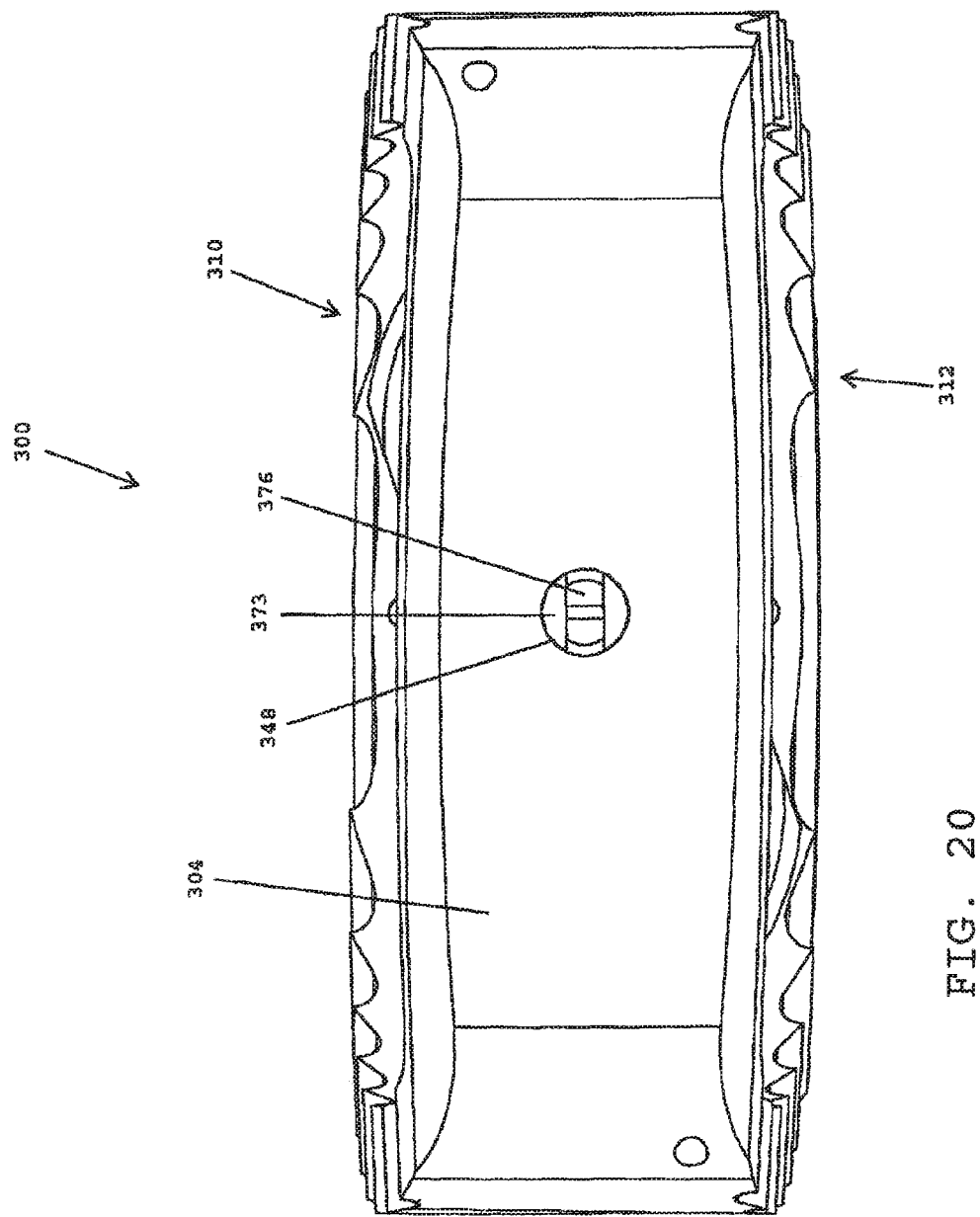
FIG. 20 is an end view of the implant device of FIG. 17 showing a leading edge of the implant body with the piercing portions in the insertion orientation.
Figure 22:
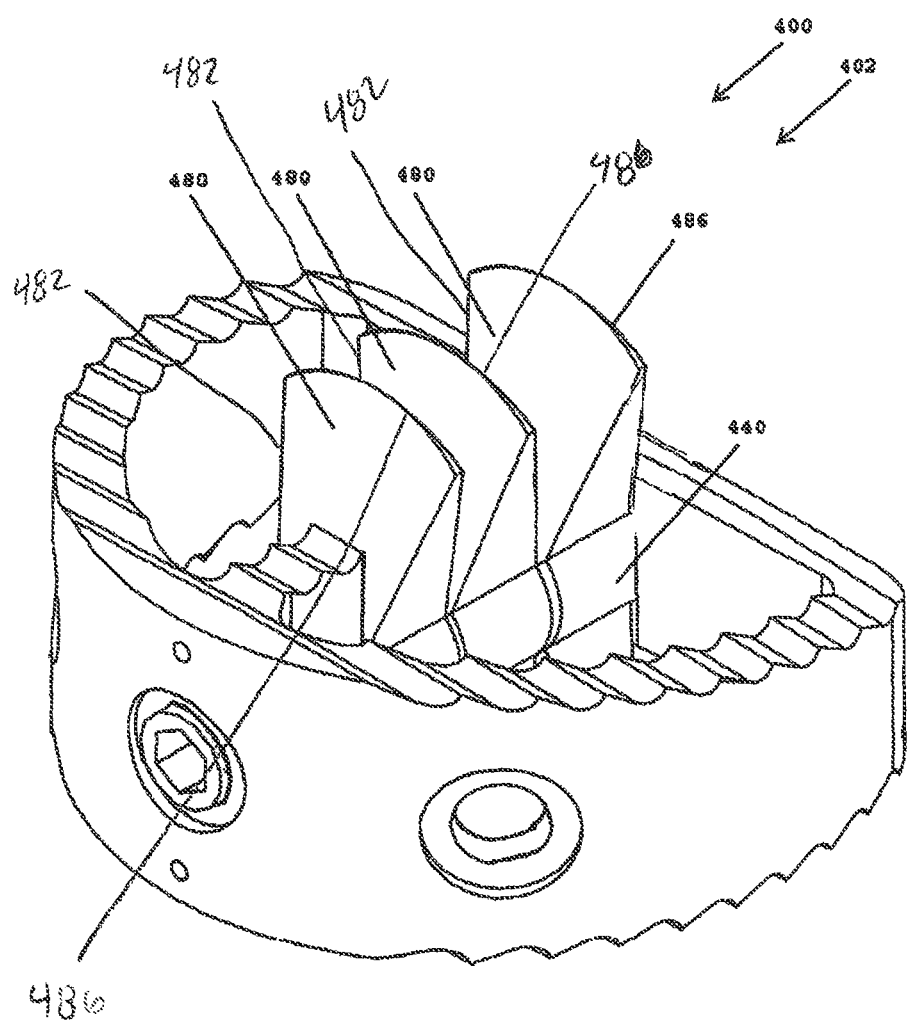
FIG. 22 is a perspective view of an implant device in accordance with another aspect of the invention showing the piercing portions rotated out from within a central cavity of an implant body in a securing orientation.
Figure 23:
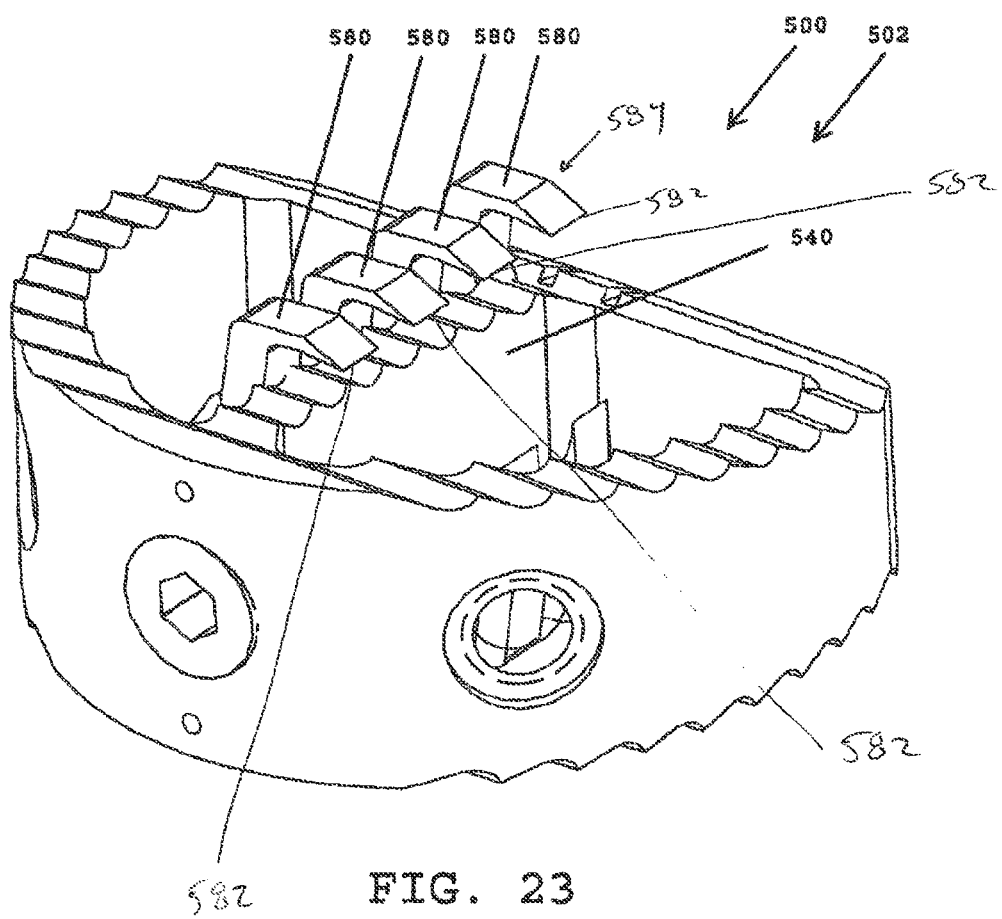
FIG. 23 is a perspective view of an implant device in accordance with another aspect of the invention showing the piercing portions rotated out from within a central cavity of an implant body in a securing orientation.
Figure 24:
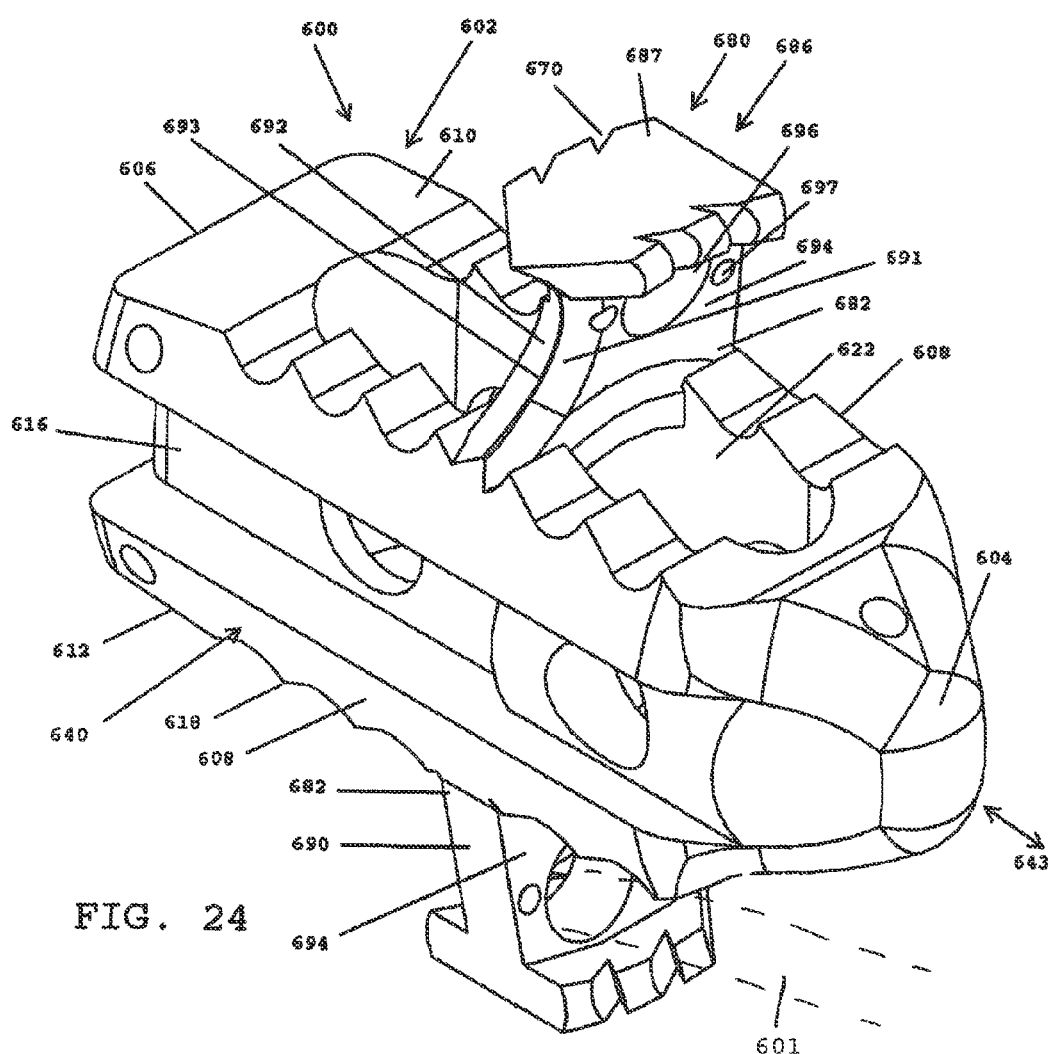
FIG. 24 is a perspective view of an implant device in accordance with another aspect of the invention showing piercing portions extend across a cavity of the implant body and a securing member in phantom extending through a securing throughbore of one of the piercing portions.
Figure 29:
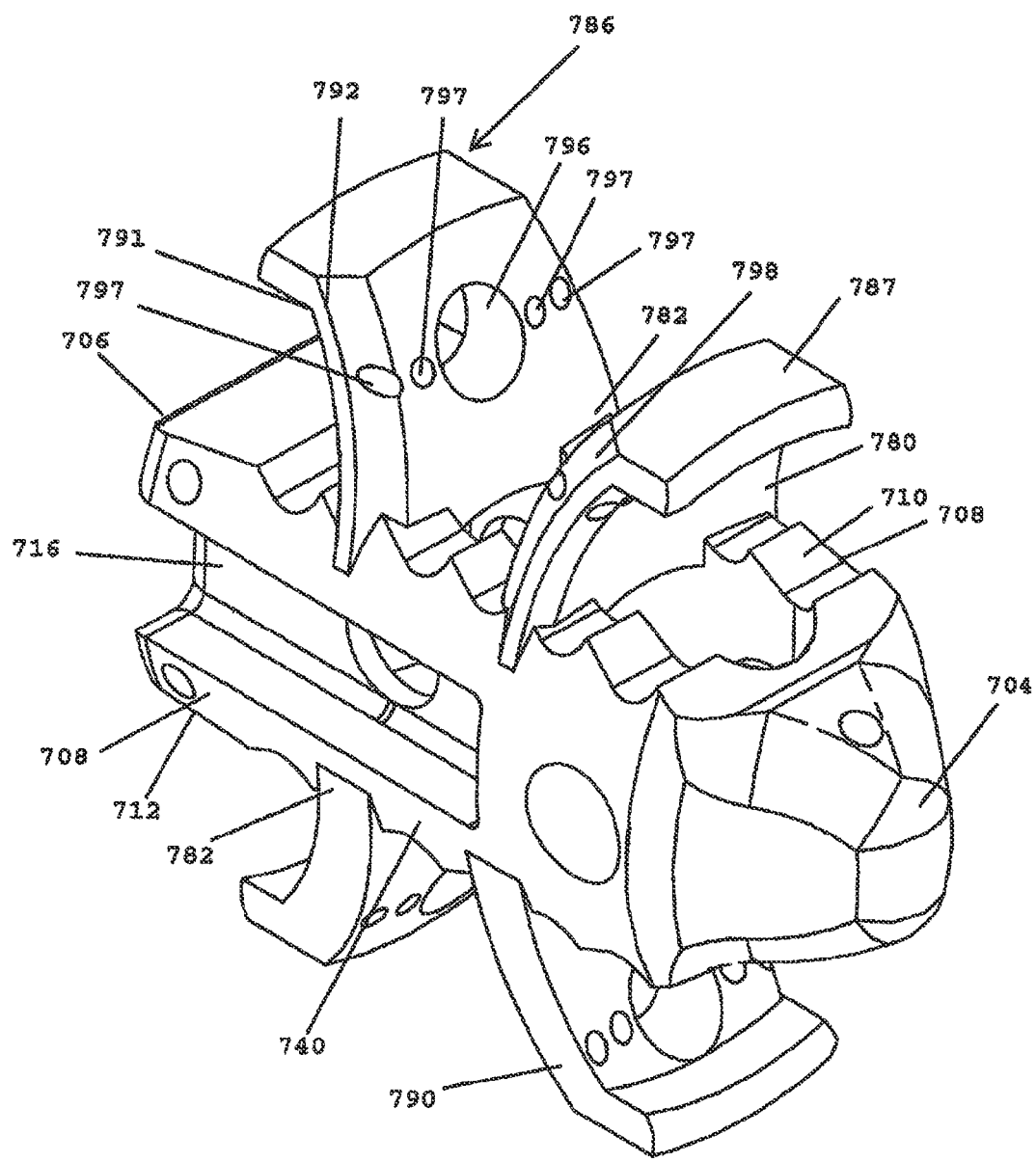
FIG. 29 is a perspective view of an implant device in accordance with another aspect of the invention showing piercing portions extending across a central cavity of an implant body.

The configuration of the piercing portion 180 is not limited by the examples shown in FIGS. 1-31 and 34-60. It is contemplated that the piercing portion 180 can have any configuration capable of penetrating a vertebral body 10 and providing a secure connection. In particular, various configurations contemplated include a hook-shape as shown in FIG. 19, a fin shape as shown in FIGS. 22, 24, 29, an inverted triangle (preferably with the hypotenuse being the distal end portion), a "T" shape, an inverted "L" shape, or a disc-shape.

In one embodiment, as shown in FIG. 1, the piercing portion 180 includes a crook or bent portion 184 intermediate the proximal portion 182 and the arcuate distal end portion 186. The crook or bent portion 184 allows for the piercing portion 180 to have a longer configuration and be positionable within the central cavity 122 and, as a result, the piercing portion 180 extends further into the adjacent vertebral body 10. As shown in FIGS. 1 and 2, the arcuate end portion 186 extends from the crook or bent portion 184 and has a radius of curvature. Preferably, the radius of curvature is such that, when in the securing orientation, the arcuate portion 186 bows away from the upper surface 110 or lower surface 112 with the end 188 of the piercing portion 180 extending toward the upper or lower surface 110 and 112 of the implant body 102.

The crook or bent portion 184 further aids in urging the implant device 100 toward the vertebral bodies 10 to produce a firm engagement between the vertebral bodies 10 and one or both of the upper and lower surfaces 110, 112. In particular, as the piercing portions 180 rotated into the vertebral bodies 10 the ends 188 extend away from the implant body 102 a distance determined by the length and radius of curvature of the arcuate portions 186 and, after extending that distance, the ends 188 of the piercing portions 180 rotate back toward the implant body 102. As the ends 188 rotate back toward the implant body 102, at least one of the penetrated vertebral bodies 10 and the implant body 102 is urged toward the other, or both are urged and shifted toward each other, resulting in a more secure and flush engagement between the implant device 100 and the vertebral body 102.

The implant device 100 can include a stop mechanism to secure the piercing portions 180 in the appropriate location within the adjacent vertebral body 10. Preferably, the stop mechanism is configured to either prevent over-rotation of the piercing portions 180 beyond the desired location, such as the center support portion or internal wall 120. In particular, as the piercing portions 180 are rotated toward the securing orientation, the internal wall 120 has an outer surface configured be abutted against by a base portion 182 of the piercing portion 180 and prevent further rotation of the piercing portion 180.

Alternatively, the stop mechanism can be configured to prevent the piercing portion 180 from "backing-out" of the vertebral body 10, such as after the piercing portion 180 has been positioned in the desired location or while the piercing portion 180 is being rotated into position, or both. Restricting the rotation of the piercing portions 180 after piercing the vertebral body 10 can further prevent micro-fissures within the vertebral body 10 and bone growth retardation.

In one embodiment, the stop mechanism 1508 extends from the piercing portion 180. Back-out of the piercing portion 180 is prevented by the inclusion of a sharp projection extending backward obliquely off the forward facing piercing portion 180. In one embodiment, the distal end 186 of the piercing portion 180 is configured to include a locking mechanism such as a hook, barb, or similar configuration which permits rotation of the piercing portion 180 in one direction but resists rotation in the opposite direction. For example, the piercing portion 180 can include outwardly extending triangular projections along the length of and on either side of the piercing portion 180.

In an alternative embodiment, the stop mechanism can cause mechanical interference to control rotation of the piercing portion 180. The stop mechanism can be configured to provide mechanical interference between the piercing portion 180 and the implant body 102, between the implant body 102 and the rotatable portion 140, or between the piercing portion 180 and the rotatable portion 140. The stop mechanism can be configured to include a mechanical unlocking mechanism to allow for removal of the piercing portions 180 from the vertebral body 10 and for the removal of the implant device 100 from between the adjacent vertebrae. Examples of an unlocking mechanism include a button, lever, removable pin, a mechanical reversal or any other mechanically actuated mechanism suitable for such purpose.

As discussed above, the stop mechanism can include an engagement surface of the central support portion or internal wall 120. In particular, the engagement surface restricts the piercing portion 180 from over-rotation by being abutted by the piercing portion 180 when the piercing portion 180 is rotated toward the desired configuration.

Alternatively, the stop mechanism can include a pin or screw member inserted into the vertebral body 10 to impede rotation or movement of the piercing portion 180 within the vertebral body 10. The pin or screw member can extend generally parallel to the upper and lower surfaces 110, 112 of the implant body. The pin or screw member can be accepted within a corresponding throughbore of the implant device 100. Alternatively, the pin or screw member can be positioned adjacent the piercing portion 180, such as adjacent the crook or bent portion 184, to impede movement, of the piercing portion 180 within the implant body 102 and to impede rotation of the piercing portion 180 out from the implant body 102.

Other examples of stop mechanism configurations include a ratchet and pawl mechanism, rack and pinion, a mechanically actuated locking pin or a friction or snap fit connection between piercing portion 180 and rotatable portion 140, the piercing portion 180 and implant body 102, or the rotatable portion 140 and implant body 102.

Figure 4:
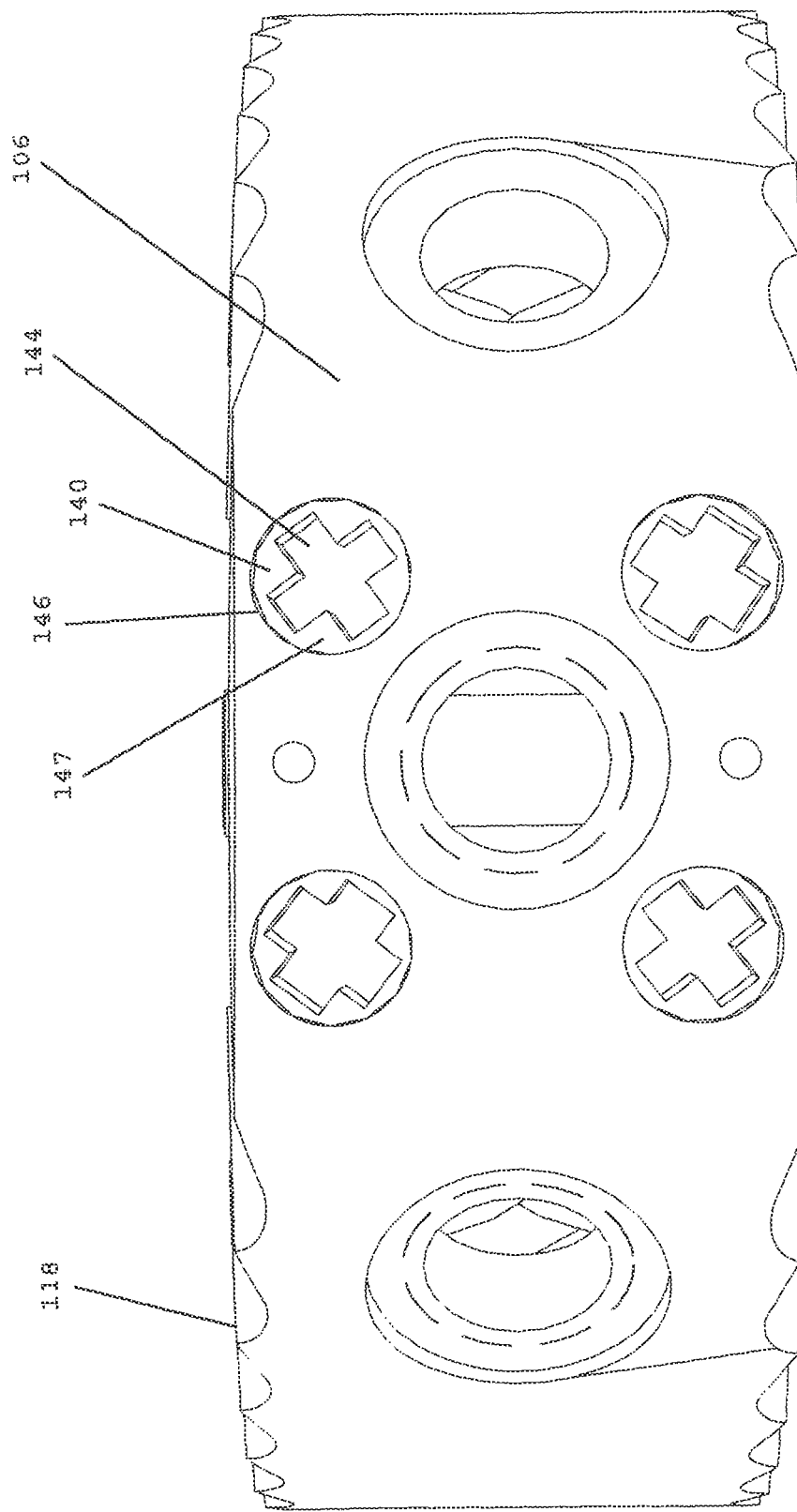
FIG. 4 is an end view of the implant device of FIG. 1 showing tool engagement portions along a trailing edge of the implant body.

As shown in FIGS. 1-8, a plurality of gripping portions or teeth 118 may be formed on the upper and lower surfaces 110, 112 of the implant body 102 for engaging the adjacent vertebrae. As illustrated in FIGS. 1, 4, 5, the gripping portions 118 are defined in the upper and lower surfaces 110, 112 by a plurality of generally arcuate channels 119 extending generally perpendicular to the axis 142 of the implant body 102. As shown, the gripping portions 118 are uni-directional so that they assist in insertion of and resist explantation of the implant body 102. Alternatively, the gripping portions 118 can include individual teeth. Further, in alternative embodiments, the channels 119 can extend in a direction which is not generally perpendicular to the axis 142 or, the channels 119 can extend in more than one direction.

Preferably, the gripping portions 118 are configured to be urged into engagement with the vertebral bodies 10 by rotation of the piercing portion 180 into the vertebral bodies 10. As discussed above, as the piercing portion 180 rotatably penetrates the vertebral body 10. The implant body 102 and vertebral body 10 are urged toward each other into further engagement, thereby resisting explantation of the implant device 100 from between the adjacent vertebrae 10.

Figure 7:
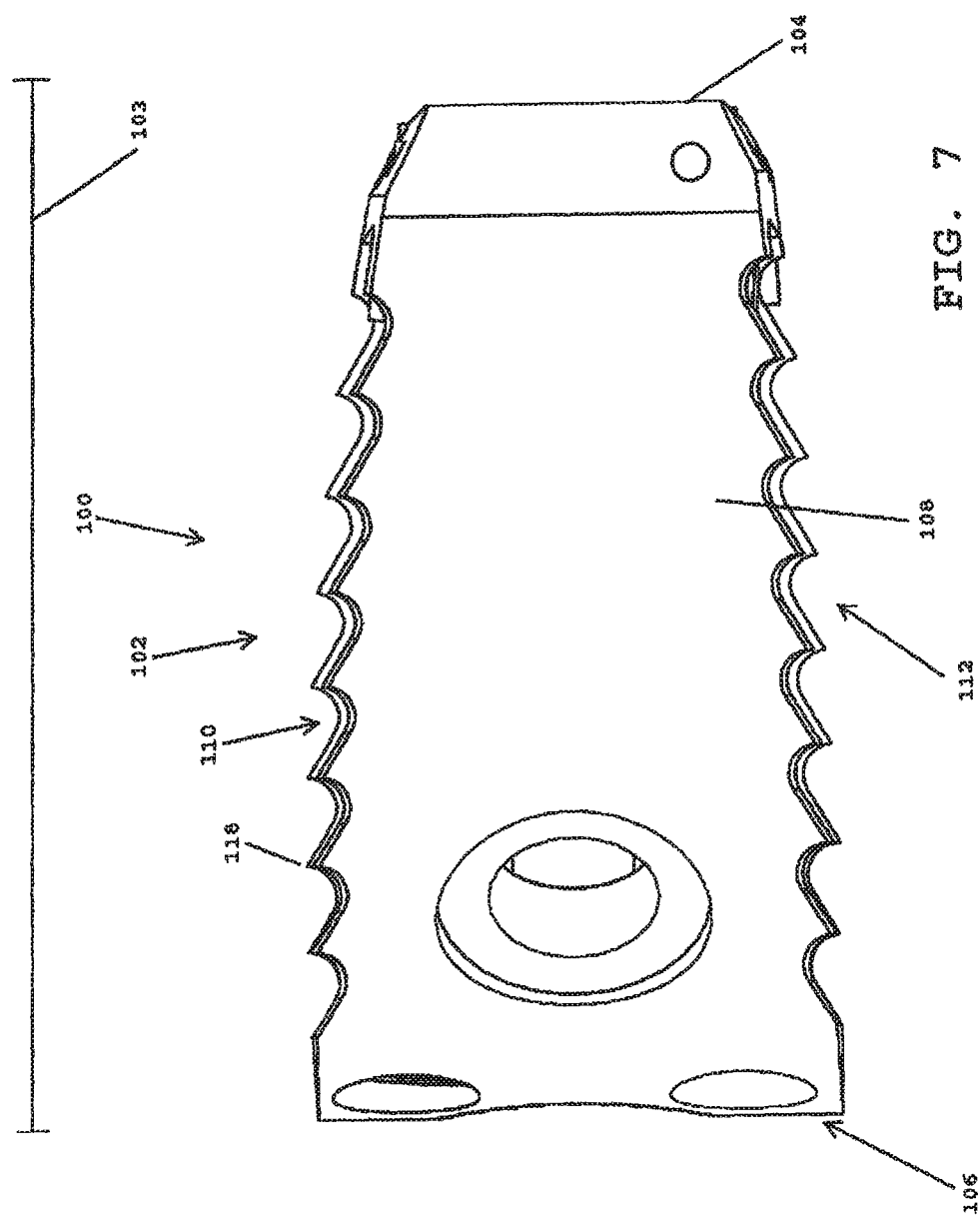
FIG. 7 is a side view of the implant device of FIG. 1.
Figure 8:
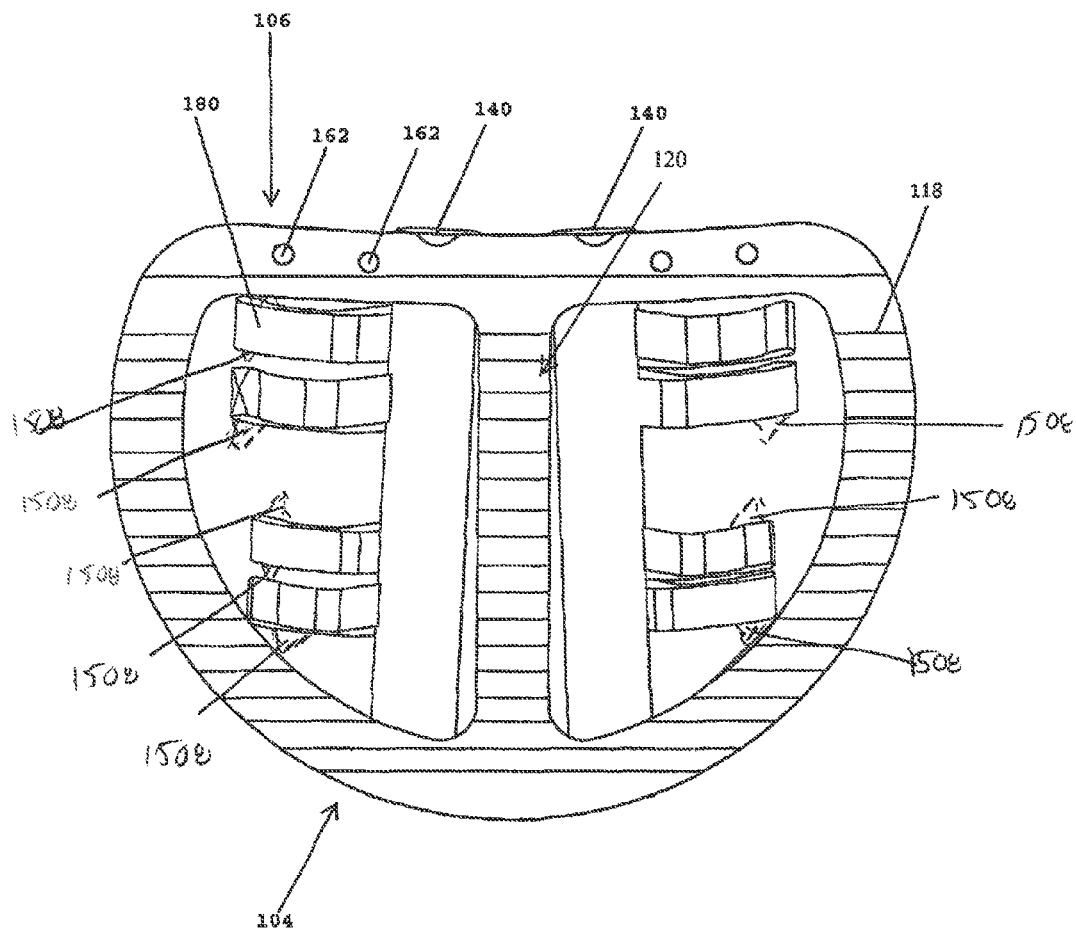
FIG. 8 is a top plan view of the implant device of FIG. 1 showing the piercing portions rotated into the central cavity with barbs in phantom extending from the piercing portions.

As shown in FIG. 7, the upper and lower surfaces 110, 112 of the implant body 102 are slanted with respect to each other so as to provide a generally wedge-shaped implant body 102 having a degree of lordosis. The degree of lordosis of the implant body 102 preferably corresponds to the natural lordosis of the lumbar spine. More specifically, the upper surface 110 has a line of lordosis extending through the upper leading edge 104 and the upper trailing edge 106 of the implant body 102, and lower surface 112 has a line of lordosis extending through the lower leading edge 104 and the lower trailing edge 106 of the implant body 102, such that the upper and lower surfaces 110, 112 are spaced apart a greater distance at the trailing edge 106 of the implant body 102 than at the leading edge 104 of the implant body 102, and the implant body 102 has a height at the trailing edge 106 that is greater than a height at the leading edge 104.

Further, the line of lordosis of the upper surface 110 intersects the axis 142 of the implant body 102 at a first angle. Similarly, the line of lordosis of the lower surface 112 intersects the axis 142 of the implant body 102 at a second angle. The first and second angles may have any suitable size. Preferably, the first and second angles are sized to provide a degree of lordosis of the implant body 102 that best matches the natural lordosis of the spine. In one preferred form, the first angle is the same size as the second angle.

Alternatively, the upper surface 110 and the lower surface 112 are configured to be convex. The convex configuration of the upper surface 110 and the lower surface 112 may have any suitable convexity. The convexity is preferably selected to provide the best match to the natural concavity of the vertebral endplates.

Referring next to FIGS. 9-16, an alternative implant device 200 is shown. The following description will focus on the differences between the implant device 100 and the implant device 200, while a repeated description of the otherwise similar or identical features is generally omitted.

Figure 11:
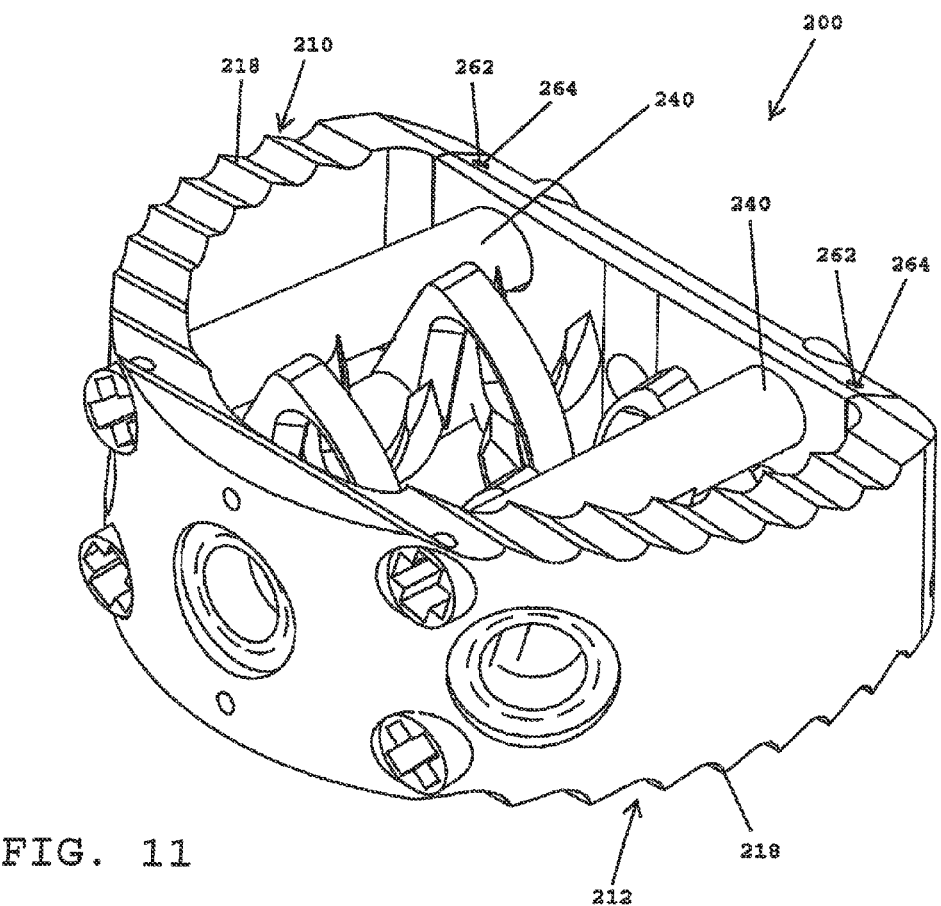
FIG. 11 is a perspective view of the implant device of FIG. 9 showing the piercing portions rotated into the central cavity in an insertion orientation.
Figure 12:
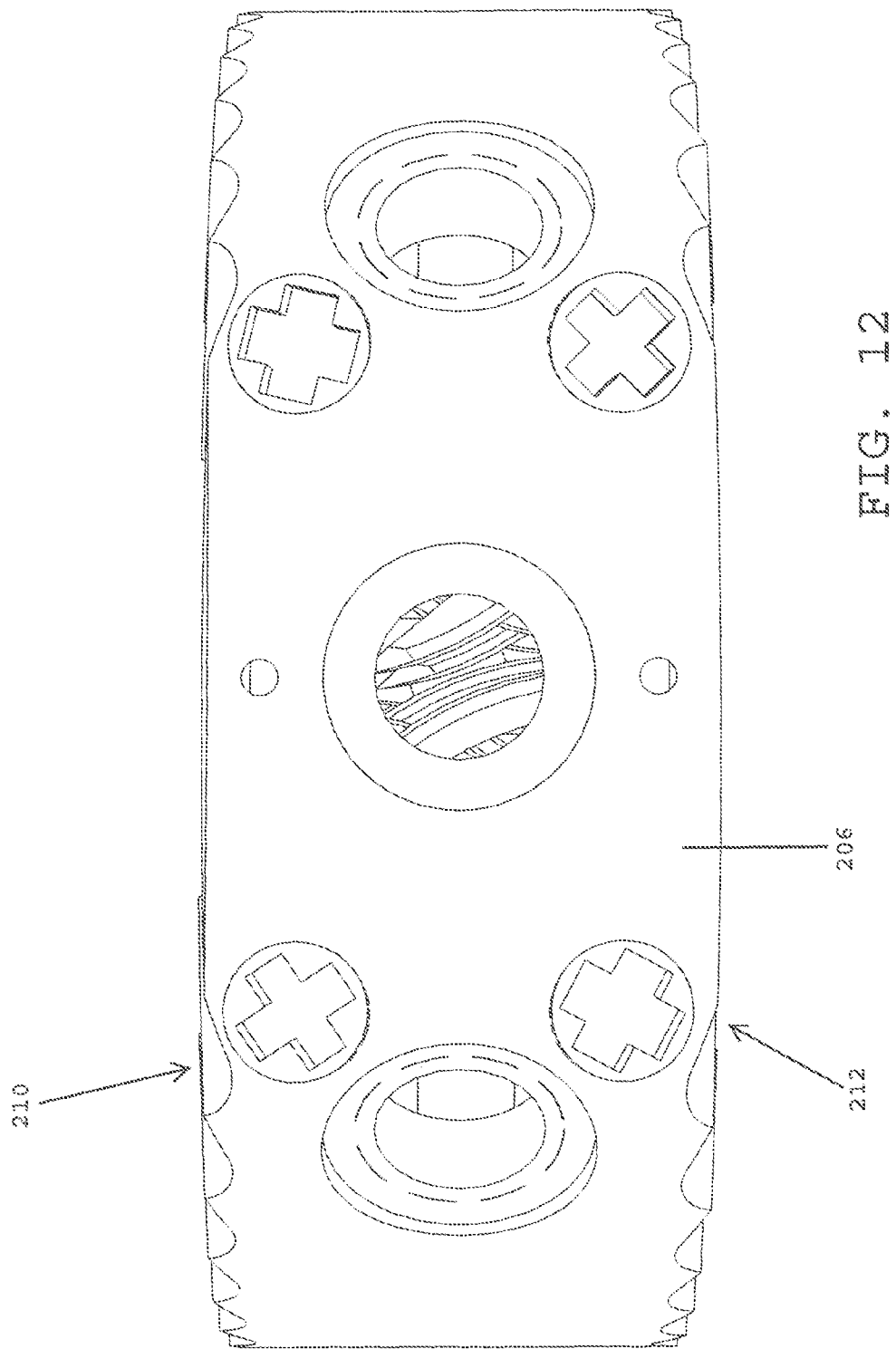
FIG. 12 is an end view of the implant device of FIG. 9 showing tool engagement portions along a trailing edge of the implant body.

As in implant device 100, implant device 200 includes an implant body 202, a rotatable portion 240 and piercing portions 280. As shown in FIGS. 9, 10, piercing portions 280 extend in the opposite direction as the illustrated piercing portions 180. That is, piercing portion 280 include a distal end portion 286 which, when arranged in the securing orientation, extends toward the nearest lateral edge 208 rather than extending toward the lateral edge 208 furthest from the piercing portion, as in implant device 100. As in implant device 100, and as shown in FIGS. 9, 11, implant device 200 preferably includes multiple rotatable portions 240 with at least one piercing portion 280 extending from each of the rotatable portions 240. By having the distal end portion 286 extend through the center portion of the vertebral body 10, which tends to be softer and less dense, and then extend to the outer portion of the vertebral body 10, which tends to be harder and denser, the implant device 200 may be more firmly secured to the vertebral body 10.

Figure 16:
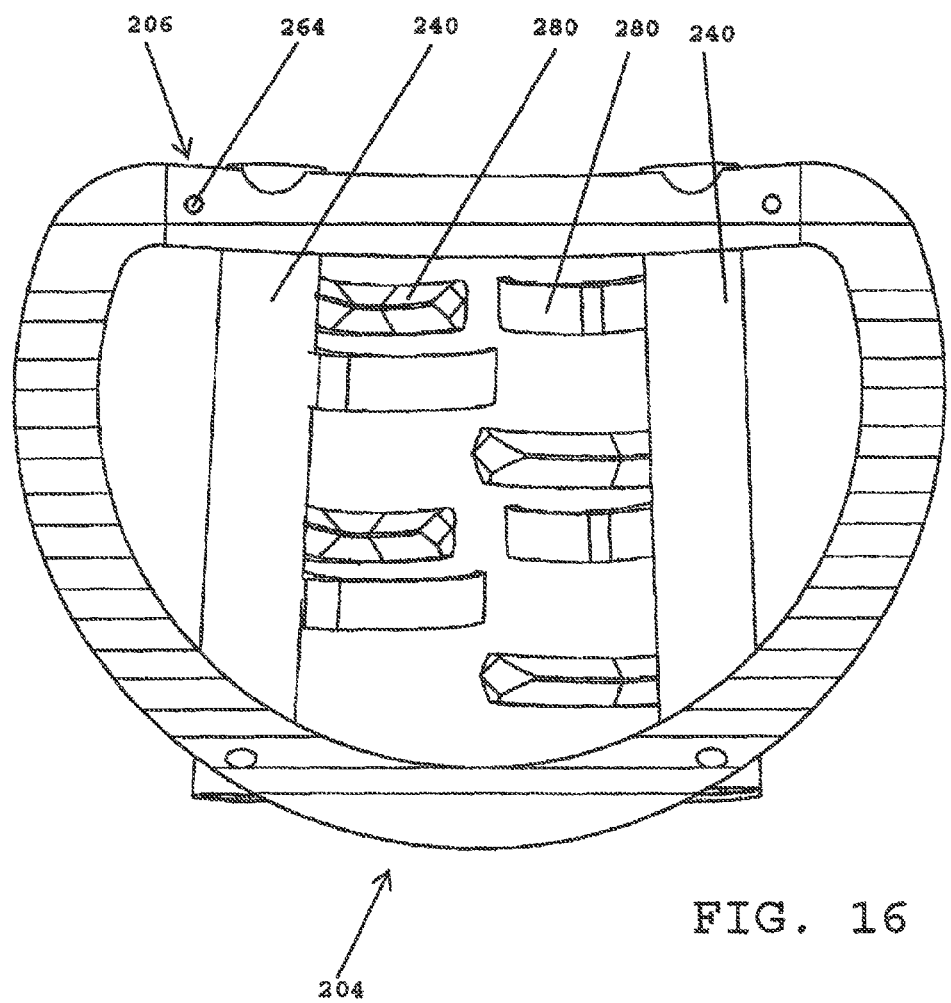
FIG. 16 is a top plan view of the implant device of FIG. 9 showing the piercing portions rotated into the central cavity.

As shown in FIGS. 9, 11, 16, in order to accommodate the piercing portions 280 of implant device 200 within the central cavity 222, the central cavity 222 extends from lateral edge 208 to lateral edge 208, without a central wall or support portion therebetween. In the insertion orientation, the piercing portions 280, as illustrated in FIG. 16, extend across the central cavity 222 such that a central support or wall, as in implant device 100, would impede the piercing portions 280 from being positioned within the central cavity 222. However, it is contemplated that if the implant device 200 included piercing portions 280 which extended from only one of the upper and lower surfaces 210 and 212, a central portion or internal wall could be included along the surface opposite the surface from which the piercing portions 208 extend in the securing orientation.

In addition, the implant body 202 can be configured with the throughbores 246, 248 of the leading and trailing edges 204, 206 positioned toward the lateral edges 208 to provide additional space in the central cavity 222 for the piercing portions 280 to be positioned while in the insertion orientation. More particularly, locating the throughbores 246 and 248 closer to the lateral edges 208 increases the lateral space between the rotatable portions 240 adjacent the upper surface 210 and the rotatable portions 240 adjacent the lower surface 212.

Figure 14:
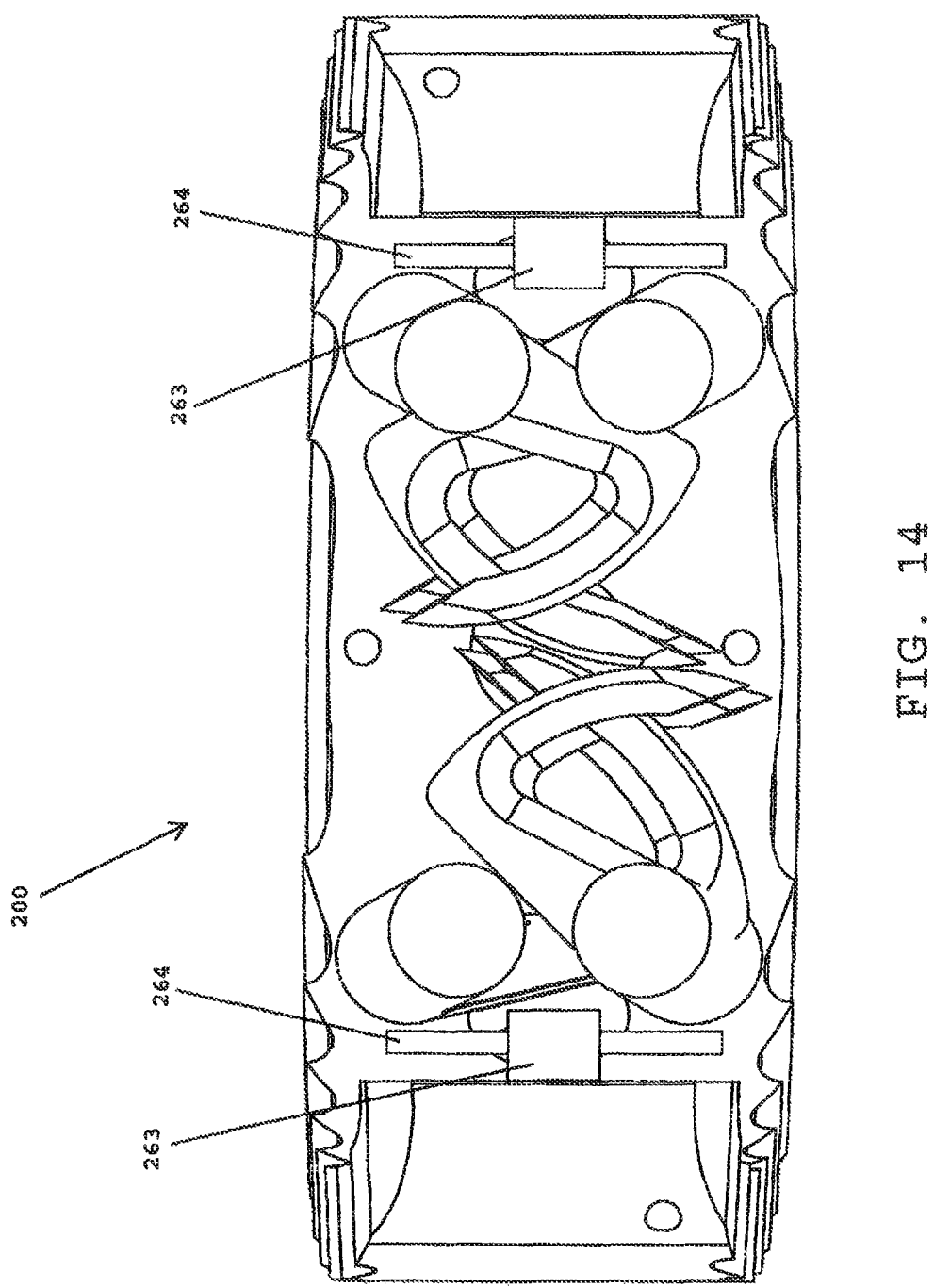
FIG. 14 is an end view of the implant device of FIG. 9 showing the leading edge of the implant body with the securing wall portion removed.
Figure 15:
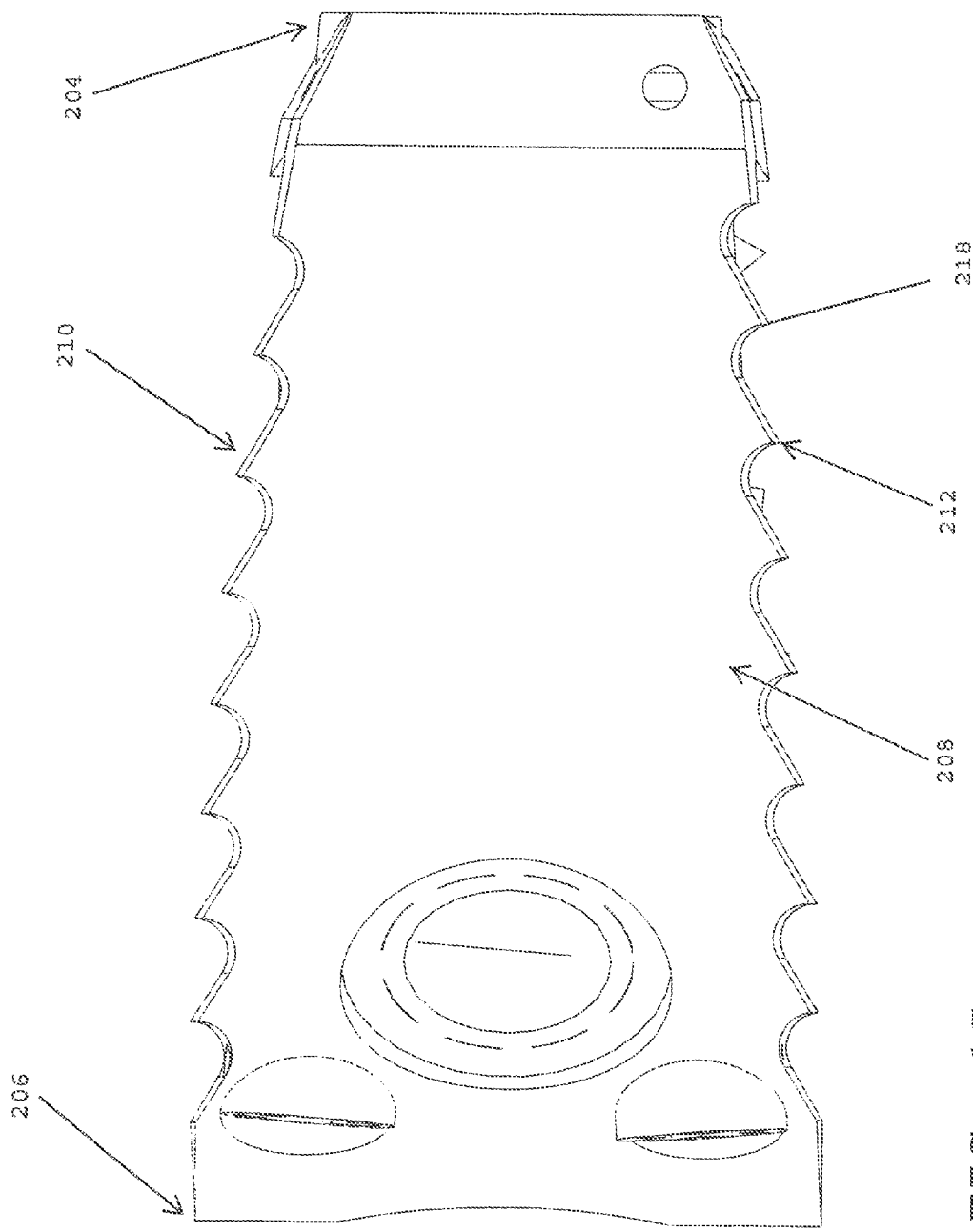
FIG. 15 is a side view of the implant device of FIG. 9.

Further, as shown in FIG. 14, the leading edge 206 preferably includes a removable securing wall portion 260 that extends across the central cavity 222. The removable securing wall portion 260 is connected to the leading edge 206 and includes annular throughbores 246 corresponding to the throughbores 248 of the trailing edges for receiving ends of the rotating portions 240 therein.

Figure 13:
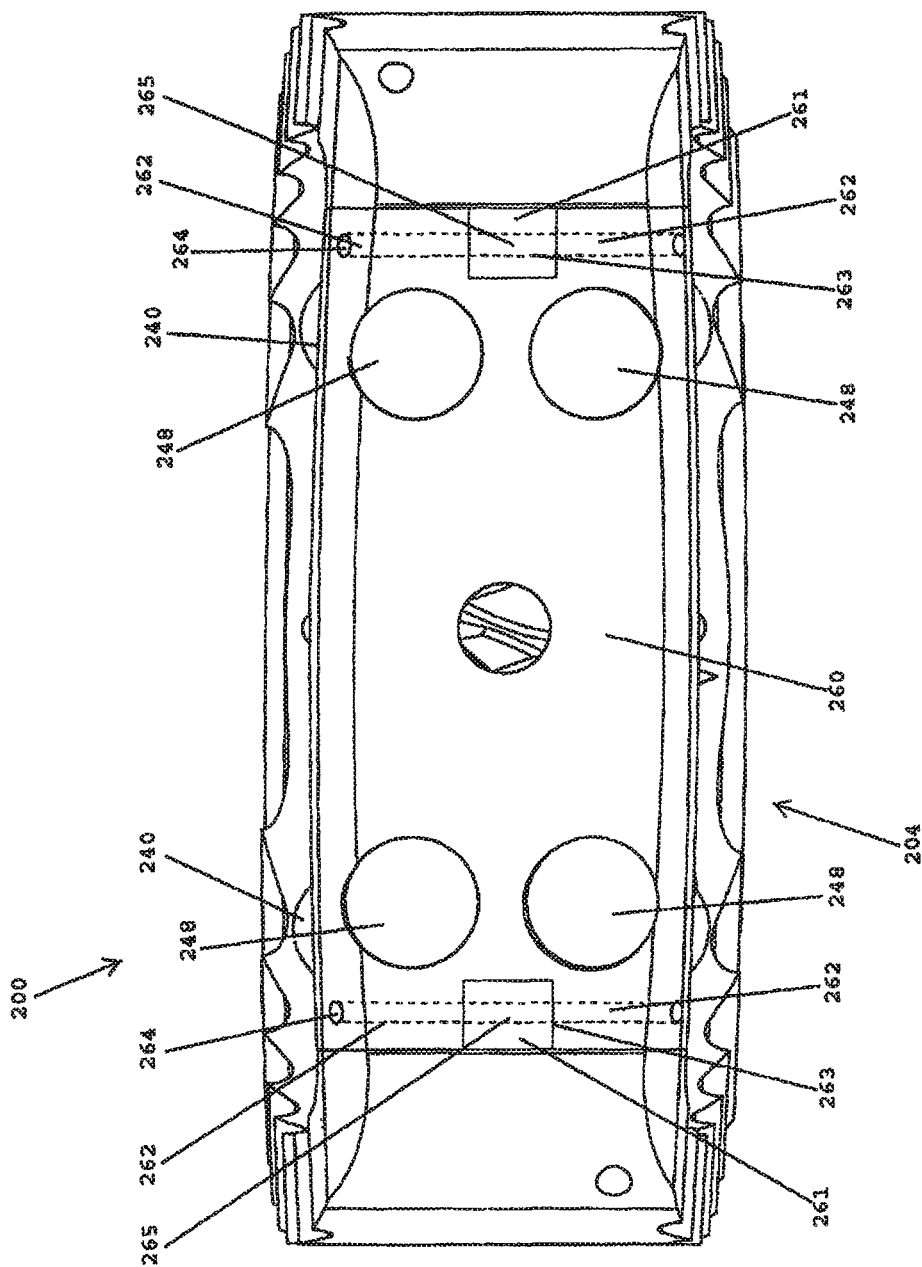
FIG. 13 is an end view of the implant device of FIG. 9 showing a leading edge of the implant body and a securing pin in phantom connecting the leading edge and a removable securing wall portion.

As shown in FIGS. 13 and 14, the leading edge 206 includes securing bosses 261 sized to be received in corresponding securing slots 263 of the removable securing wall portion 260. A securing aperture 262 extends from the upper edge of the removable securing wall portion 260, through the securing wall portion 260 to the securing slot 263 and from the slot 263 through the removable securing wall portion 260 to the lower edge of the removable securing wail portion 260. A corresponding securing aperture 265 extends through the securing bosses 261 of the leading edge 206. The securing apertures 262 and 265 are configured to accept a securing member 264, such as a pin, therein to secure the removable securing wall portion 260 to the leading edge 206 of the implant body 202.

Referring next to FIGS. 17-21, an alternative implant device 300 is shown. The following description will focus on the differences between the implant device 100 and the implant device 300, with a repeated description of the otherwise similar or identical features generally omitted.

Figure 17:
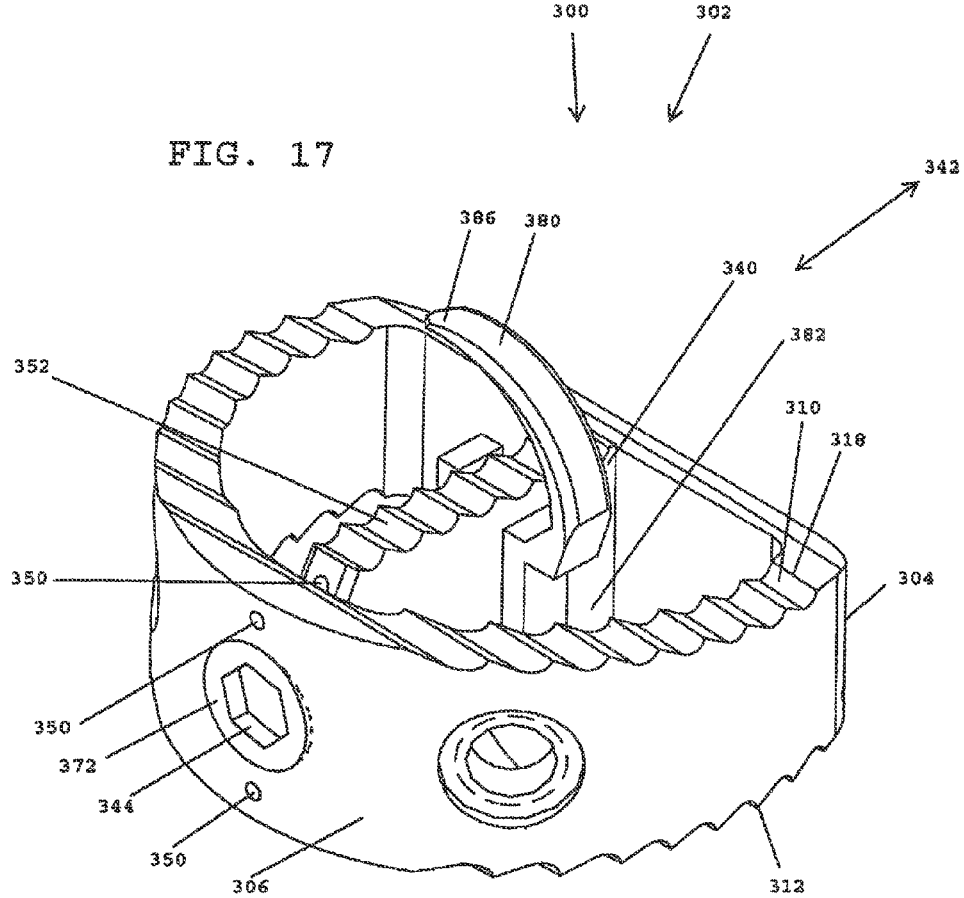
FIG. 17 is a perspective view of an implant device in accordance with another aspect of the invention showing a piercing portion rotated out from within a central cavity of an implant body in a securing orientation.
Figure 18:
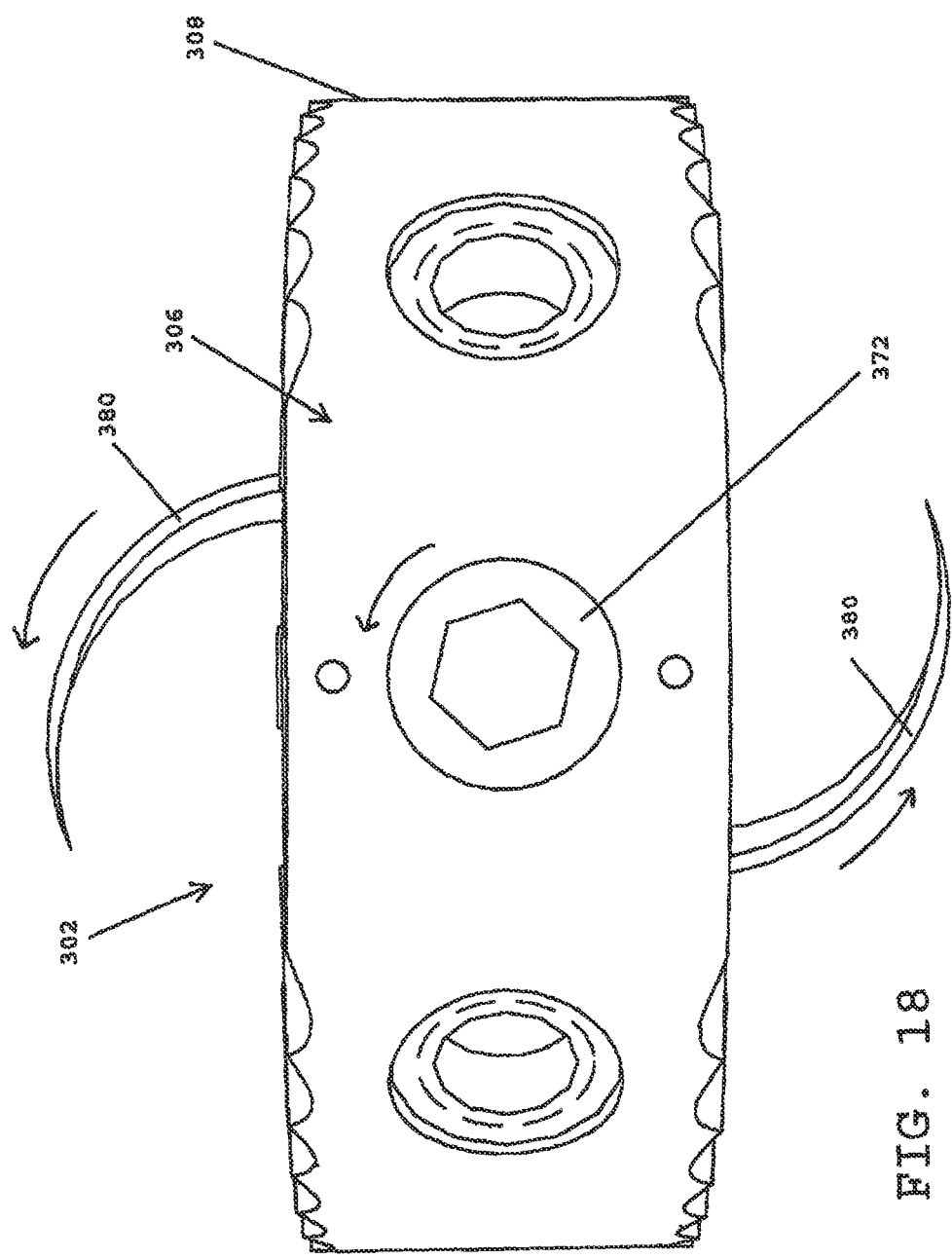
FIG. 18 is an end view of the trailing edge of the implant device of FIG. 17 showing the piercing portions in the securing orientation.

In this embodiment, as shown in FIGS. 17 and 19, the implant device 300 includes a rotatable portion 340 which, when in the securing orientation, also acts like the central support portion or internal wall 120 of implant device 100. In other words, in the implant device 300, the internal wall 340 is rotatable. More particularly, the rotatable portion or wall 340, when in the securing orientation, extends from the upper surface 310 to the lower surface 312 and from the leading edge 304 to the trailing edge 306 of the implant device 300. Preferably, the rotatable portion or wall 340 includes gripping portions or teeth 318 on the narrow opposite surfaces 1502 and 1504 thereof corresponding to the gripping portions or teeth 318 of the implant body 102.

Figure 21:
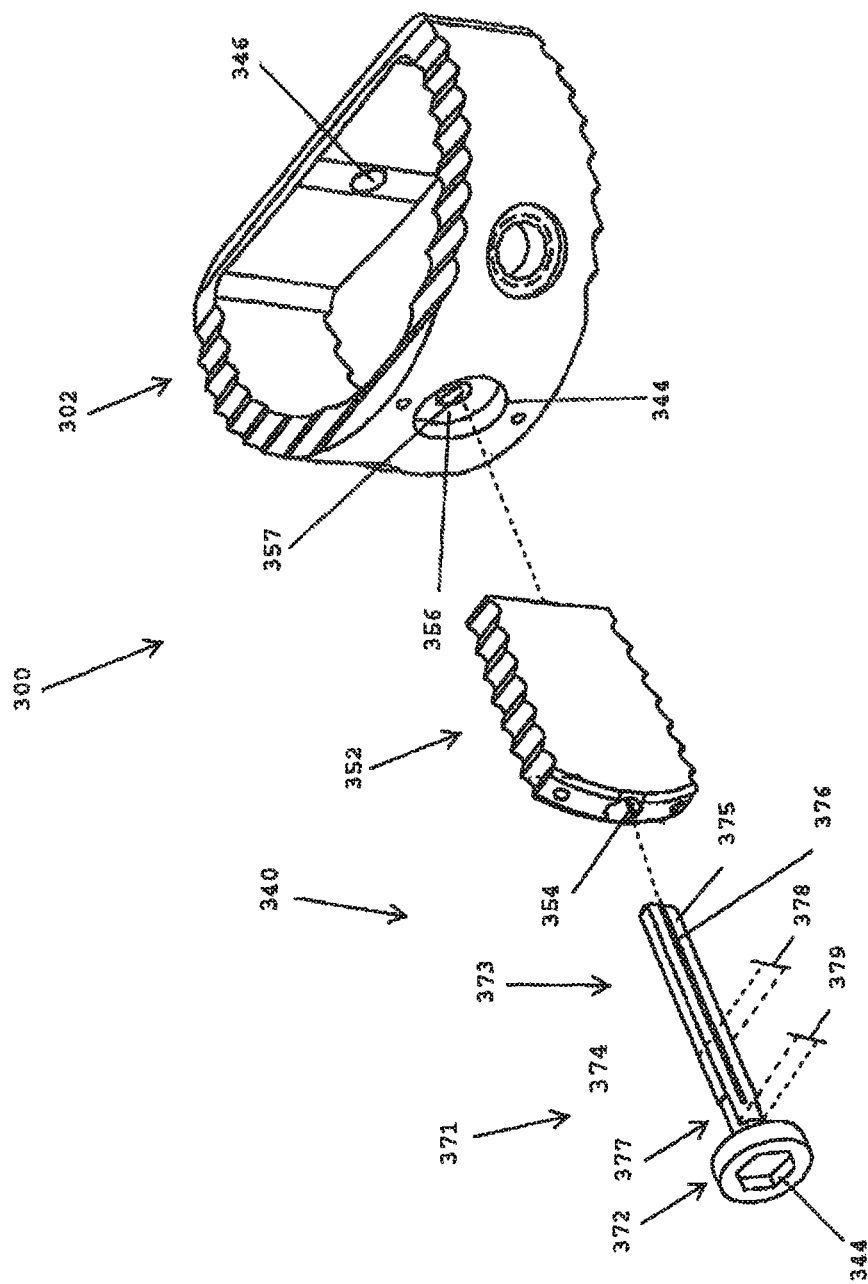
FIG. 21 is an exploded perspective view of the implant device of FIG. 17.

As shown in FIGS. 17 and 21, the rotatable portion 340 includes a body or wall portion 352 and an elongate securing portion 371. The body or wall portion 352 is configured to be received in the cavity 322 and, when in the implanted or securing orientation, extend from the leading edge 304 to the trailing edge 306 and between the upper surface 310 and the lower surface 312 so that the narrow surfaces 1502 and 1504 are arranged as upper and lower toothed surfaces for gripping the corresponding vertebral bodes 10.

The body or wall portion 352 includes a keyed throughbore 354 extending along the length of the body or wall portion 352. The elongate, securing portion 371 includes a head portion 372, a slotted portion 373 and a neck portion 377. The head portion 372 includes a tool engagement end portion 344 therein for being engaged by a tool. As shown, the tool engagement portion 344 includes a hexagonal aperture for receiving an end of a tool therein. The slotted portion 373 includes an upper portion 374, a lower portion 375 and a slot 376 extending between the lower and upper portions 374 and 375. The slot 376 allows the upper and lower portions 374 and 375 to be shifted toward one another thereby varying the height or size of the slotted portion 373. When the upper and lower portions 374 and 375 are not shifted toward one another, the slotted portion 373 has a first height 378 configured to correspond to the keyed throughbore 354 of the body portion 352. The neck portion 377, which is intermediate the head portion 372 and slotted portion 373, includes a second height 379, the second height 379 being smaller than the first height 378.

The throughbore 346 of the trailing edge 306 includes a step 356 therein, the step 356 defining an annular throughbore having a step diameter 357. The annular throughbore of the step 356 is configured to accept the neck portion 377 therein and, in particular, to be larger than the second height 379 of the neck portion 377 and smaller than the head portion 372 and the first height 378 of the slotted portion 373.

The implant device 300 is assembled by inserting the slotted portion 373 of the elongate securing portion 371 through the throughbore 346 of the trailing edge 306. The upper and lower portions 374 and 375 of the slotted portion 373 are urged together into the slot 376, effectively reducing the height 378 of the slotted portion 373 to less than the step diameter 357. The body portion or wall 352 is positioned within the central cavity 322 of the implant body 302 to receive the slotted portion 373 within the keyed throughbore 354. The elongate securing portion 371 is shifted along the axis 342 until the slotted portion 373 is within the throughbore 348 of the leading edge 304, the neck portion 377 is disposed within the step 356 of the trailing edge 306, and the head 372 is disposed within the throughbore 346. The elongated securing portion 371 is thereby secured within the central cavity 322 both laterally, as the elongate securing portion 371 extends through throughbores 346 and 348 thereby preventing lateral movement, and longitudinally, as the elongate securing portion 371 is positioned so that the head portion 372 and slotted portion 373 are on either side of the step 356, with both the head portion 372 and slotted portion 373 sized larger than the diameter 357 of step 356. The keyed throughbore 354 resists compression of the first and second portions 374 and 375 toward one another, thereby maintaining the first height 378 of the slotted portion 373. As a result, the size of the head portion 372 and the height of the slotted portion 373 prevent the elongate securing portion 371 from translating along the axis 342.

The keyed throughbore 354 and elongate securing portion 3721 are configured to transmit torque applied by a tool 1000 engaging the tool engagement portion 344 to the body or wall portion 352 of the rotatable portion 340. In particular, the upper and lower portions 374, 375 of the slotted portion 373 are configured to engage the keyed throughbore 354 and rotate the body or wall portion 352 as rotational force is applied to the tool engagement portion 344.

An exemplary piercing portion 380 is shown in FIG. 17, which includes a thinner and curved overall configuration. As with implant device 100, the piercing portion 380 can include various configurations based on the application and circumstances.

Referring next to FIG. 22, implant device 400, an alternative embodiment of implant device 300, is shown. In particular, implant device 400 includes piercing portions 480 having a wedge-shaped configuration. The piercing portions 480 include a pointed configuration along a leading end 482 and distal end 486 for penetrating the vertebral bodies 10. As the piercing portions 480 are rotated toward a securing orientation, the entire leading end 482 of each piercing portion engages and penetrates one of the vertebral bodies 10. Referring to FIG. 23, implant device 500, an alternative embodiment of implant device 300 is shown. In particular, implant device 500 includes multiple piercing portions 580, similar to piercing portions 180, extending from the upper and lower surfaces 510, 512. The piercing portions 580 each include a flat cutting edge 582 at a distal end 584 of the piercing portions 580 to penetrate the vertebral bodies 10.

Referring next to FIGS. 49-54, an alternative implant device 1200 is shown. The following description will generally focus on the differences between the implant device 100 and the implant device 1200.

The implant body 1202, as shown in FIGS. 49-53, includes a pair of spaced center walls 1208 and an outer wall 1400 extending about the spaced center walls 1208. The outer wall 1400 and the spaced center walls 1208 provide a spaced pair of cavities 1204 configured to extend between adjacent vertebrae 10. The outer wall 1400 includes a leading edge wall 1206 and a pair of sidewalls 1212 extending from either end 1216 of the leading edge wall 1206. The central walls 1208 include adjacent proximal ends 1402 and 1404 which extend from a generally central portion 1210 of the leading edge wall 1206 and adjacent distal ends 1214 which connect to trailing ends 1406 and 1408 of the sidewalls 1212.

Figure 49:
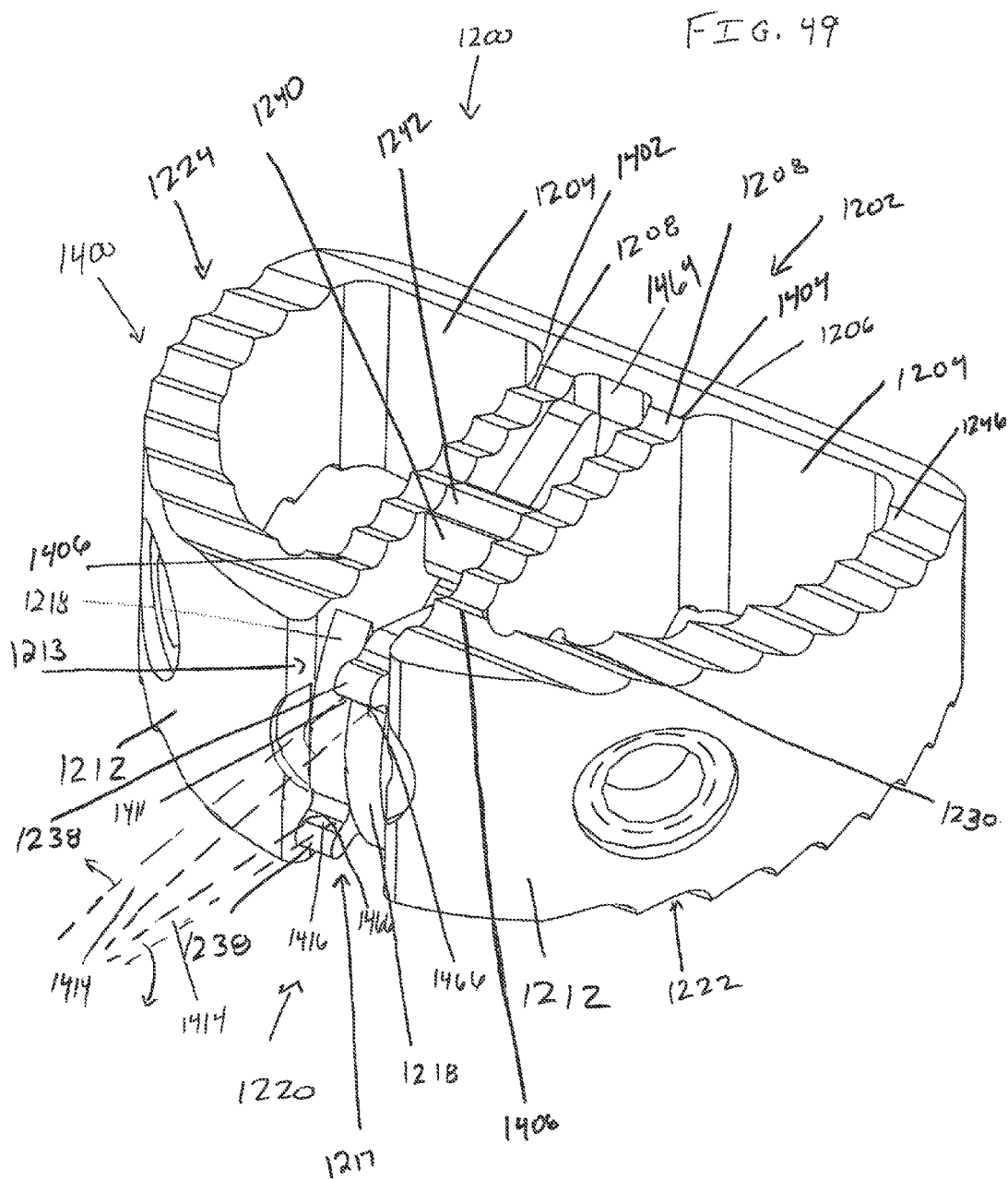
FIG. 49 is a perspective view of an implant device in accordance with another aspect of the invention showing teeth on upper and lower surfaces of an implant body and scissor arms shifted into a cavity of the implant body in an insertion orientation thereof showing a tool in phantom engaging tool engagement portions of the scissor arms.
Figure 50:
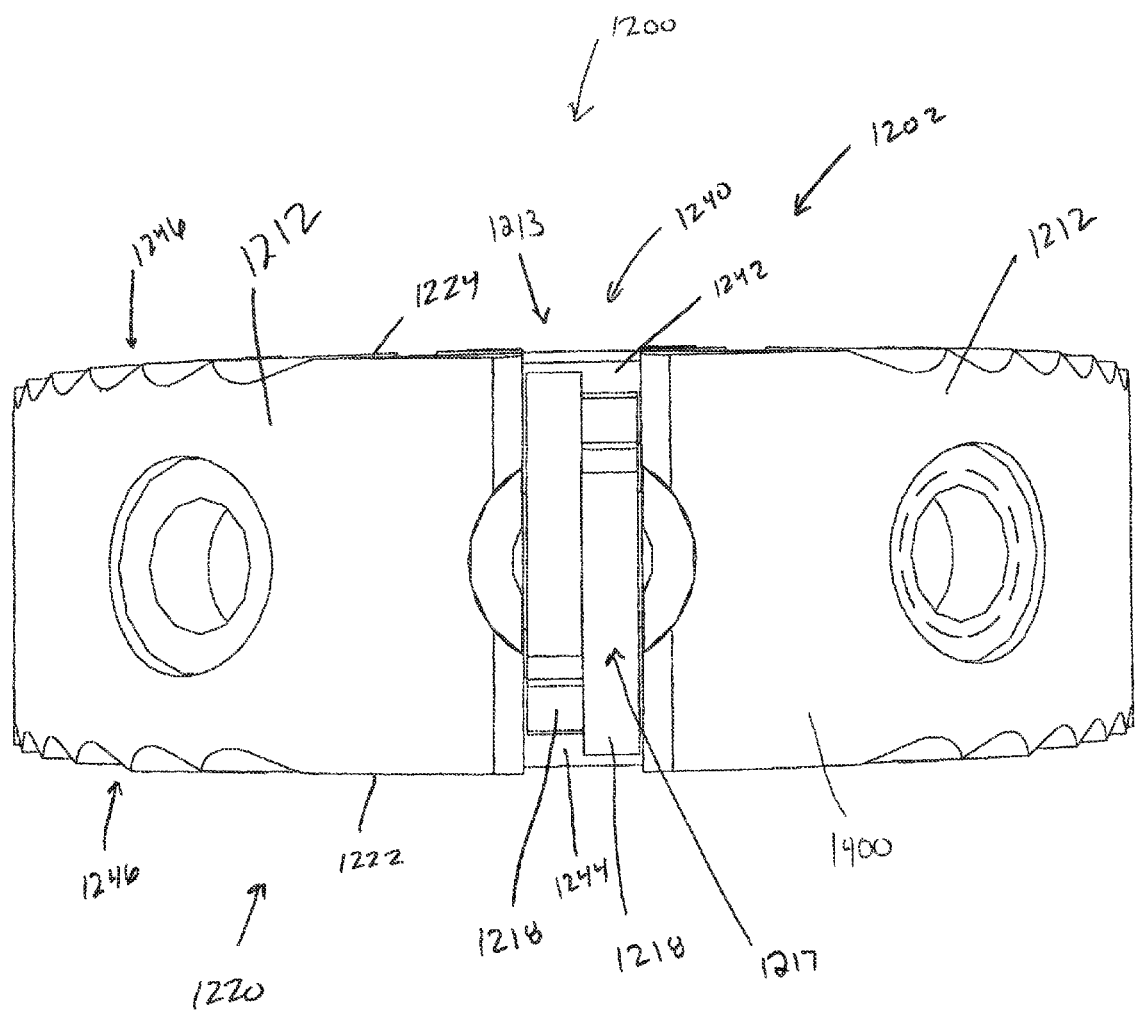
FIG. 50 is a front end elevational view of the implant device of FIG. 49 showing a gap in an outer wall of the implant body with the scissor arms in the insertion orientation.
Figure 51:
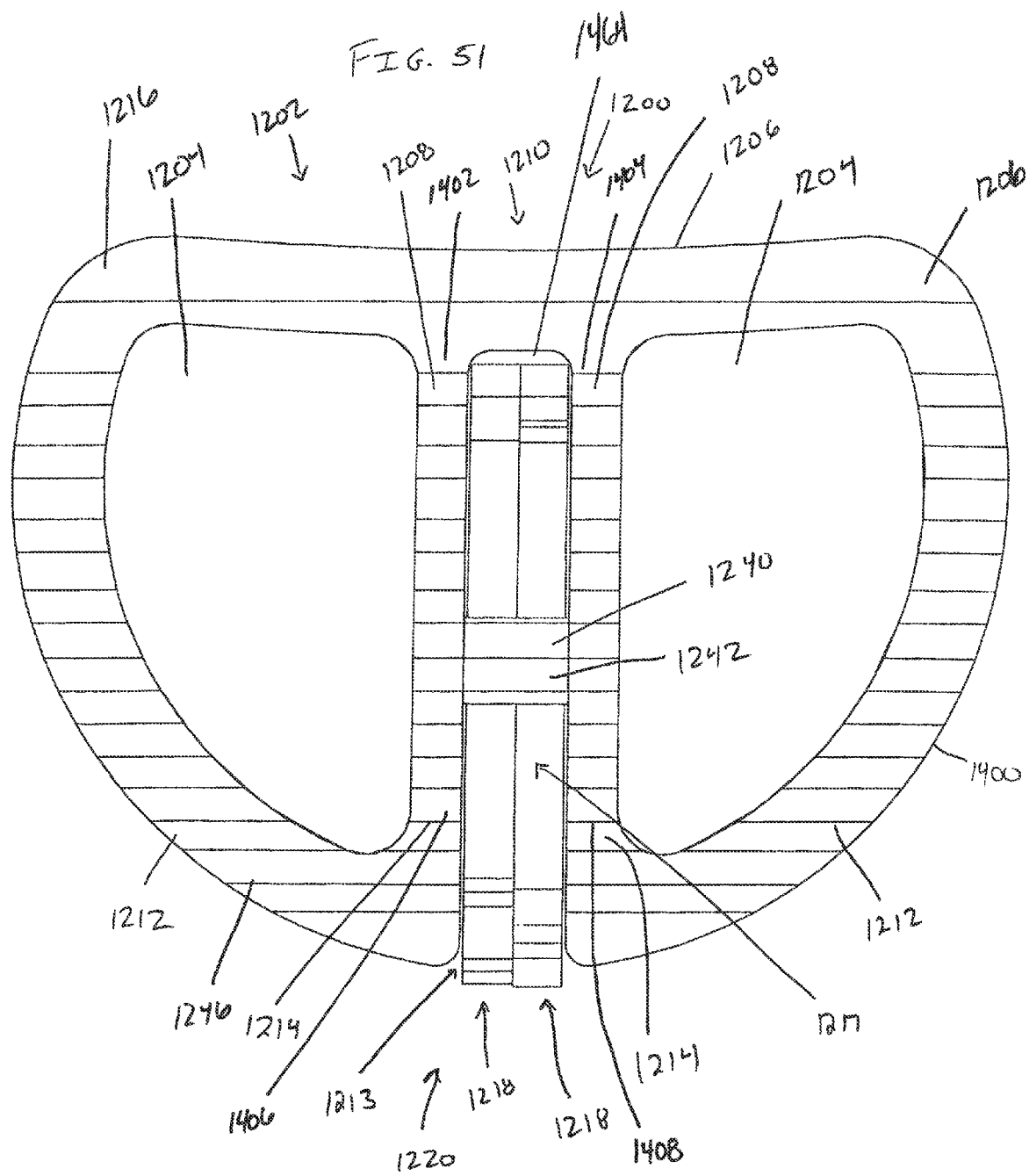
FIG. 51 is a top plan view of the implant device of FIG. 49 in the insertion orientation showing the scissor arms extending into the gap of the outer wall in the insertion orientation.
Figure 52:
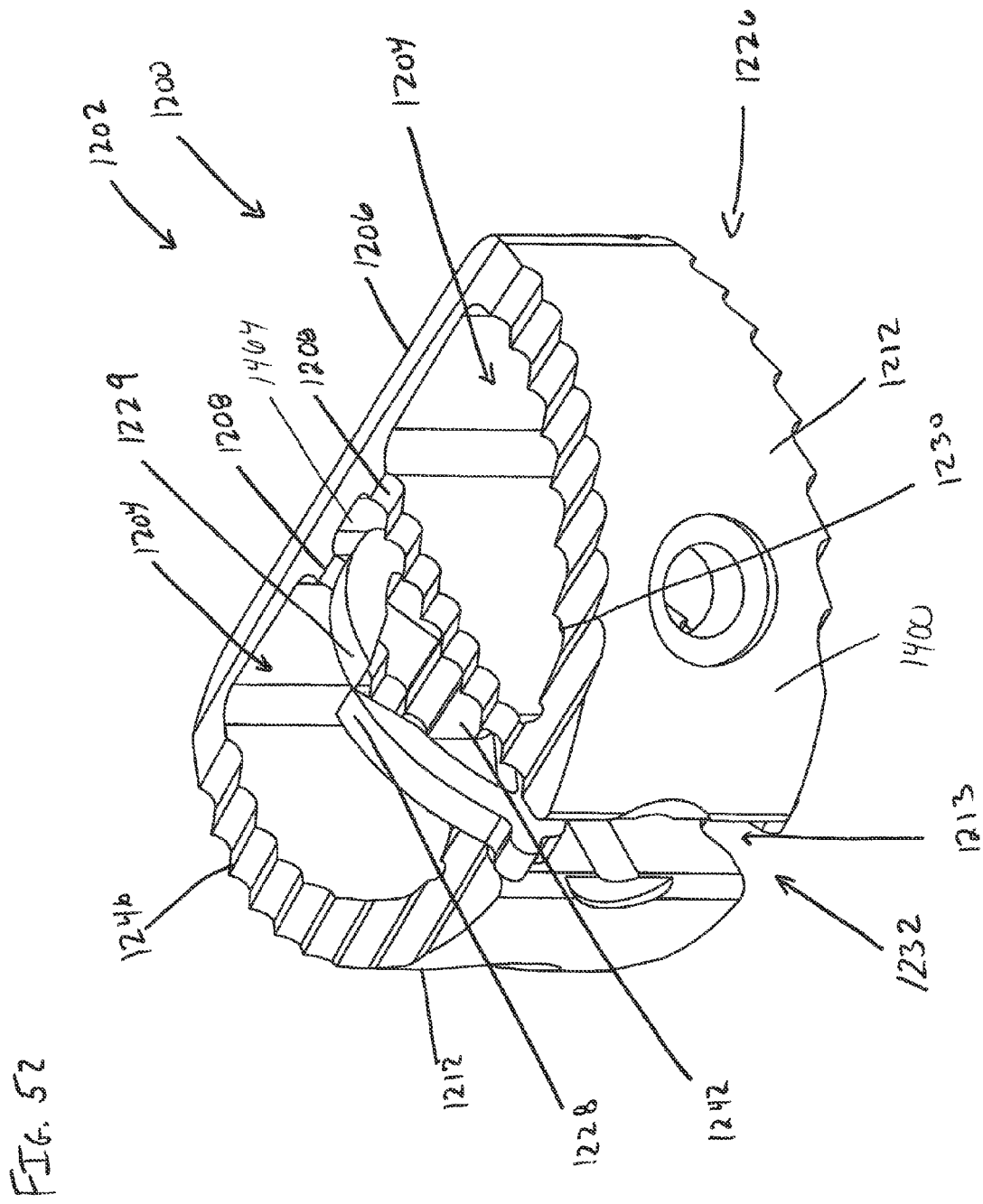
FIG. 52 is a perspective view of the implant device of FIG. 49 showing the scissor arms shifted so that bone penetrating ends of the scissor arms extend beyond the teeth of the upper and lower surfaces of the implant body in a securing orientation.
Figure 53:
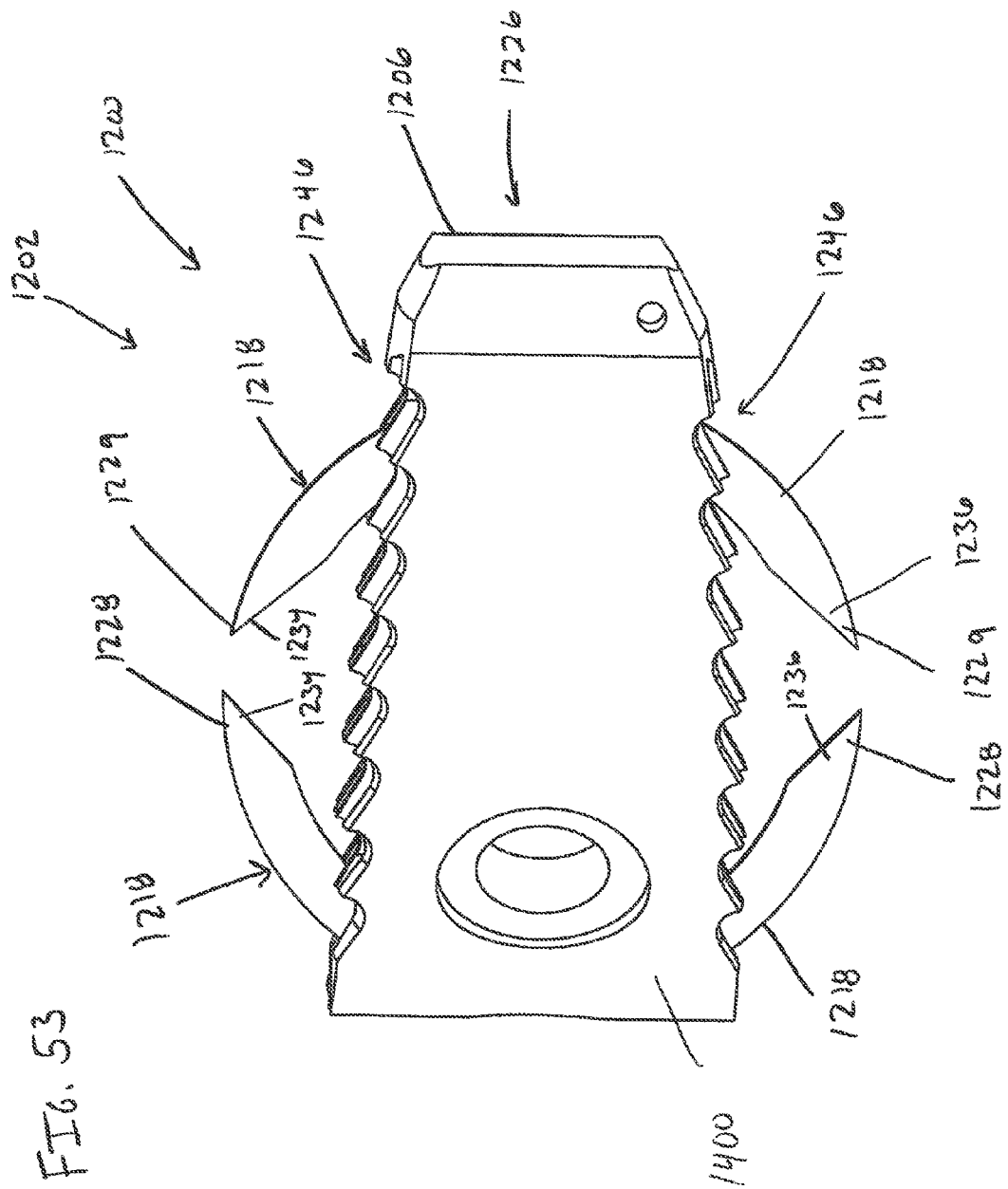
FIG. 53 is a side elevational view of the implant device of FIG. 49 in the securing orientation.

As shown in FIGS. 49-53, the spaced center walls 1208 have a slot opening 1464 therebetween generally rectangular in profile and open at one end to receive an anchoring device 1217 therebetween and closed by the wall 1206 spanning the center walls 1208 at the other end. Similar to the implants 100 and 200 as shown in FIGS. 1 and 11, the anchoring device 1217 includes elongate scissor arms members 1218 configured to pivot between an insertion orientation 1220, as shown in FIGS. 49-51, and a securing orientation 1220, as shown in FIGS. 52 and 53. In the insertion orientation 1220, the scissor arms 1218 are generally positioned between upper and lower surfaces 1222 and 1224 of the implant body 1202 and arcuate bone penetrating ends 1234 and 1236 of the opposite end portions 1228 and 1229 generally do not extend beyond the teeth 1246 of the implant device 1200. In the securing orientation 1226 the bone penetrating ends 1234 and 1236 of the opposite end portions 1228 and 1229 of the scissor alms 1218 extend beyond the implant body upper and lower surfaces 1222 and 1224. However, unlike implants 100 and 200, the scissor arms 1217 have a scissor configuration such that, as shown in FIGS. 49-53, the scissor arms 1218 can pivot about a single pivot member 1230 such as a pivot shaft extending between, the spaced central walls 1208.

Figure 54:
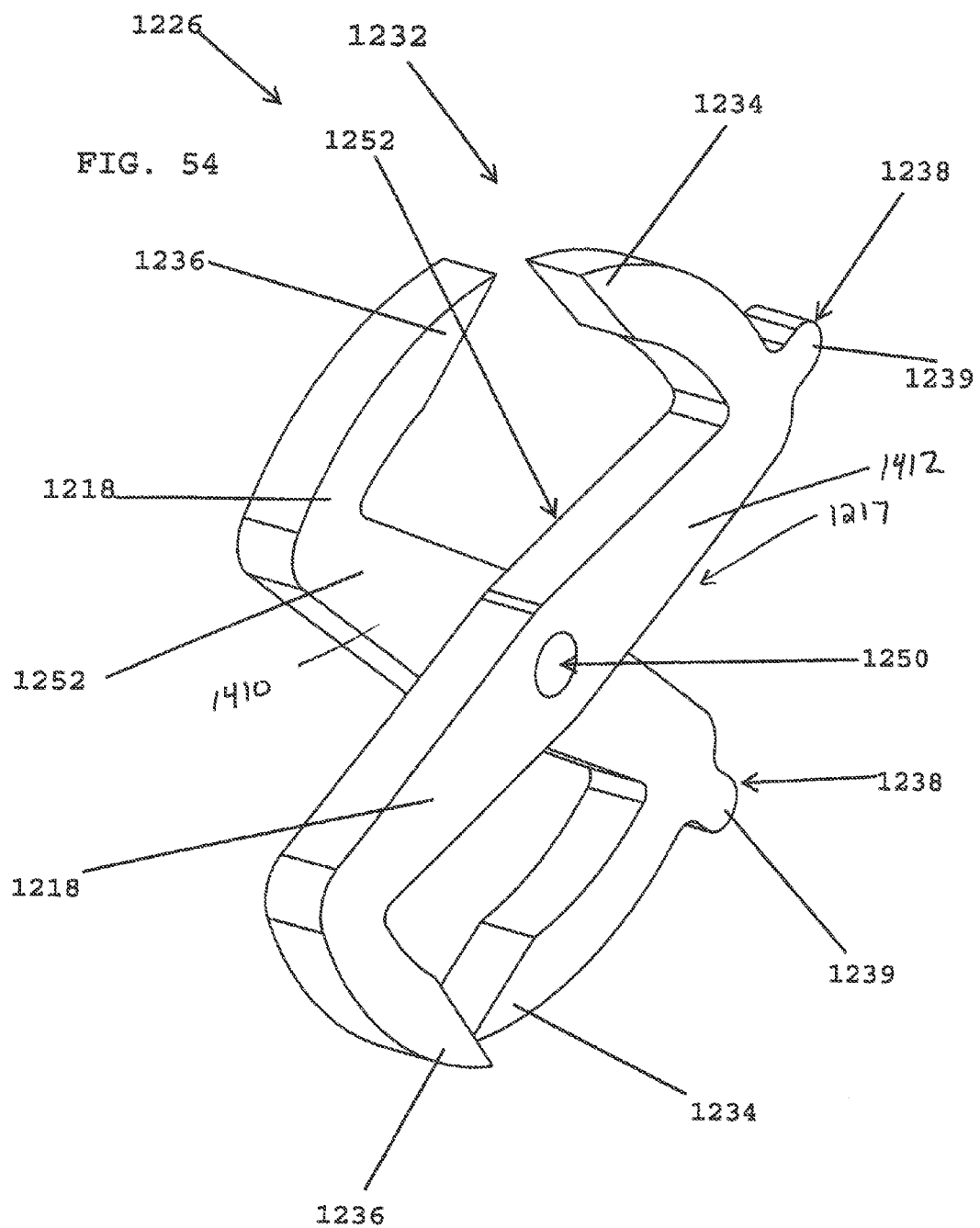
FIG. 54 is a perspective view of the scissor arms of the implant device of FIG. 49 in the securing orientation showing tool engagement portions of the scissor arms.

The scissor anus 1218 each include an elongate base arm 1410 and 1412 with the opposite end portions 1228 and 1229 extending transversely to the elongate base arms 1410 and 1412, as best seen in FIG. 54. An aperture 1250 extends through each base arm portion 1410 and 1412 to be aligned with each other for pivotably receiving the pivot pin 1230 therethrough. As shown in FIGS. 49-54, the elongate base aid 1410 and 1412 and the opposite end portions 1228 and 1229 of the scissor arms 1218 have an "S" shaped configuration 1232. As a result, as the scissor arms 1218 shift to the securing configuration 1226 a first bone penetrating portion 1234 engages one vertebral body 10 and a bone penetrating portion 1236 engages an adjacent vertebral body 10.

As shown best in FIGS. 49, 52 and 54, the scissor arms 1218 can include a tool engagement portion 1238 extending from one of the opposite ends 1228 of the scissor arm 1218 for being directly engaged by an engagement end portion 1416 of a tool 1414, rather than the tool engaging an actuator. In particular, the tool engagement end portion 1238 extends transversely from the surface of the opposite end portion to provide a defined engagement surface to be engaged by the tool. In one aspect, as shown in FIG. 54, the tool engagement portion 1238 can be a small boss 1239 extending from one of the opposite end portions 1228 of the scissor arms 1218; however other configurations, including grooves and pins are contemplated.

As shown in FIGS. 49 and 51, with the scissor arms 1218 in the insertion orientation 1220, the bosses 1239 extending from one of the opposite end portions 1228 of the scissor arms 1218 are positioned adjacent one another to allow both bosses 1239 to be engaged from a single general direction. In this manner, both adjacent bosses 1239 can be readily engaged simultaneously by corresponding engagement end portions 1416 of a single tool 1414 as by an abutting interface 1466 therebetween. Once engaged, the tool 1414 can be operated to apply force on the bosses 1239 extending from the one opposite end 1228 so that the scissor arms 1218 pivot about the pivot in 1230 extending through the apertures 1250 of elongate bases 1410 and 1412 of the scissor arms 1218. Each scissor arms 1218 is pivoted so that the bone penetrating portion 1234 of the one opposite end 1228 pivot toward and penetrate one of the adjacent vertebral bodies and the bone penetrating portion 1236 of the other opposite end 1412 of the scissor arm 1218 pivot toward and penetrate the other adjacent vertebral body. Once the bone penetration portions 1234 and 1236 are driven to their securing position in the corresponding vertebral bodies, the tool is easily withdrawn away from the scissor arms 1218 with the engagement end portion 1416 of the tool 1414 disengaging the boss 1239 at the end 1228 of the scissor arm 1218 without requiring any special disconnection steps for this purpose. As such, the engagement end portions 1416 of the tool 1414 are configured to automatically disengage from abutting engagement with the bosses 1239 of the scissor arms 1218 as the tool 1414 is pulled away from the implant device 1200. As indicated above, both scissor arms 1218 can be engaged and forcefully pivoted about the pivot pin 1230 simultaneously or individually.

As shown in FIGS. 49 and 51, the implant device 1200 is configured to provide access to the tool engagement portions 1238 of the scissor arms 1218. In particular, the outer wall 1400 includes a gap opening 1213 therein extending between the ends 1214 of the spaced center walls 1208 leading to slot opening 1464 between the center walls 1208. The gap opening 1213 allows for the tool 1414 to access the tool engagement. portions 1238 of the scissor arms 1218 positioned between the spaced center walls 1208. As shown in FIG. 49, the scissor arms 1218 can be sized to extend into or beyond the gap opening 1213 with the scissor arms 1218 in the insertion orientation 1220.

As shown in FIG. 51, the pivot pin 1230 can be closer to the adjacent distal ends 1214 of the center wails 1208 than the opposite ends 1406 and 1408 of the center walls 1208. The offset pin 1230 allows for use of larger scissor arms 1218 sized to extend from the opposite ends 1406 and 1408 of the center walls 1208 and into the gap 1213 of the outer wall 1400.

Figure 61:
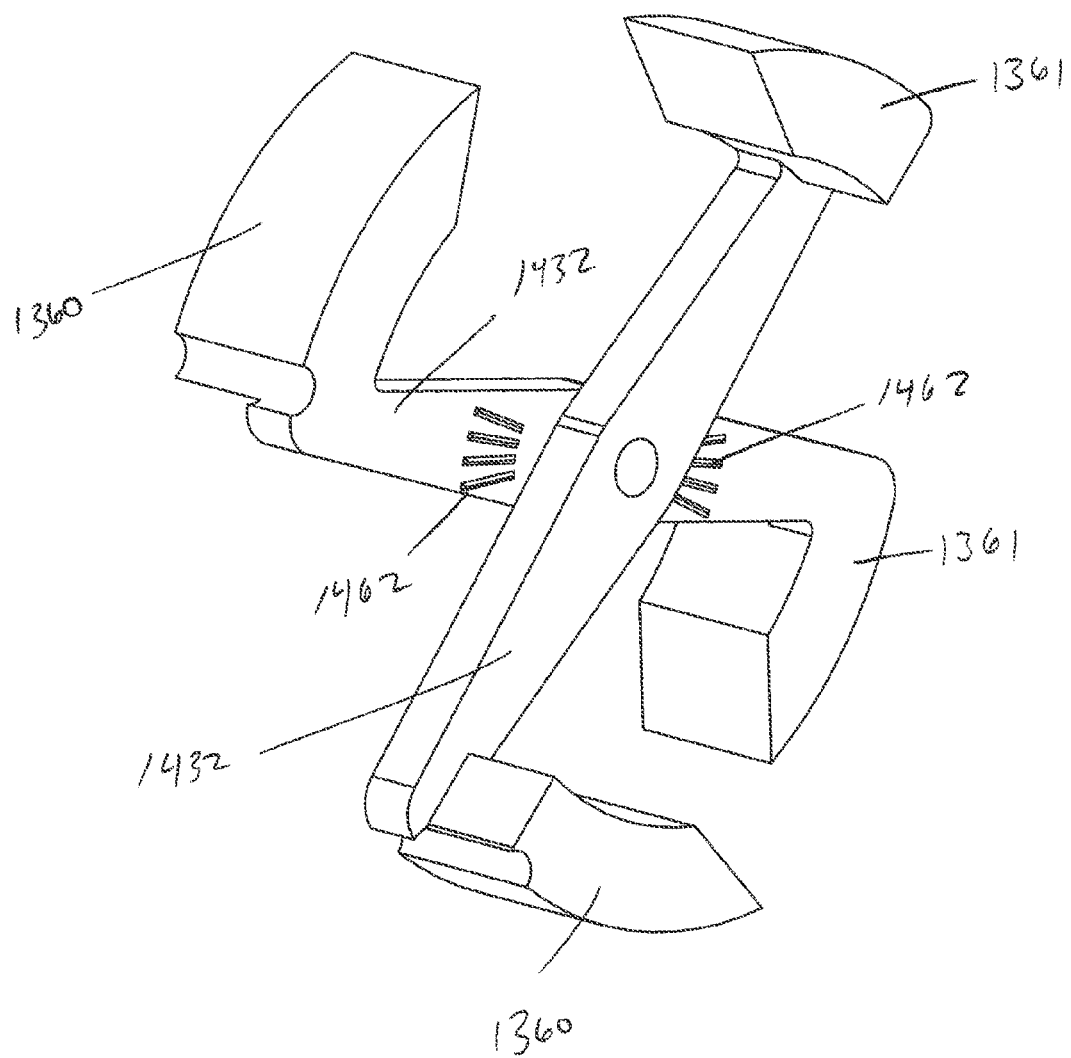
FIG. 61 is a perspective view of the scissor arms of the implant device of FIG. 55 in the securing orientation showing interlocking splines of facing surfaces of the base arm portions of the scissor arms.

As shown in FIG. 54, the inner facing surfaces 1252 of the scissor arms 1218 have a flat configuration to provide low friction engagement therebetween as the scissor arms 1218 are pivoted about the rod 1230. Alternatively, it is contemplated that the facing surfaces 1252 can cooperate with one another, such as via interlocking splines 1462 thereof, as shown in FIG. 61, that are configured to permit rotation of the scissor arms 1218 toward the securing configuration 1226 and resist movement of the scissor arms 1218 away from the securing configuration 1226.

The implant body 1202 can include a stop portion 1240 to limit the rotation of the scissor arms 1218. As shown in FIGS. 49 and 50, the implant body 1202 can include an upper stop member 1242 and a lower stop member 1244 extending between the central wall portions 1208 at an intermediate location therebetween to be positioned to be engaged by the scissor arms 1218 as the scissor arms 1218 are being pivoted to the securing configuration 1226.

As described above, and similar to implants 100 and 200, the implant device 1200 can include features to minimize or mitigate movement of the implant device 1200 after installation. In particular, similar to the implant device can include gripping teeth 1246 along the upper and lower surfaces 1222 and 1224 for engaging the adjacent vertebral bodies 10. Additionally, the scissor 1218 can include a locking mechanism (not shown) to resist migration of the scissor arms 1218 out of the bone of the adjacent vertebral bodies 10.

Referring next to FIGS. 55-60, an alternative implant device 1300 is shown. The following description will focus on the differences between the implant device 1200 and the implant device 1300, with a repeated description of the otherwise similar or identical features generally omitted.

The implant body 1302, as shown in FIGS. 55-59, includes a pair of spaced center walls 1308 and an outer wall 1420 extending about the spaced center walls 1308. The outer wall 1420 and spaced center walls 1308 provide a spaced pair of cavities 1304 extending between adjacent vertebrae 10. In contrast to implant device 1200, the outer wall includes a pair of leading edge walls 1306 and a pair of arcuate sidewalls 1312 extending from outer ends 1316 of the leading edge walls 1306. The central walls 1308 include adjacent proximal ends 1422 and 1424 which extend from inner ends 1310 of the leading edge walls 1306 and adjacent distal ends 1314 connected to trailing ends 1426 and 1428 of the sidewalls 1312.

As shown in FIGS. 55-58, and similar to implant device 1200, the implant device 1300 includes a gap opening 1313 of the outer wall 1420 between adjacent distal ends 1314 of the spaced center walls 1308. In addition, the implant device 1300 includes a second gap opening 1430 of the leading walls 1306 of the outer wall 1420 between adjacent proximal ends 1422 and 1424 of the center walls 1308. The gap openings 1313 and 1430 provide clearance for oversized arcuate bone penetrating ends 1360 and 1361 of the scissor arms 1318 pivotably secured between the center walls 1308.

Figure 60:
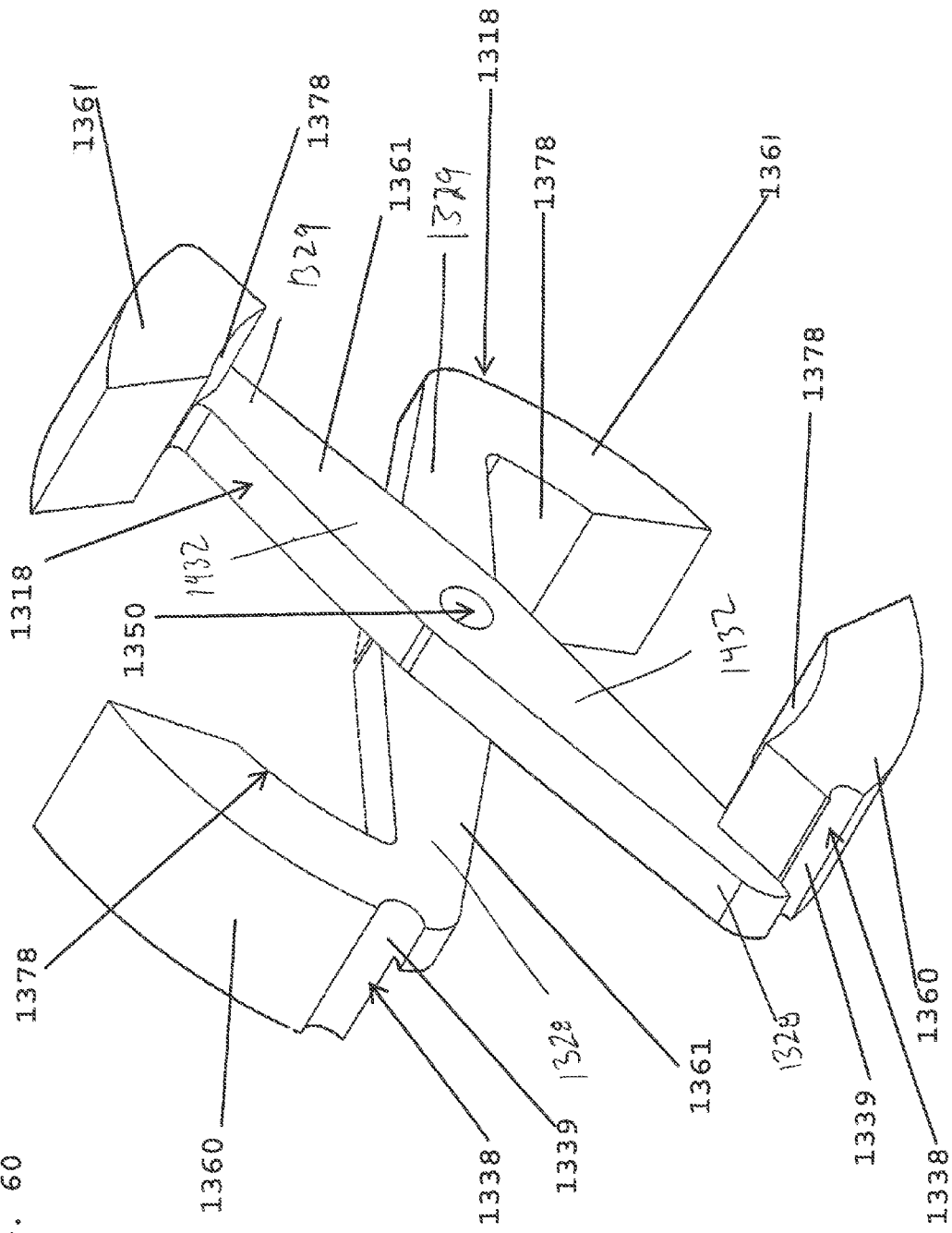
FIG. 60 is a perspective view of the scissor arms of the implant device of FIG. 55 in the securing orientation showing tool engagement portions of the scissor arms.

As with implant device 1200, the scissor arms 1318 include an elongate base arm 1432 with opposite end portions 14 and 1329. As shown in FIG. 60, the oversized ends 1360 and 1361 extend from the opposite end portions 1328 and 1329 and transversely to the elongate base arm 1432. As shown in FIG. 60, the scissor arms 1318 have an shaped configuration 1332 so that as the scissor arms 1318 shift to a securing configuration 1326, a first bone penetrating portion 1334 of one of the oversized ends 1360 engages one vertebral body 10 and a second bone penetrating portion 1336 of the other oversized end 1361 engages an adjacent vertebral body 10.

The bone penetrating portions 1334 and 1336 of the oversized ends 1360 and 1361 of the scissor arms 1318 have a width wider than the width of the base portions 1432 of the scissor arms 1318. By increasing the size of the bone penetrating ends 1334 and 1336 of the scissor arms 1318, the bone penetrating portions 1334 and 1336 embedded in the adjacent vertebral bodies 10 can overcome larger forces which may try and separate the implant body 1302 from the surfaces of the vertebral body 10. In particular, the increased surface area between bone penetrating portions 1334 and 1336 of the oversized ends 1360 and 1361 and the surrounding bone materials provides increased resistance to separation forces between the vertebral bodies 10 and the implant device 1300 anchored therebetween.

The scissor arms 1318 can be formed as a single piece or can be multiple pieces connected together. In particular, the intersection of the elongate base arms 1432 and the opposite ends 1328 and 1329 including oversized bone penetrating portions 1334 and 1336 should be constructed to withstand the stress of piercing a vertebral body 10 with the oversized bone penetrating ends 1334 and 1336.

Figure 55:
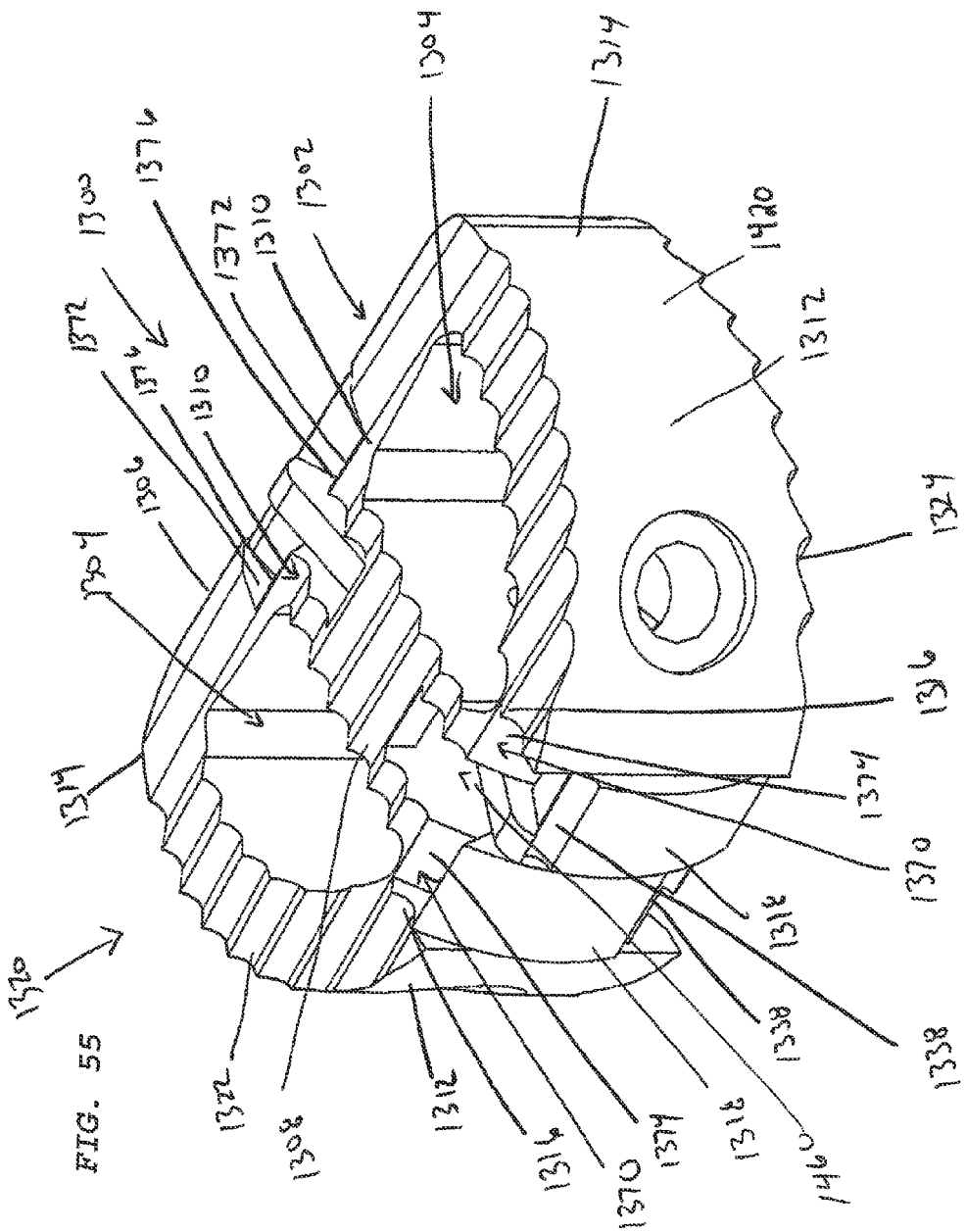
FIG. 55 is a perspective view of an implant, device in accordance with another aspect of the invention showing teeth on upper and lower surfaces of an implant body and scissor arms shifted so that an elongate base arm and enlarged opposite end portions of the scissor arms do not extend beyond the upper and lower surfaces of the implant body in an insertion orientation thereof.
Figure 56:
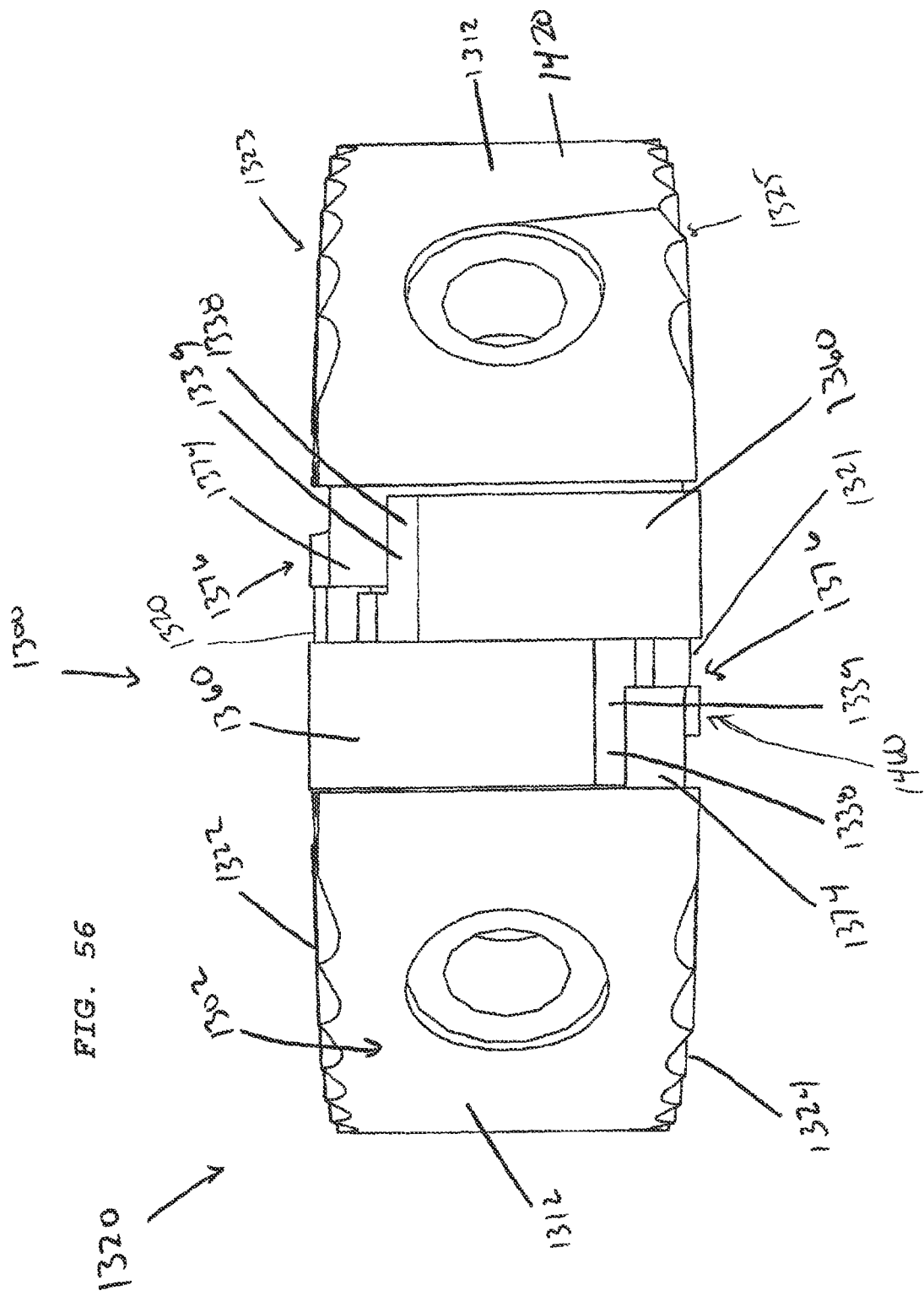
FIG. 56 is a front end elevational view of the implant device of FIG. 55 showing a gap in an outer wall of the implant body for receiving enlarged end portions of the scissor arms in the insertion orientation.
Figure 57:
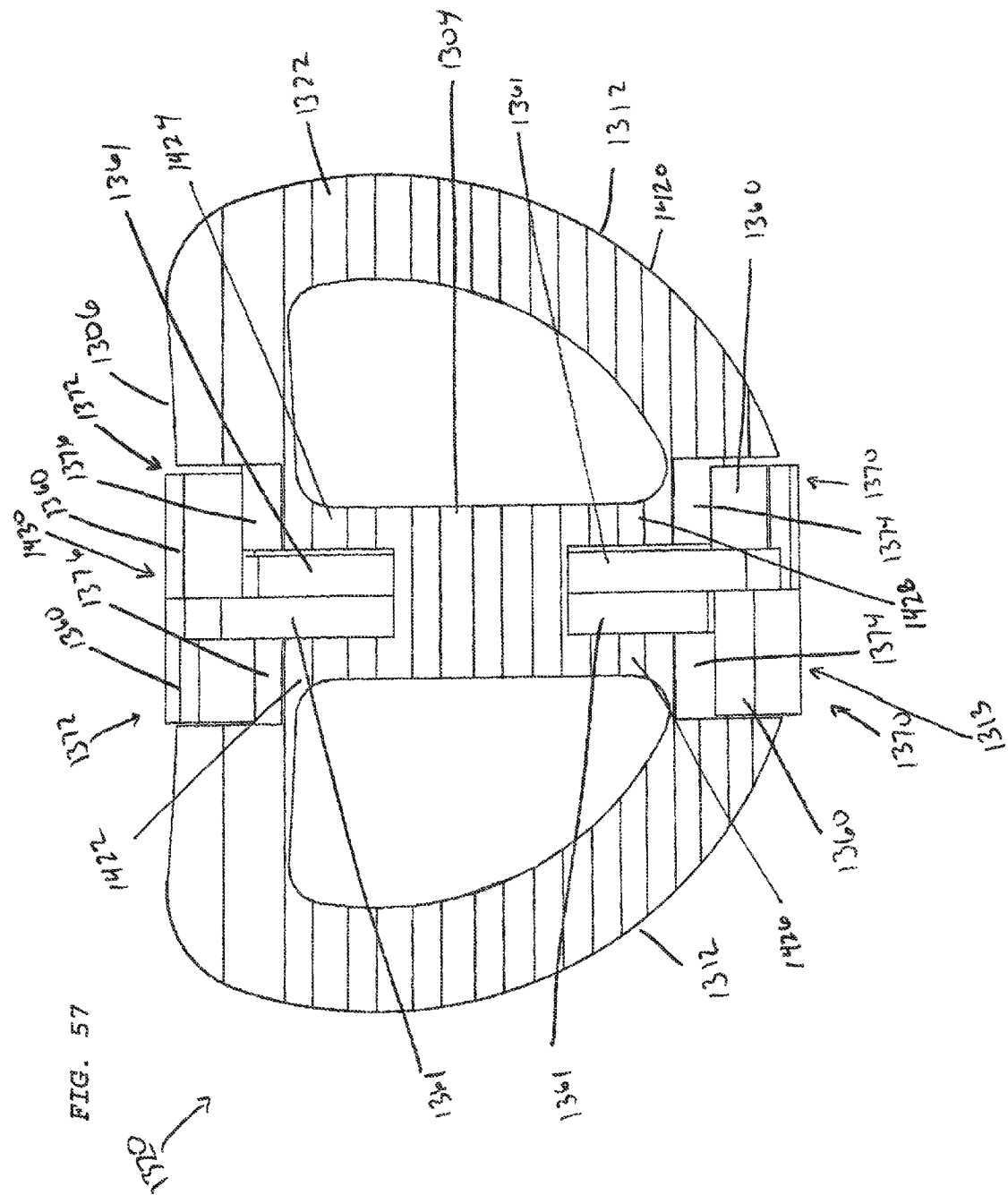
FIG. 57 is a top plan view of the implant device of FIG. 55 showing the gaps of the outer wall along either end of the central wall portions for receiving enlarged end portions of the scissor arms in the insertion orientation.
Figure 58:
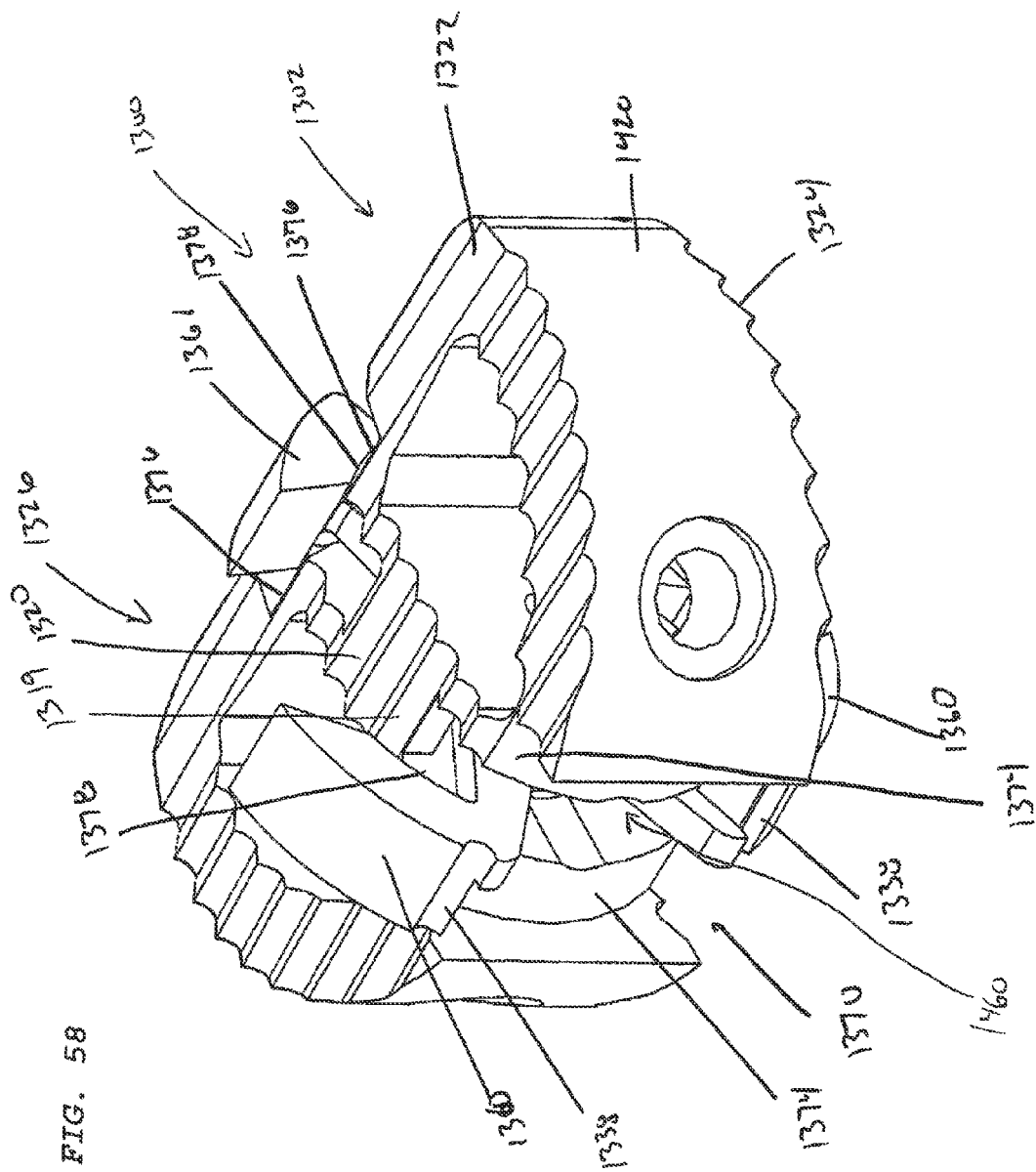
FIG. 58 is a perspective view of the implant device of FIG. 55 showing the scissor arms in a securing orientation.
Figure 59:
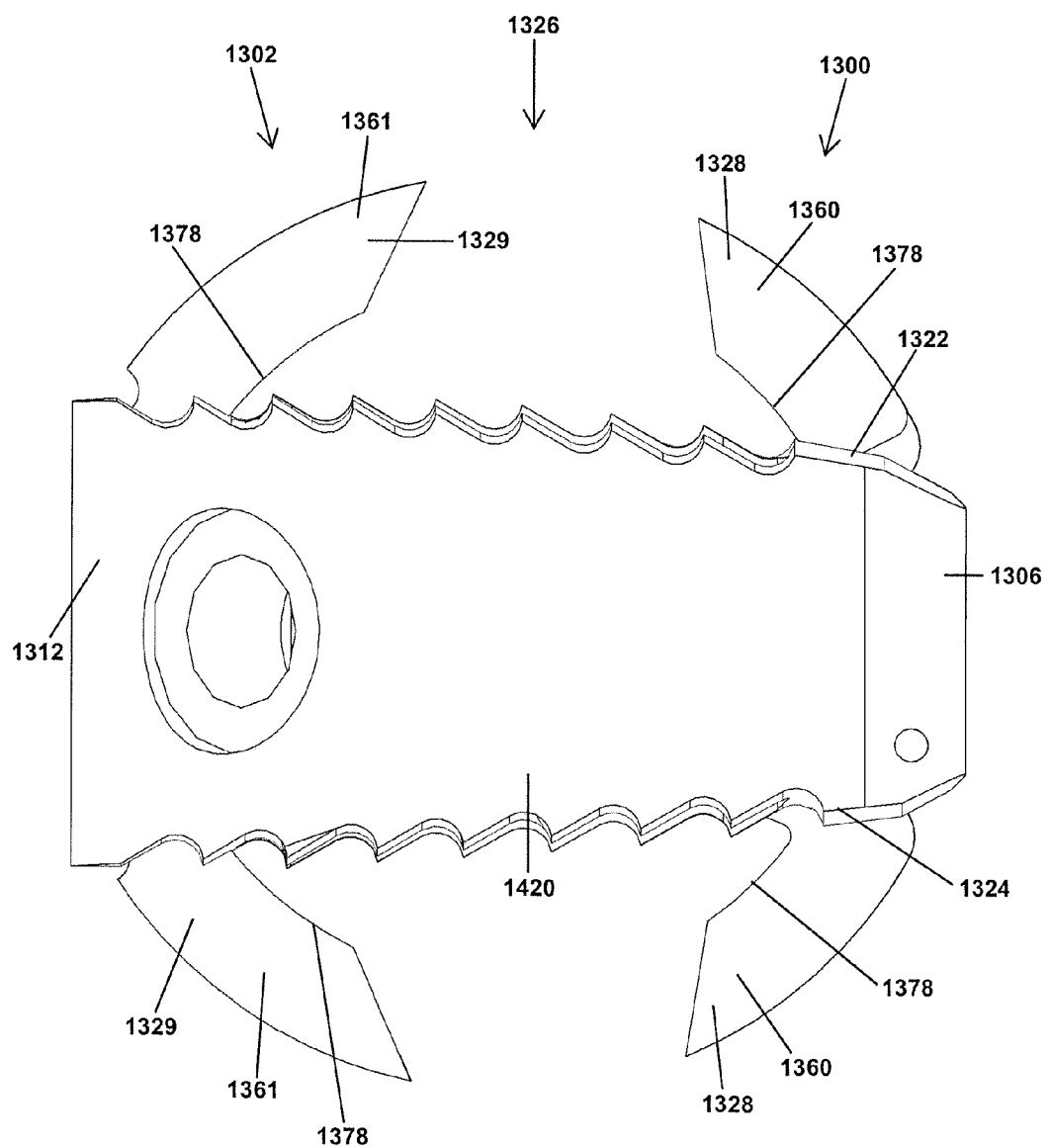
FIG. 59 is a side elevational view of the implant device of FIG. 55 in the securing orientation.

As shown in FIGS. 55-60, and similar to implant device 1200, the center walls 1308 are spaced sufficiently so that a slot opening 1460 is sized to receive the scissor arms 1318 therebetween. The scissor arms 1318 are configured to pivot between an insertion configuration 1320, as shown in FIGS. 55-57, and a securing configuration 1326, as shown in FIGS. 58 and 59. In the insertion configuration 1326, the bone penetrating portions 1334 and 1336 of the scissor arms 1318 are generally positioned between upper and lower surfaces 1322 and 1324 of the implant body 1302. In the securing configuration 1326, the bone penetrating portions 1334 and 1336 of the scissor arms 1318 extend beyond the implant body upper and lower surfaces 1322 and 1324. As shown in FIG. 60, the elongate base arms 1432 of the scissor arms 1318 include a throughbore 1350 for receiving a pivot pin or rod 1330 secured to and extending between the spaced central walls 1308. The scissor arms 1318 are configured to pivot about the pivot pin 1330 between the central wall portions 1308 from the insertion configuration 1320 to the securing configuration 1326.

To accommodate the oversized bone penetrating portions 1334 and 1336 of the scissor arms 1318 in the insertion orientation 1320, the implant body 1302 includes cut out portions 1370 and 1372 of the leading edge wall 1306 and side wall 1312 at the intersection of the side wall 1312 and the central wall 1308. As best shown in FIGS. 55 and 58, the cutout portions 1370 and 1372 include curved wall portions 1374 and 1376. The curved wall portions 1374 and 1376 are configured to correspond to the curvature of a curved underside wall 1378 of the oversized bone penetrating portions 1334 and 1336 to allow for free rotation of the scissor arms 1318 without impedance or interference from the side wall 1312 or leading edge walls 1306.

As with implant device 1200, and as shown best in FIGS. 55, 58 and 60, one of the opposite ends 1328 of the scissors 1318 can include a tool engagement portion 1338 for being directly engaged by an engagement end 1416 of a tool 1414. By directly engaging the tool engagement portion 1338 with the engagement end portion 1416 of the tool 1414 and shifting the tool engagement portion 1338 toward the vertebral body 10 the scissor arms 1318 can be pivoted about the pivot pin 1330 from the insertion configuration 1320 to the securing configuration 1326. As best shown in FIG. 60, the tool engagement portion 1338 includes a rounded groove 1339 into which correspondingly configured engagement end portions 1416 of a tool 1414 fit for pivoting one of the scissor arms 1318. Other configurations of the tool engagement portion 1338, including a squared-off groove or a protruding boss or pin, are also contemplated.

Extending across a generally central area 1319 between the center walls 1308 are upper and lower bridge walls 1320 and 1321. The bridge walls 1320 and 1321 extend along the upper surface 1323 and lower surface 1325 of the implant body 1302. Further, the bridge walls 1320 and 1321 are positioned and configured to act as a stop member to restrict over pivoting of the scissor arms 1318.

Referring next to FIGS. 24-28, an alternative implant device 600 is shown. The following description will focus on the differences between the implant device 100 and the implant device 600, with a repeated description of the otherwise similar or identical features generally omitted.

The implant device 600 includes an implant body 602 and piercing portions 680. The configuration of implant body 602 can include any implant device or artificial disc which is rotatable between adjacent vertebrae, and particularly the implants described in U.S. Patent Application Publication No. 2006/0129238 to Paltzer and U.S. Patent Application Publication No. 2007/0282441 to Stream et al., both of which are hereby incorporated in their entirety herein.

Generally, the implant body 602 includes a leading end 604, a trailing end 606, a tool engagement portion 616 in the form of opposite side slots, lateral surfaces 608 into which the slots of the tool engagement portion are formed, an upper surface 610, a lower surface 612 and gripping portions or teeth 618. More particularly, the lateral surfaces 608, the upper surface 610 and the lower surface 610 extend between the leading end edge 604 and the trailing end edge 606. Adjacent the leading end 604, the lateral surfaces 608 extend between the upper and lower surfaces 610 and 612. However, as shown in FIGS. 24-28, the lateral surfaces 608 include spaced surface portions positioned adjacent the upper and lower surfaces 610 and 612 and on either side of the tool engagement slot 616. Gripping portions or teeth 618 are formed on the upper and lower surfaces 610 and 612 and extend outwardly therefrom. As shown in FIG. 24, the tool engagement portion 616 extends from the trailing end 606 along the lateral surfaces 608 of the implant body 602.

As shown in FIGS. 24-28, the implant body 602 is configured to be rotated between the adjacent vertebrae 10 so that the upper and lower surface 610 and 612 engage the adjacent vertebral bodies 10. In one embodiment, the implant body 602 does not include a central cavity as found in implant device 100. In the illustrated embodiment as shown in FIGS. 24-28, the implant body 602 defines a central cavity 622 positioned between the leading end 604, trailing end 606 and lateral surfaces 608 which preferably extends between the upper surface 610 and the lower surface 612. The implant body 602 also includes an axis 643 which is defined by the length 603 of the implant body 602.

Figure 25:
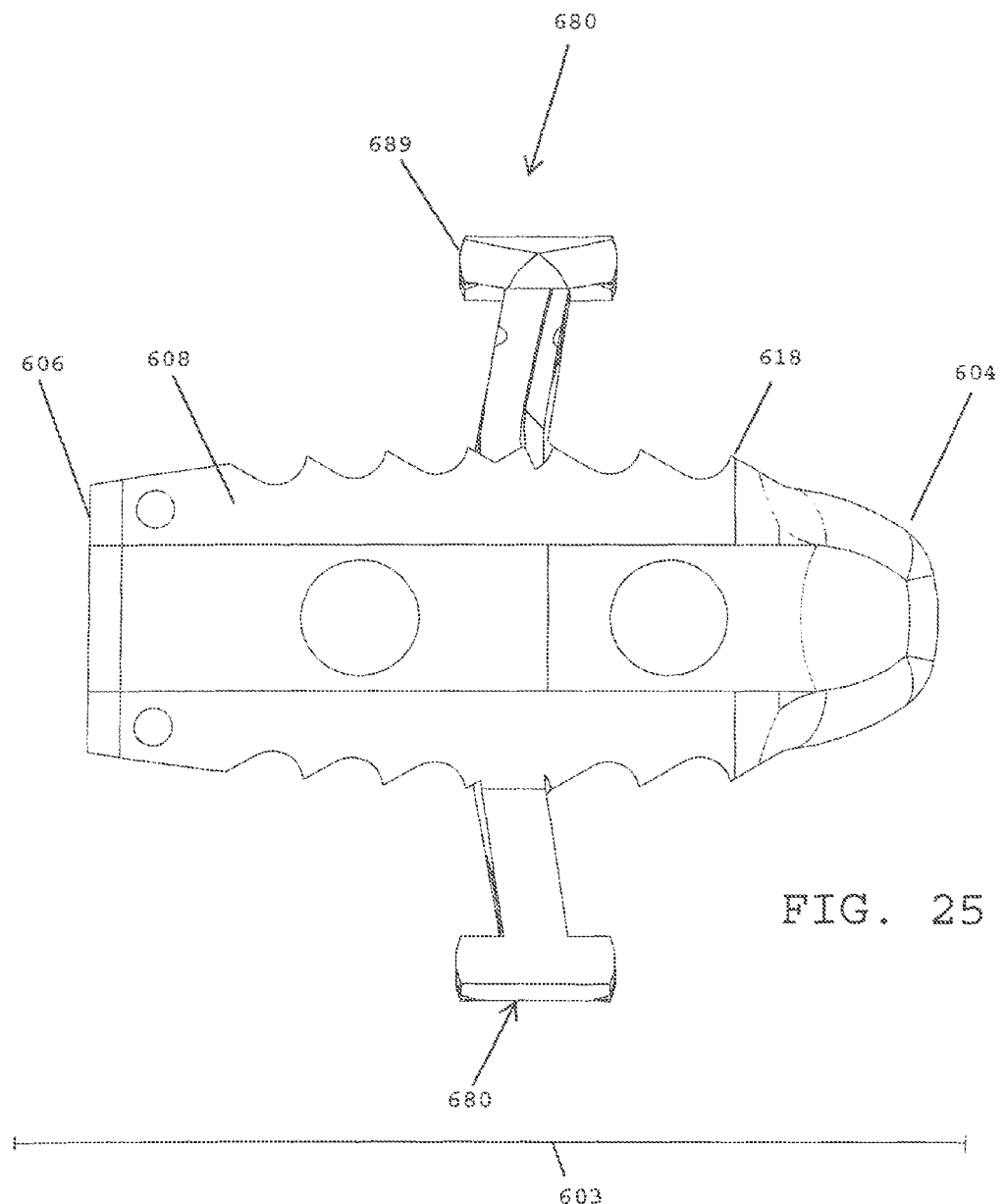
FIG. 25 is a side view of the implant device of FIG. 24 showing the piercing portions extending from an upper surface and a lower surface of the implant body.

As shown in FIGS. 24 and 25, the leading end 604 includes a tapered, contoured surface configured to ease insertion of the implant device 600 between adjacent vertebrae.

In one embodiment, the lateral surfaces 608 of the implant body 602 have a convex configuration to ease insertion and rotation of the implant device 600 between the adjacent vertebrae. The convex lateral surfaces 608 reduce the torque on the tool required to begin rotation of the implant device 600 between the vertebral bodies 10 toward the secured orientation.

Figure 26:
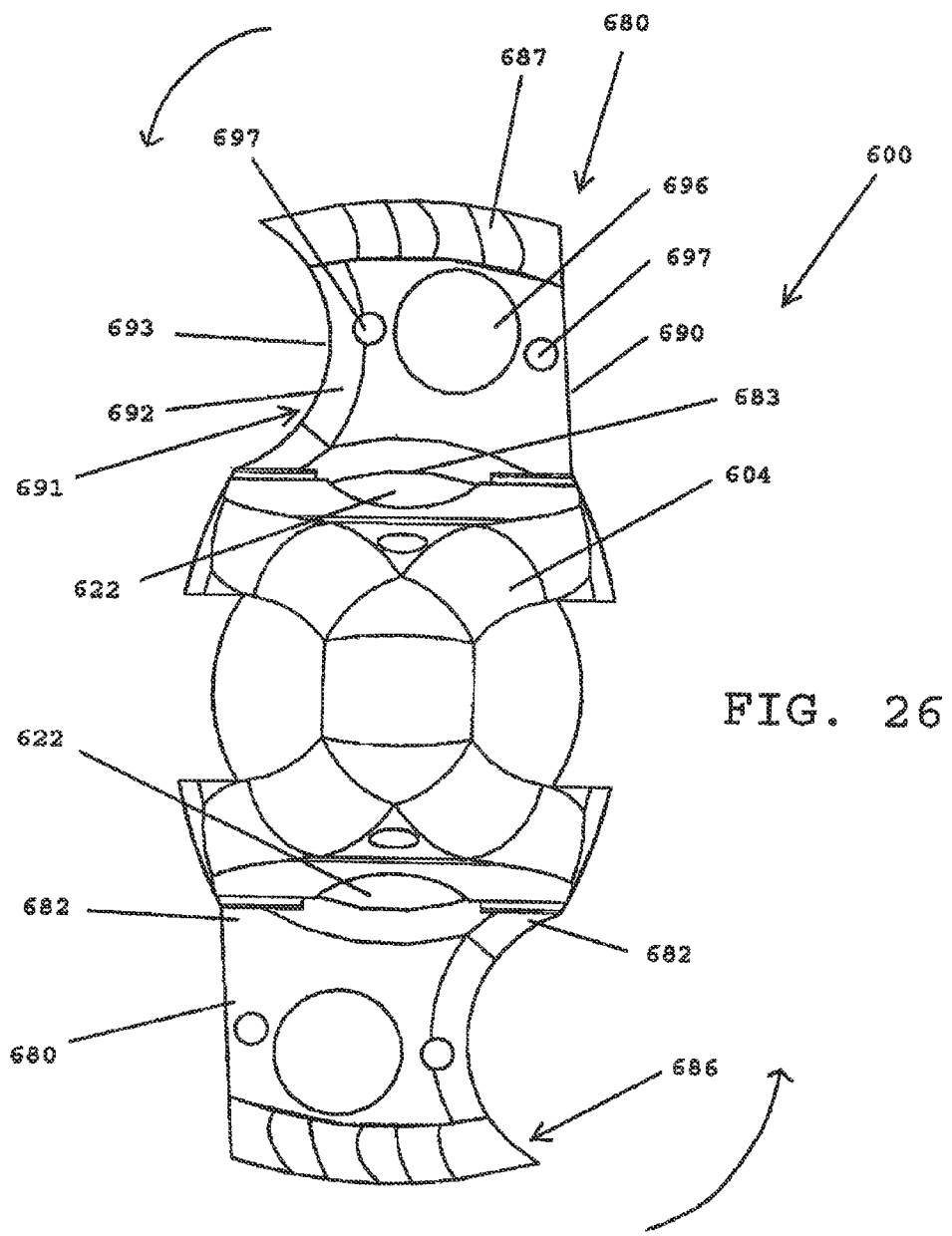
FIG. 26 is an end view of the leading edge of the implant device of FIG. 24 showing a leading edge of the implant body and a penetrating edge and a blunt edge of the piercing portions extending from the implant body.
Figure 27:
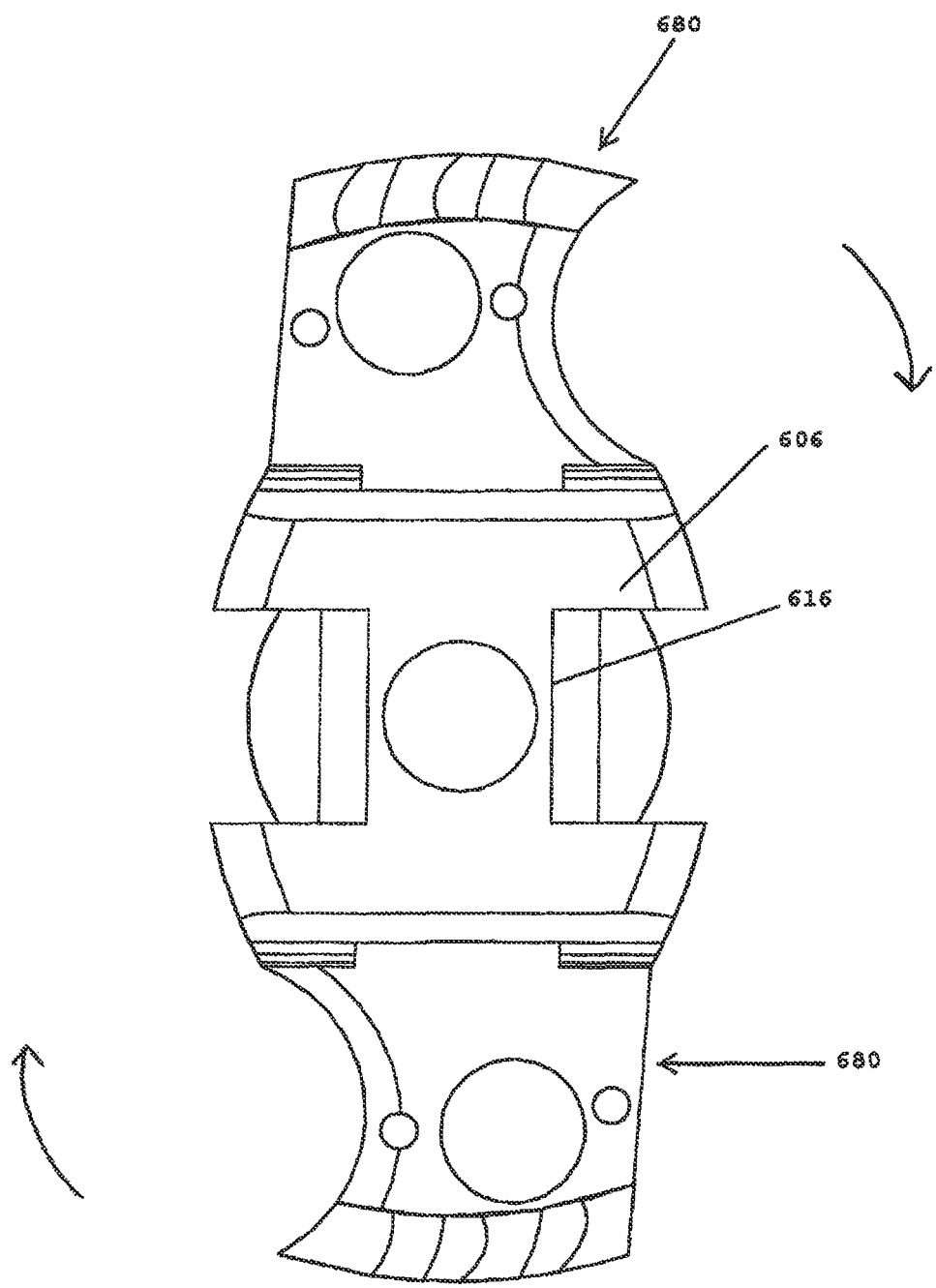
FIG. 27 is an end view of the implant device of FIG. 24 showing a tool engagement portion of a trailing edge of the implant body.
Figure 28:
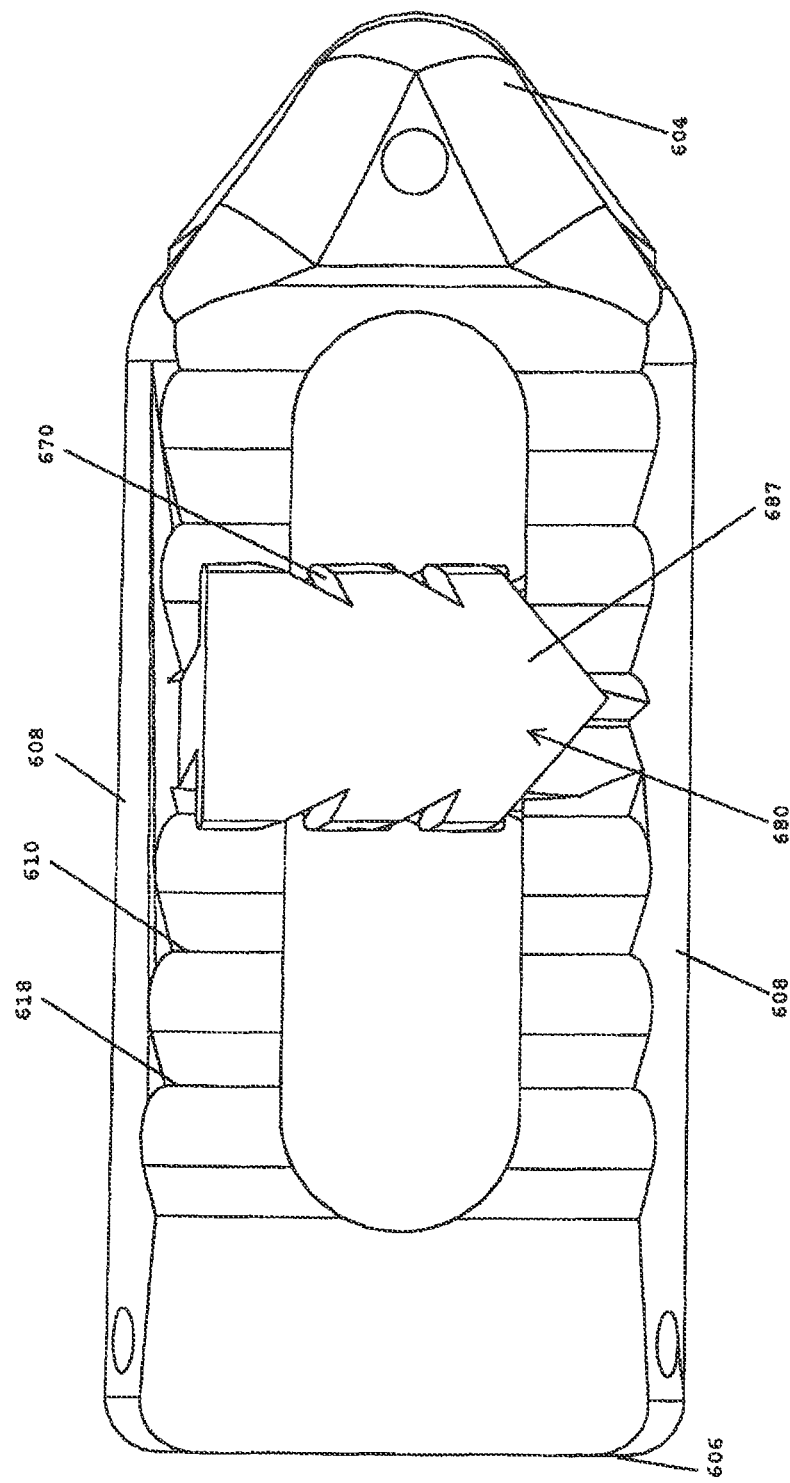
FIG. 28 is a top plan view of the implant device of FIG. 24 showing the piercing portion extending across the central cavity.

The implant device 600 further includes at least one piercing portion 680. Preferably, the implant device includes at least two piercing portions 680, such as shown in FIGS. 24 and 27. As shown in FIGS. 24-28, the implant device 600 includes at least one piercing portion 680 extending from the upper surface 610 and at least one piercing portion 680 extending from the lower surface 612 to engage each of the adjacent vertebral bodies 10. As best shown in FIGS. 26 and 27, the piercing portions 680 are oriented so they both penetrate the adjacent vertebral bodies 10 as the implant body 602 is rotated in a predetermined rotary direction, such as clockwise as shown in FIG. 27.

The implant device 600 is configured to be inserted between adjacent vertebra 10 with the lateral surfaces 608 in contact with the vertebral bodies 10, while the upper and lower surfaces 610 and 612 extending between the vertebral bodies 10 and the piercing portions 680 extending from the upper and lower surfaces 610 and 612 are not engaged with the vertebral bodies. The piercing portions 680 are configured to extend between the lateral surfaces 608 and away from the upper and lower surfaces 610 and 612 to provide adequate engagement with the vertebral bodies 10 in the securing orientation to resist separation between the implant body 602 and the vertebral bodies. Additionally, the piercing portions 680 are sized to not extend beyond the vertebral bodies 10 when in the insertion orientation between the adjacent vertebrae.

After the implant device 600 is positioned between the adjacent vertebrae, the implant body 602 is engaged by a tool at the tool engagement portion 616 and the entire implant device 600 is rotated about the axis 643 so that the piercing portions 680 penetrate the adjacent vertebrae and the upper and lower surfaces 610, 612 are in engagement with the adjacent vertebral bodies 10. More particularly, as the implant body 602 is rotated about the axis 643, the piercing portion 680 and the teeth 618 adjacent a leading edge 691 of the piercing portion 680 engage the vertebral bodies prior to the teeth 618 adjacent a flat end surface 690 opposite the penetrating edge 691. The piercing portions 680 each include a cutting wall portion 682 and a cutting ledge portion 686. As shown in FIG. 25, the cutting wall portion 682 of the piercing portion 680 extends generally normal to the axis 643 of the implant body 602. The cutting ledge portion 686 extends transversely to the cutting wall portion 686 from a distal end of the cutting wall portion 682. As shown in FIG. 24, the cutting wall portion 682 of each piercing portions 680 is connected to one of the upper and lower surfaces 610 and 612, and extends from one of the lateral surfaces 608, across the central cavity 622 and to the other lateral surface 608. In one embodiment, as shown in FIG. 24, the cutting wall portion 682 includes a rounded lower are portion 683 extending across the central cavity 622.

The piercing portion 680 further includes the penetrating leading edge 691 of the cutting wall portion 682 extending from one of the lateral surfaces 608 to the cutting ledge portion 686. Opposite the penetrating leading edge 691 is the flat end surface 690 extending from the other lateral surface 608 to the cutting ledge portion 686. Additionally, the cutting wall portion 682 includes a pair of opposing sidewall surfaces 694 extending the penetrating edge 691 and the flat end surface 690. The penetrating edge 691 is configured to ease penetration of the vertebral body 10 as the implant device 600 is rotated between the adjacent vertebrae. Preferably, the penetrating edge 691 can include a tapered configuration 692 as shown in FIG. 27. Further, it is preferable that the penetrating edge 691 is configured to ease penetration, such as by having a concave configuration 692, as shown in FIG. 27. In a further preferable embodiment, the penetrating edge 691 includes a sharpened edge to facilitate insertion into the vertebral body 10. The flat end surface 690, as shown in FIGS. 26 and 27, is configured to provide a blunt engagement with the vertebral bodies so that the implant body 602 is rotatable toward the securing orientation by rotating the implant body 602 in a specified direction.

As shown in FIGS. 24, 26, 27, the cutting ledge portion 686 of the piercing portion 680 includes a shelf 687 configured to resemble an arrowhead and extending generally normal to the penetrating edge 691 and generally parallel to the axis 643 of the implant device 600. In one embodiment, the shelf 687 can extend outwardly toward the leading end 604 of the implant body 602. In an alternative embodiment, the shelf 687 extends outwardly toward the trailing end 606 of the implant body 600 or, as shown in FIG. 25, toward both the leading end 604 and the trailing end 606. The shelf 687 provides additional engagement with the vertebral bodies and acts to further resist separation of the vertebral bodies and the implant device 600.

Finally, the shelf side 689 may be rounded, flat or tapered. In a preferable embodiment the shelf sides 689 have a convex surface configuration, as shown in FIGS. 24, 25. In one embodiment, as shown in FIG. 24, the shelf 687 can include a locking mechanism 670 to resist movement of the shelf 687 after being shifted into the vertebral body 10. As shown in FIG. 24, the locking mechanism 670 of the arrow-head shaped shelf 687 can include cutout portions configured to resist migration or back out of the implant device 600 from between adjacent vertebrae.

Preferably, the piercing portions 680 are configured to be generally confined between the lateral surfaces 608 and the leading and trailing ends 604 and 606 of the implant body 602, as shown in FIGS. 26 and 27, so as to not engage the vertebral bodies 10 with the implant body 602 in the insertion orientation.

The piercing portions 680 can be further secured within the vertebral bodies 10 by a securing member 601 as shown in phantom in FIG. 24. The securing member is configured to extend through the vertebral body 10 and a securing throughbore 696 of the cutting wall portion 682 of the piercing portion 680. Preferably, the securing member extends generally parallel to the axis 643. As shown in FIGS. 26, 27 and discussed above, the securing throughbore 696 extends from one sidewall surface 694 of the cutting wall portion 682 of the piercing portion 680 to the other sidewall surface 694, and is generally centrally located intermediate the flat end surface 690 and the piercing edge 691.

In one embodiment, the piercing portion 680 further includes at least one small throughbores 697. The small throughbores 697 are preferably located adjacent the securing throughbore 696. In one embodiment, the small throughbores 697 and securing throughbore 696 each define an axis that extends parallel to the shelf 687. In a preferred embodiment, the piercing portion 680 includes at least one small throughbore 697 between the flat end surface 690 and the securing throughbore 696 and at least one small throughbore 697 between the penetrating edge 691 and the securing throughbore 697, as shown in FIGS. 24, 26 and 27.

The small throughbores 697 can be used to house additional, smaller securing members. Alternatively, the small throughbores 697 can be configured to accept radiographic markers therein to assist in insertion of the securing member within, the securing throughbore 696. Additionally, the small throughbores 697 can be configured to permit bone growth therethrough, and may be configured to accept bone growth promoting material therein.

Figure 30:
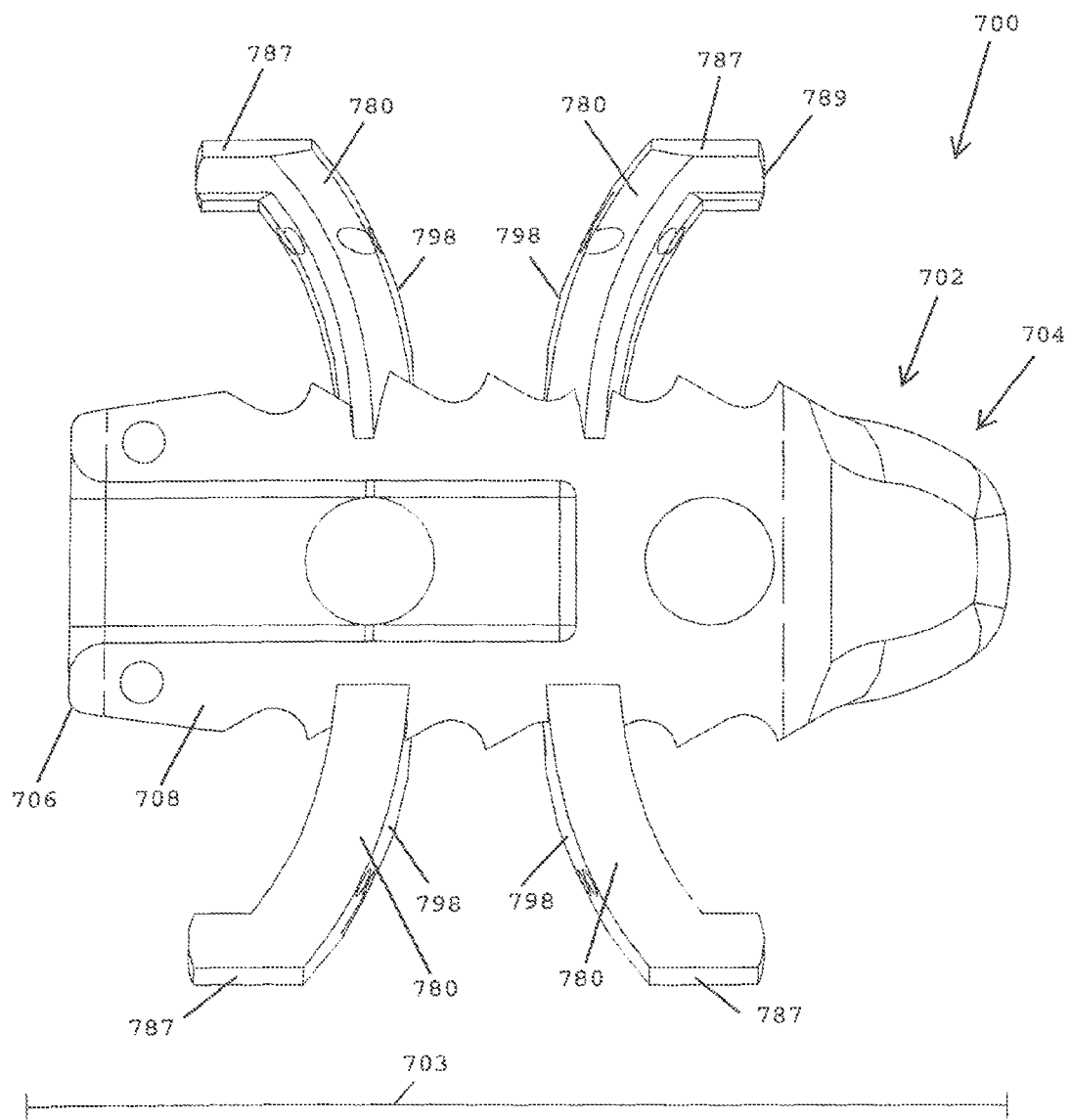
FIG. 30 is a side view of the implant device of FIG. 29 showing the piercing portions extending from an upper surface and a lower surface of the implant body.
Figure 31:
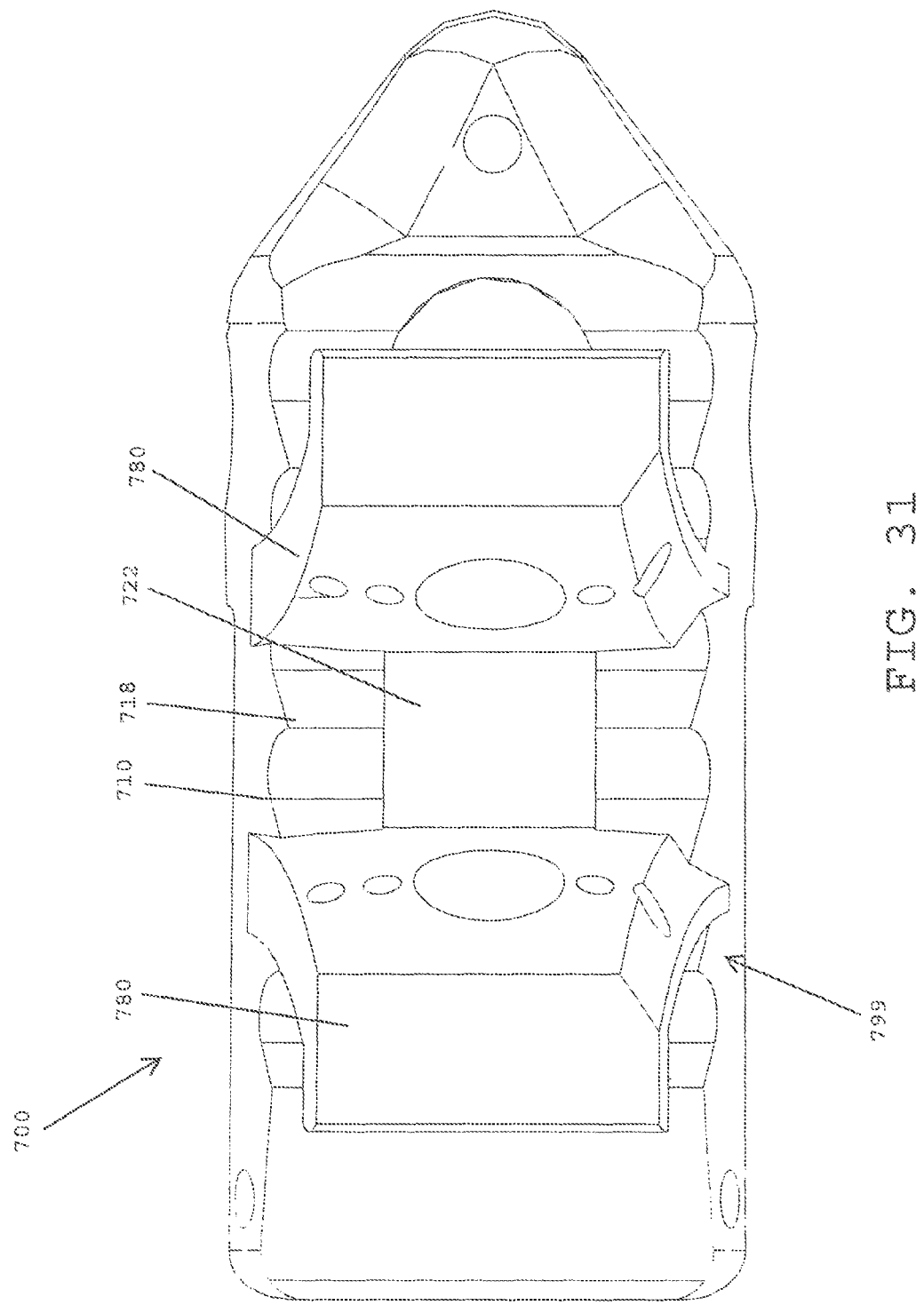
FIG. 31 is a top plan view of the implant device of FIG. 29 showing the piercing portion extending across the central cavity.
Figure 32:
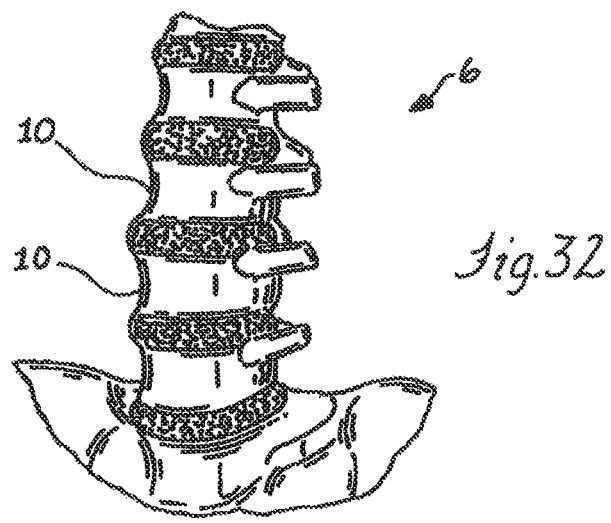
FIG. 32 is a perspective view of a spine.

Referring next to FIGS. 29-31, an alternative implant device 700 is shown. The following description will focus on the differences between the implant device 600 and the implant device 700, with a repeated description of the otherwise similar or identical features generally omitted.

The implant device 700, as shown in FIG. 29, includes two piercing portions 780 extending from the upper surface 710 and two piercing portions 780 extending from the lower surface 712. The piercing portions 780 include a curved configuration 798 such that the piercing portions 780 extend away from the upper and lower surfaces 710 and 712 and toward one of the leading and trailing ends 704 and 706. As shown in FIG. 29, the piercing portions 780 adjacent the leading end 704 extend toward the leading end 704 and the piercing portions 780 adjacent the trailing end 706 extend toward the trailing end 706. It is also contemplated that the piercing portions 780 include a curved configuration 798 and extend in the same direction from the implant body 702, or, alternatively, that the piercing portions 780 would extend toward the central point of the implant body 702 along the axis 743.

By having at least two piercing portions 780 to extend in different directions, the implant device 700 is more secure between the adjacent vertebrae 10 and is able to better resist explantation. The degree of curvature of the curved portion 798 is configured to provide a stable interface between the piercing portion 780 and the vertebral body 10 and to secure the implant device 700 between the adjacent vertebrae.

Additionally, the piercing portion 780 of the implant device 700, as shown in FIGS. 29, 31, includes a piercing edge 791 which is configured to include a convex configuration 799 to ease insertion into the vertebral body 10. In more detail, by configuring the piercing edge 791 so that the vertebral body 10 is first engaged by a small portion of the piercing edge 791, less torque is required to initially penetrate the vertebral body 10 than if the entire piercing edge 791 engages the vertebral body 10 at once. After the vertebral body 10 is initially penetrated, the convex configuration 799 of the piercing edge 791 provides for a gradual increase in the amount of the piercing edge 791 penetrating the vertebral body until the entire piercing edge 791 is engaging the vertebral body 10.

As best shown in FIGS. 29 and 30, and in contrast to implant device 600, the shelf 787 of each of the piercing portions 780 extends only toward the closer of the leading edge 704 and trailing end 706, similar to the curved configuration 798 of the piercing portions 780. Referring next to FIGS. 39-43, an alternative implant device 800 is shown. The following description will focus on the differences between the implant device 800 and the implant devices 600 and 700, with a repeated description of the otherwise similar or identical features generally omitted.

As with implant devices 600 and 700, the implant body 802 includes a leading end 804 for being initially inserted between adjacent vertebral bodies 10. A trailing end 806 opposite the leading end 804 includes a tool engagement portion 816 for being engaged by an engagement end portion 1416 of a tool 1414 for inserting the implant body 802 between the adjacent vertebrae 10 and rotating the implant body 802 between the adjacent vertebrae 10 from the insertion orientation to the securing orientation. The leading end 804 and trailing end 806 are separated by a distance 803 which defines the longitudinal axis 843 of the implant body 802.

A pair of lateral surface 808 extends between the leading end 804 and trailing end 806 and each include a generally smooth surface 807 which face the vertebral bodies 10 during insertion with the implant body 802 in the insertion orientation. The smooth surface 807 of the lateral edges 808 provides low friction engagement when shifting the implant body 802 between the vertebral bodies 10 during insertion and minimizes any abrasion or alteration of the surface of the vertebral bodies 10 by the implant body 802. As shown in FIGS. 39-43, the tool engagement portions 816 include slots formed in the lateral surfaces 808 of the implant body 802.

An upper surface an and opposing lower surface 812 extend between the lateral surfaces 808 and between the leading end 804 and trailing end 806. The upper and lower surfaces 810 and 812 include gripping portions or teeth 818 for engaging the vertebral bodies 10 after the implant body 802 has been shifted to the securing orientation.

As shown in FIGS. 39-43, the implant device 800 includes four piercing or anchoring portions 880 extending from each of the upper surface 810 and lower surface 812 of the implant body. As shown in FIG. 39, the anchoring portions 880 are fins 881. As with the implant device 700, the fins 881 include a curved configuration 883 such that the piercing portions 880 extend outwardly from the upper or lower surface 810 and 812 and toward one of the leading end 804 and trailing end 806 of the implant body 802. As shown in FIGS. 39-43, the implant body 802 includes piercing portions 880 positioned adjacent the trailing end 806 and the leading end 804, with the piercing portions 880 positioned adjacent the leading end 804 curved toward the leading end 804 and away from the piercing portions 880 positioned adjacent the trailing end 806. Similarly, the piercing portions 880 positioned adjacent the trailing end 806 are curved toward the trailing end 806 and away from the piercing portions 880 positioned adjacent the leading end 804. As can be seen in FIG. 39, the distal end 886 of the fins 881 each include a rounded edge portion 887, rather than a shelf as with implant devices 600 and 700, to reduce the overall size of the fins 881 as the fins 881 penetrate the vertebral bodies 10.

As shown in FIGS. 39-43, similar to implants 600 and 700, each fin 881 includes a tapered leading edge 888 for initially penetrating a vertebral body as the implant device 800 is rotated in a first direction about the longitudinal axis 8433. Opposite the tapered edge 888, the fins 881 include a flat surface 889 for resisting rotation of the implant device 800 in a second direction opposite the first direction.

Figure 42:
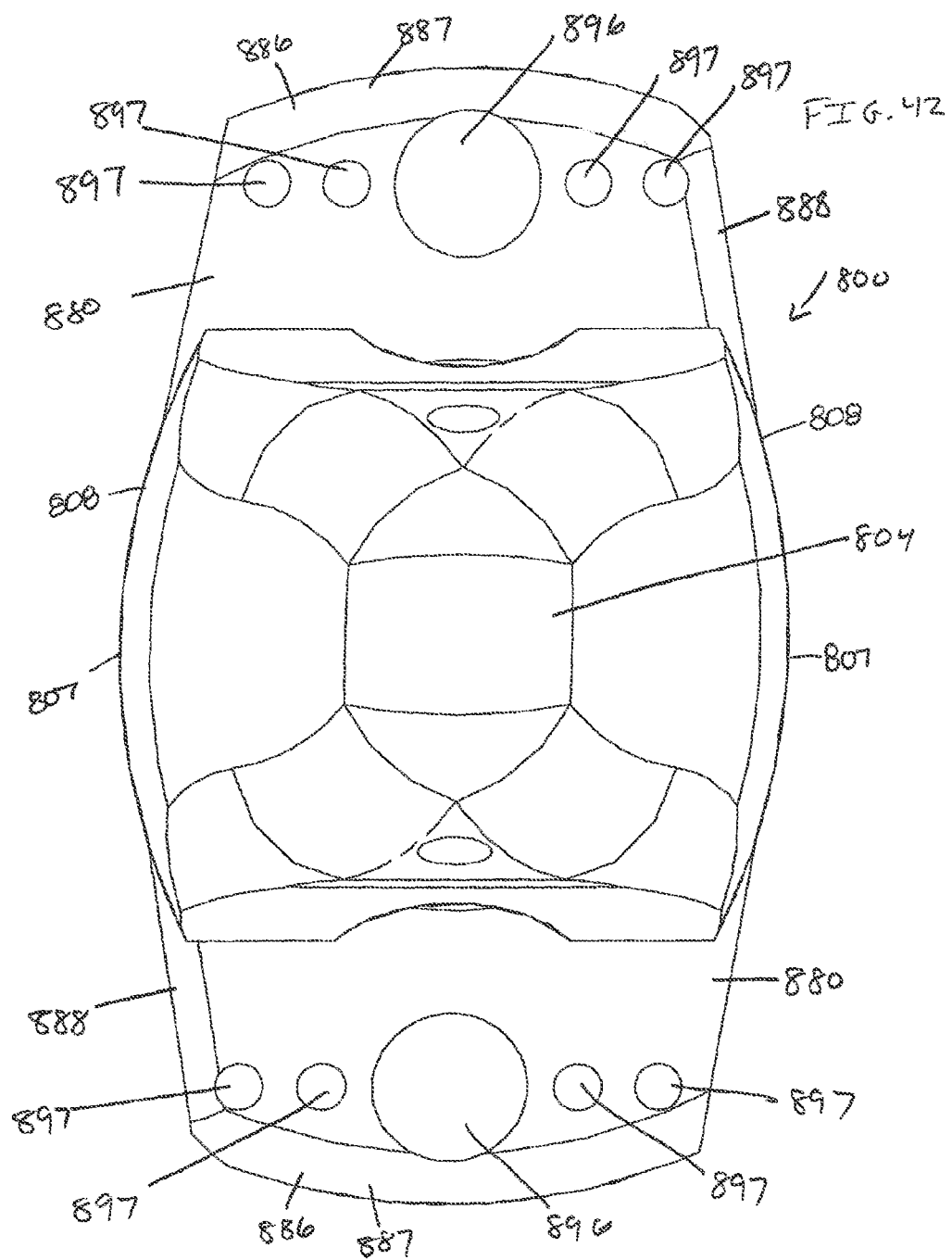
FIG. 42 is a front end elevational view of the implant device of FIG. 39.
Figure 43:
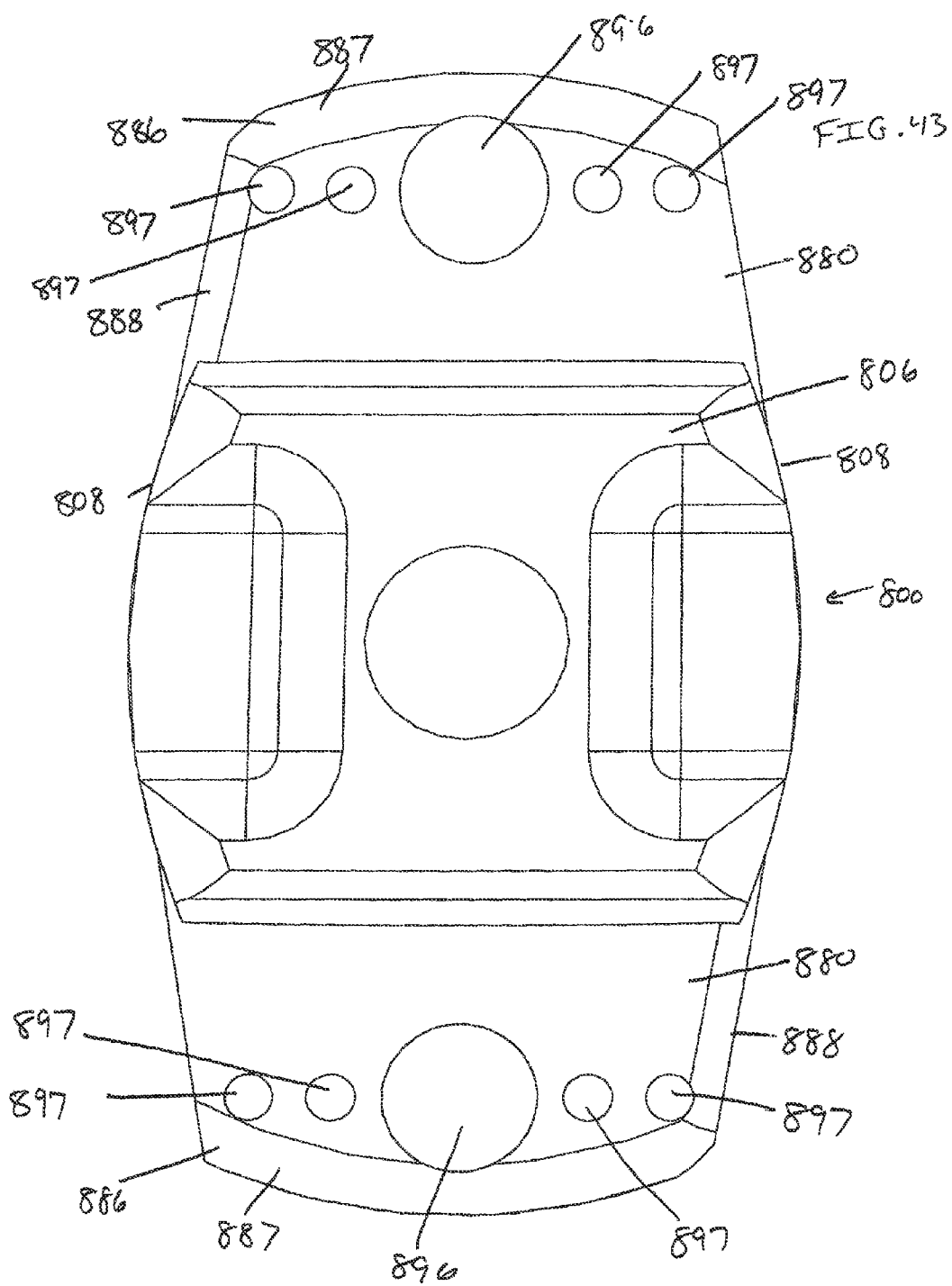
FIG. 43 is a back end elevational view of the implant device of FIG. 39.

As shown in FIGS. 42 and 43, and similar to implants 600 and 700, the fins 881 each include a securing throughbore 896 for receiving a securing member therein for further resisting rotation of the implant device 800 after the fins 881 penetrate the adjacent vertebral bodies 10. Exemplary securing members include pedicle screws, which pierce the vertebral body 10 and extend generally parallel to the face of the vertebral body 10. Further, as shown in FIGS. 42 and 43, the fins 881 each include two smaller throughbores 897 on either side of the securing throughbore 896. The smaller throughbores 897 can be configured to receive material therein, such as securing members, radiological markers or bone graft material.

Additionally, as with implant devices 600 and 700, the fins 881 are configured to be generally confined between the lateral edges 808 of the implant body 802 so as to minimize any contact between the fins 881 and the adjacent vertebral bodies 10 during initial insertion of the implant device 800 prior to rotation. More particularly, the fins 881 are generally confined between the lateral surfaces 808 and the leading and trailing ends 804 and 806 so that, in the insertion orientation, the fins 881 do not engage the adjacent vertebral bodies 10.

Similar to implants 600 and 700, the teeth 818 of the implant body 802 includes two rows of gripping teeth 819 and 821 spaced from one another by a central cavity 822. As with implants 600 and 700, the fins 881 span across the central cavity 822.

As with implant device 700, as the implant body 802 is rotated between the vertebral bodies 10, a first set of teeth 819 and the fins 881 will initially engage the vertebral surface. Depending on the configuration of the fins 881, the first set of teeth 819 and the fins 881 may engage the vertebral body 10 simultaneously or one may engage the vertebral body before the other. As the implant body 802 is rotated, the teeth 819 frictionally engage the vertebral bodies 10 to resist lateral movement of the implant device 800 while the fins 881 penetrate the vertebral bodies 10 to secure the implant device 800 in place. The implant body 802 is rotated until the second set of teeth 821 frictionally engages the vertebral body to further resist movement of the implant device 800.

Further, as with implants 600 and 700, implant 800 can include a solid implant body 802 which does not include a cavity.

Referring next to FIGS. 44-48, an alternative implant device 900 is shown. The following description will focus on the differences between the implant device 900 and the implant devices 600, 700 and 800, with a repeated description of the otherwise similar or identical features generally omitted.

Figure 63:
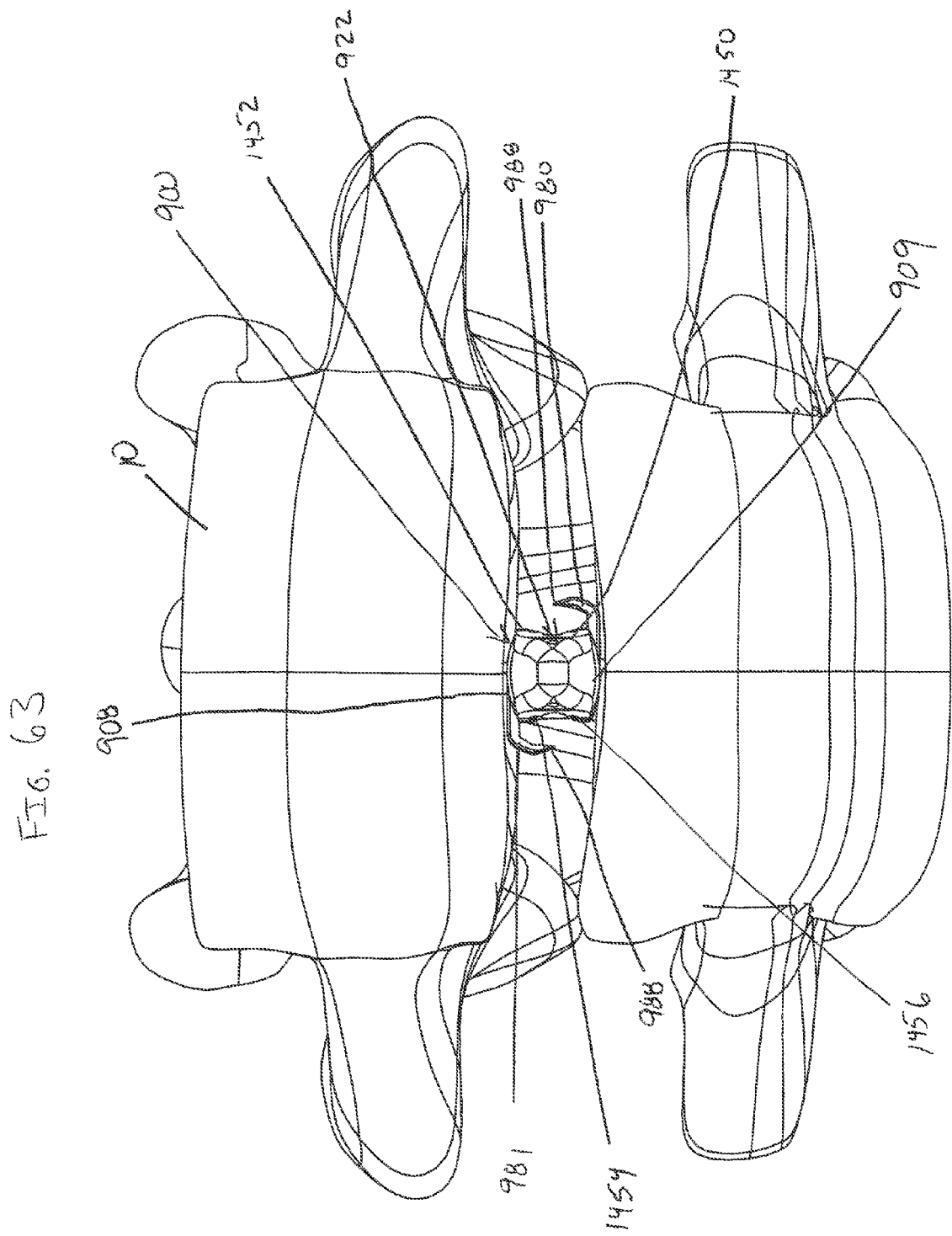
FIG. 63 is a front end elevational view of the implant device of FIG. 44 showing the implant device in an insertion orientation between adjacent vertebral bodies.

As shown in FIGS. 44-48, the implant device 902 includes a tapered leading end surface 904 for initially being inserted between adjacent vertebral bodies. A trailing end opposite the leading end surface 904 includes a tool engagement portion or opposite side slots 916 for being engaged by an engagement end portion 1416 of a tool 1414 for inserting the implant body 902 between adjacent vertebrae in an insertion orientation, as shown in FIG. 63, and rotating the implant body 902 between the adjacent vertebrae to a secured orientation as shown in FIG. 66. A longitudinal axis 943 of the implant body 902 extends between and through the leading end surface 904 and trailing end 906.

Figure 47:
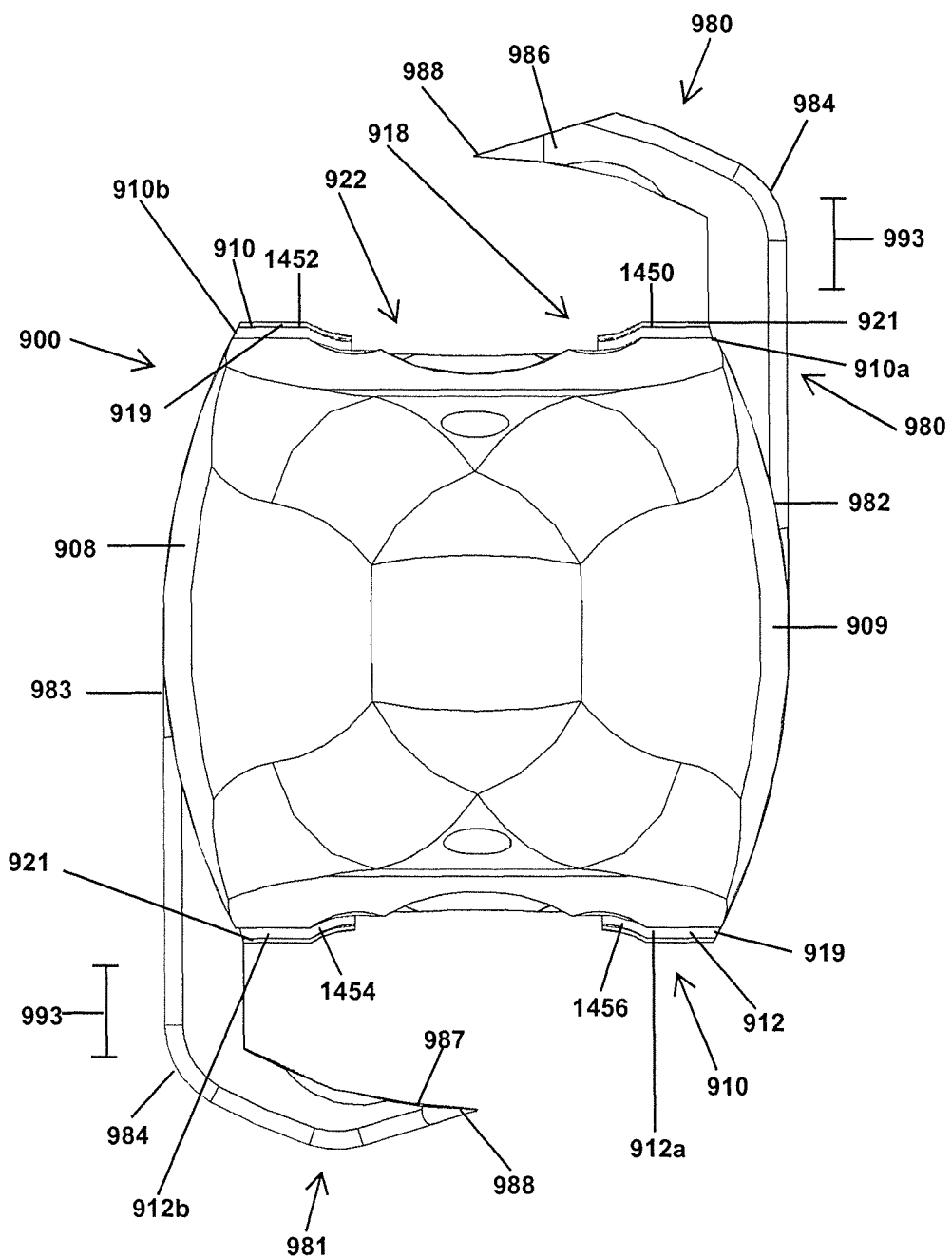
FIG. 47 is a front end elevational view of the implant device of FIG. 44 showing base portions of the anchoring members extending from one sidewall surface of the implant body and a bone penetrating portion extending toward an opposite sidewall surface of the implant body.
Figure 48:
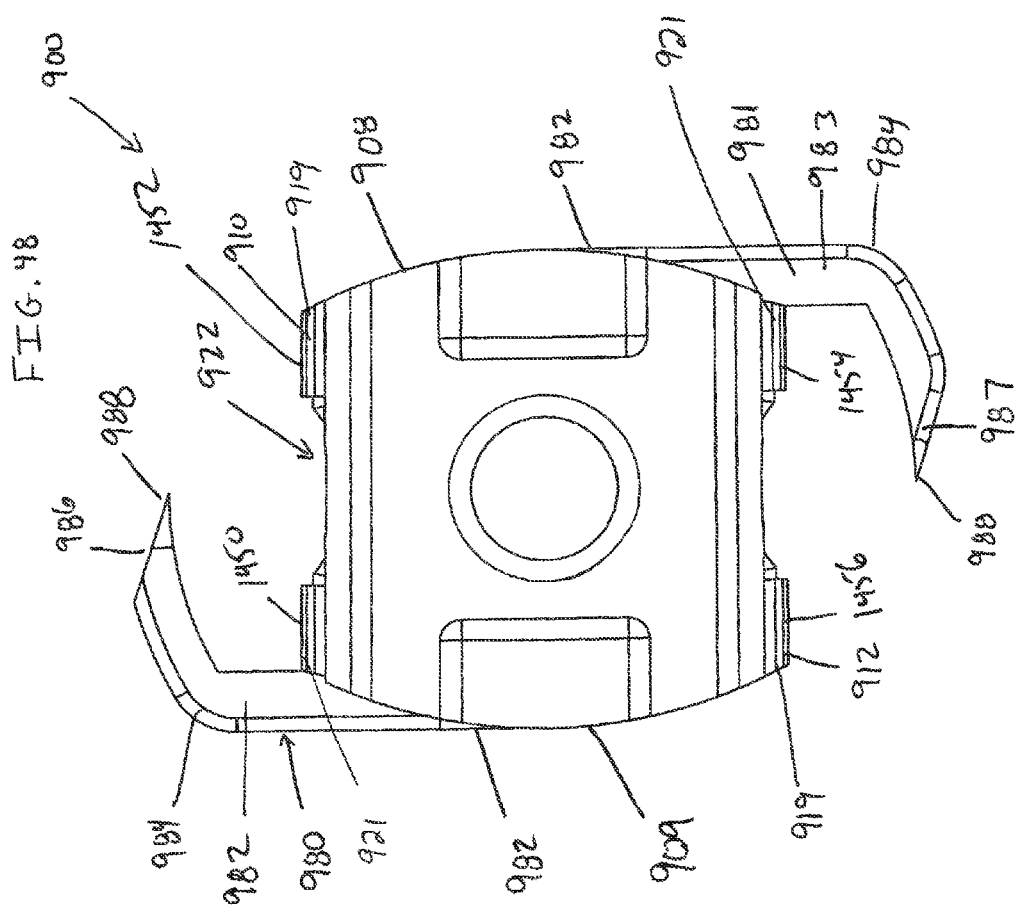
FIG. 48 is a back end elevational view of the implant device of FIG. 44.

Smooth, outwardly facing sidewall surfaces 908 and 909 extend between the leading surface 904 and the trailing end 906 and each include portions raised on either side of the respective tool engagement slots 916. The sidewall surfaces 908 and 909 provide low friction engagement with the vertebral bodies 10 with the implant body 902 in the insertion orientation so that the implant body 902 can be slid to a predetermined location. The sidewall surfaces 908 and 909 are spaced from one another a distance R to define the width of the implant device 902. The distance R is selected so that the implant body 902 can be slid between the vertebral bodies 10 in the insertion orientation and has sufficient structural strength to maintain separation of the vertebral bodies 10 in the secured orientation. As shown in FIGS. 47 and 48 the sidewall surfaces 908 and 909 are convex to aid in rotating the implant device 900 between the adjacent vertebral bodies 10 to the secured orientation.

Figure 44:
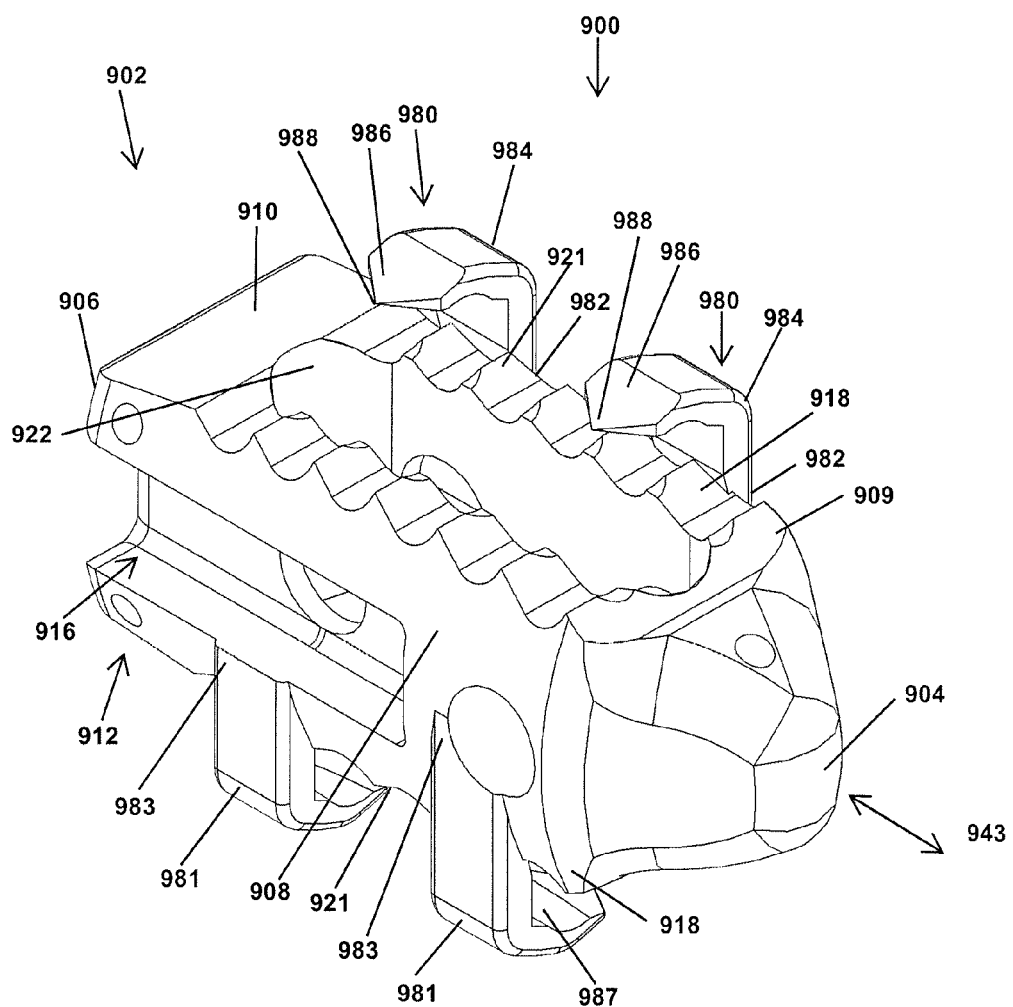
FIG. 44 is a perspective view of an implant device in accordance with another aspect of the invention showing teeth on an implant body of the implant device and anchoring members projecting from the implant body beyond the teeth.
Figure 45:
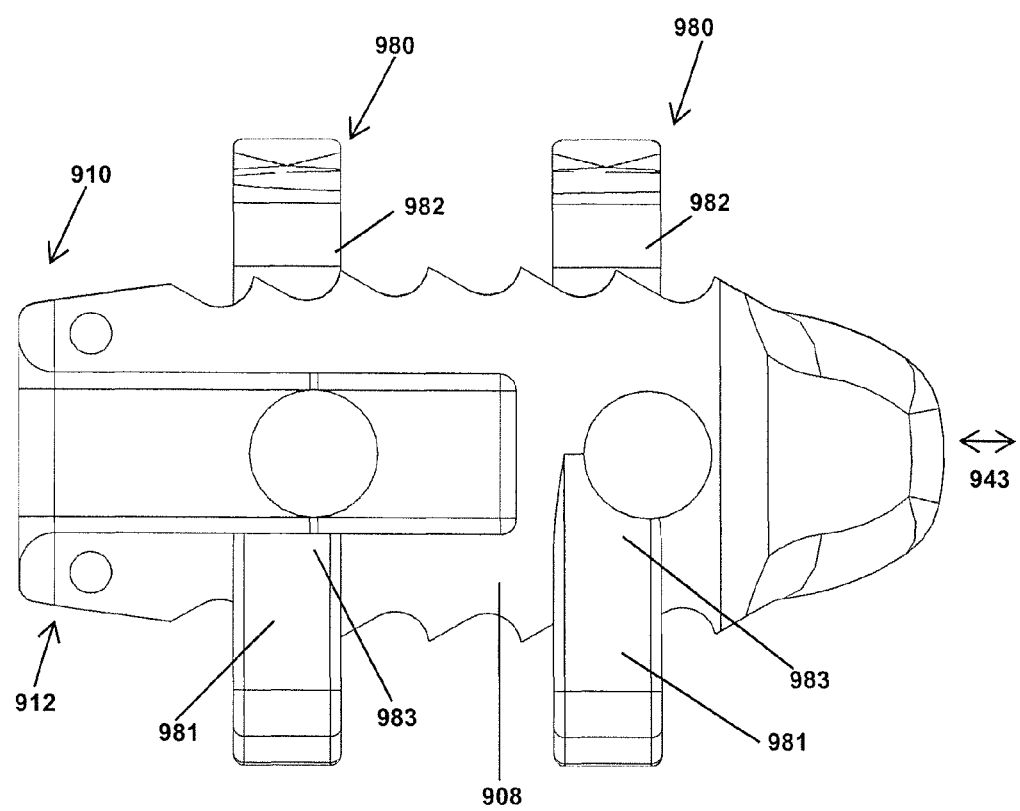
FIG. 45 is a side elevational view of the implant device of FIG. 44.
Figure 46:
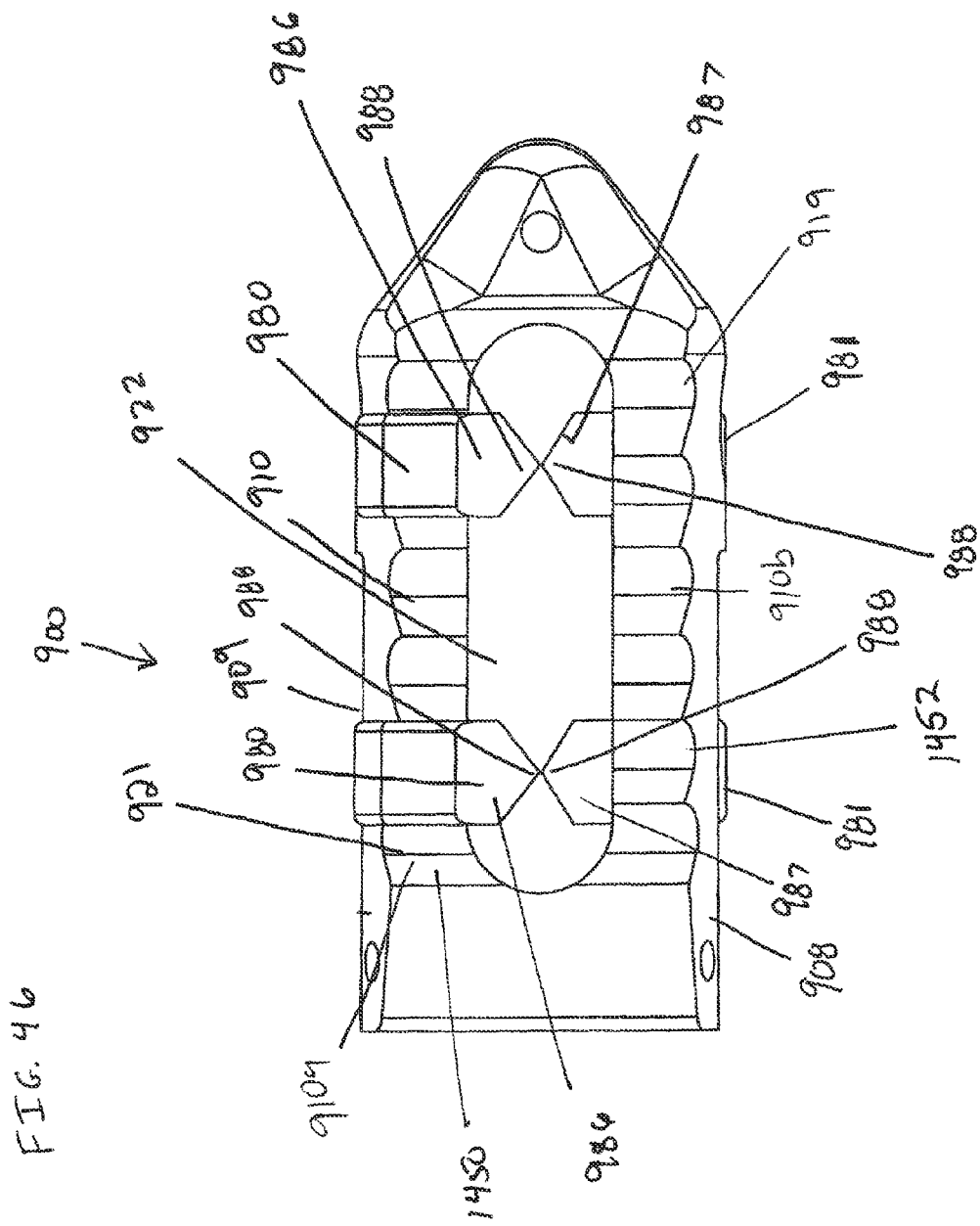
FIG. 46 is a top view of the implant device of FIG. 44 showing bone penetrating portions of the anchoring members extending across a portion of a central cavity of the implant body.

Upper and lower surfaces 910 and 912 of the implant body 902 extend between the sidewall surfaces 908 and 909, and the leading end surface 904 and the trailing end 906. As shown in FIG. 44, the implant body 902 can include a central cavity 922 extending between the upper and lower surfaces 910 and 912 for receiving bone growth material therein; however it is contemplated that the implant body 902 can be a solid member without a central cavity 922.

As shown in FIGS. 44-48, the upper and lower surfaces 910 and 912 each include portions 910a and 910b and 912a and 912b on either side of the cavity 922. The upper and lower surfaces 910a, 910b and 912a, 912b are configured to engage the vertebral bodies 10 with the implant device 900 rotated to the securing orientation. Gripping members 918, such as teeth, are formed on the upper and lower surfaces 910 and 912 and provide frictional engagement with the vertebral bodies 10 to resist movement of the implant device 10 relative to the vertebral bodies 10 with the implant device 900 in the securing orientation.

The gripping portions 918 of the implant body 902 includes spaced first and second sets of aligned teeth 1450 and 1452 of the upper surface 910a and 910b and spaced first and second sets of aligned teeth 1454 and 1456 of the lower surface 912a and 912b. As shown on FIGS. 47 and 48, the spaced sets of teeth 1450 and 1452 of the upper surface 910a, 910b and the spaced sets of teeth 1454 and 1456 of the lower surface 912a, 912b are separated by the central cavity 922.

As shown in FIGS. 44-48, the implant device 900 includes anchoring members 980 and 981 connected to the implant body 902. In particular, as best seen in FIGS. 47 and 48, the anchoring members 980 and 981 include base portions 982 and 983 connected to the implant body 902 and extending beyond the teeth 918 generally orthogonal to the longitudinal axis 943 of the implant body 902. In particular, the base portions 982 of anchoring members 980 extend upwardly beyond the upper surface 910 and are connected adjacent the first set of teeth 1450, and as shown in FIGS. 47 and 48, extend from sidewall surface 908. Similarly, the base portions 983 of anchoring members 981 extend downwardly beyond the lower surface 912 and are connected adjacent the set of teeth 1454 and extend from sidewall surface 909.

The anchoring members 980 and 981 further each include a bone penetrating portion 986 and 987 extending transversely from the base portions 982 and 983. As shown in FIGS. 47 and 48, the transition from the base portions 982 and 983 to the bone penetrating portions 986 and 987 includes a curved configuration 984. The bone penetrating portions 986 and 987 include a tapered distal end portion 988 having a sharp or pointed tip end for penetrating the vertebral body 10 as the implant device 900 is rotated. Optionally, the bone penetrating portions 980 and 981 can include anti-back-out mechanisms, such as a barb or hook to resist movement of the bone penetrating portions 980 and 981 out from within the penetrated vertebral bodies 10.

The bone penetrating portions 986 and 987 are sized to extend across the implant body toward the sidewall surface 908 and 909 opposite the sidewall surface 908 or 909 to which the base portion 982 and 983 are attached. The bone penetrating portions, in particular, are sized to not extend to the opposite sidewall surface 908 and 909. As shown in FIGS. 47 and 48, the bone penetrating portions 986 and 987 extend beyond the teeth 1450 and 1454 adjacent the base portions 982 and 983 and to a point over the cavity 922, the bone penetrating portions 982 and 983 do not extend to the second sets of teeth 1452 and 1456 opposite the first sets of teeth 1450 and 1454. While it is contemplated that the bone penetrating portions 986 and 987 could extend to the second sets of teeth 1452 and 1456, the bone penetrating portions 986 and 987 do not extend to the sidewall surface 908 and 909 adjacent the second sets of teeth 1452 and 1456.

Figure 64:
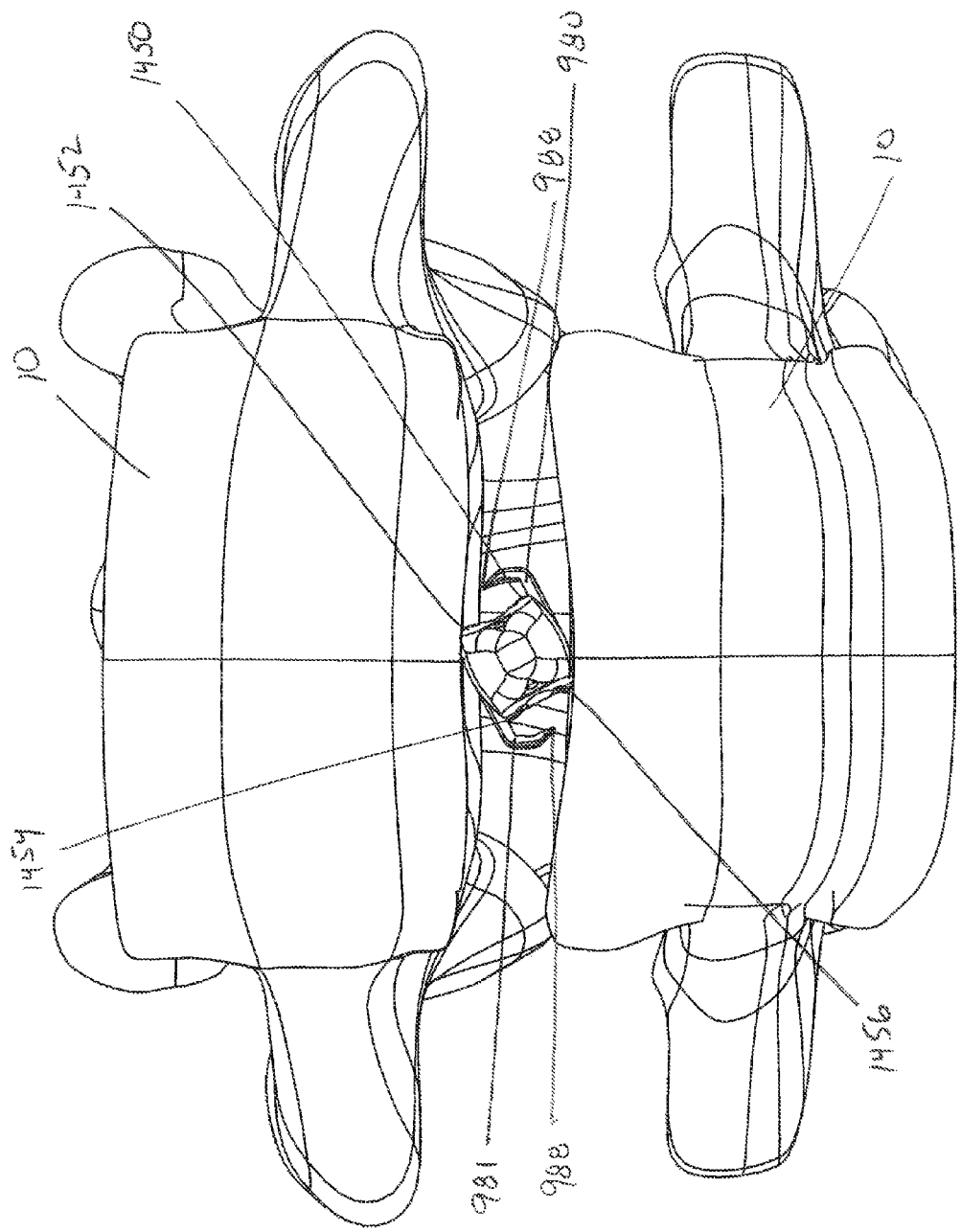
FIG. 64 is a front end elevational view of the implant device of FIG. 44 showing the implant device rotated so that the teeth of the implant body engage surfaces of the adjacent vertebral bodies.
Figure 65:
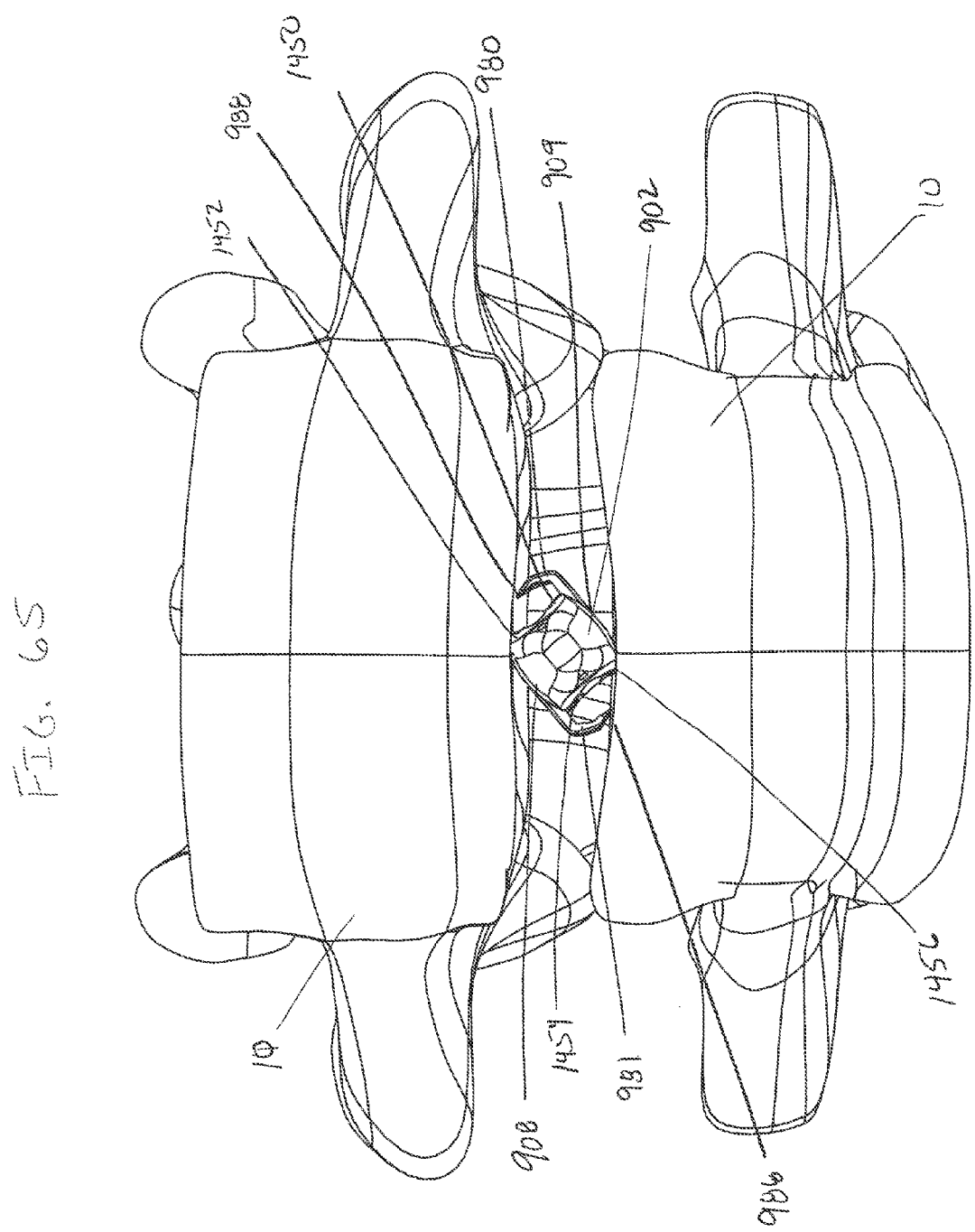
FIG. 65 is a front end elevational view of the implant device of FIG. 44 showing the implant device rotated so that the teeth and bone penetrating portions of the anchoring members engage the surfaces of the adjacent vertebral bodies.

As indicated above and as shown in FIG. 63, the implant device 900 is inserted between adjacent vertebral bodies 10 with the sidewall surfaces 908 and 909 engaging the vertebral bodies 10. Once the implant device is in the desired location, the implant device 900 can be rotated by the tool 1414 about the longitudinal axis 943 of the implant body 902. As the implant device 900 is rotated the second sets of teeth 1452 and 1456 of the upper and lower surfaces 910 and 912 engage the vertebral bodies to provide frictional engagement therewith so that the implant device 900 maintains the desired position, as shown in FIG. 64. The implant device 900 is further rotated, with the second sets of teeth 1452 and 1456 acting to maintain the general position of the implant device 900, as the bone penetrating ends 986 and 987 penetrate the vertebral bodies 10, as shown in FIG. 65. More particularly, the second sets of teeth 1452 and 1456 bit into the endplate surface while the bone penetrating members 986 and 987 of the anchor members 980 and 981 penetrate the vertebral bodies. The teeth 1452 and 1456 provide the frictional engagement and purchase for the higher torque required on the tool to drive the anchoring members 980 and 981 to penetrate the vertebral bodies 10. The implant device 900 continues to rotate until the first set of teeth 1450 and 1454 adjacent the base portions 982 and 983 of the anchoring members 980 and 981 engage the vertebral bodies, as shown in FIG. 66.

The base portions 982 and 983 are configured to extend a distance 993 from the respective upper and lower surfaces 908 and 910 to allow a sufficient amount of the vertebral body 10 to be positioned between the upper and lower surfaces 908 and 910 and bone penetrating members 986 and 987 of the anchoring member 980 and 981 to maintain structural integrity and strength of the bone therebetween. Further, the base portions 982 and 983 are sized so that, with the implant body 902 in the insertion orientation, the anchor members 980 and 981 do not over hang the edges of the vertebral bodies 10 or otherwise obstruct insertion between the vertebral bodies 10.

Figure 62:
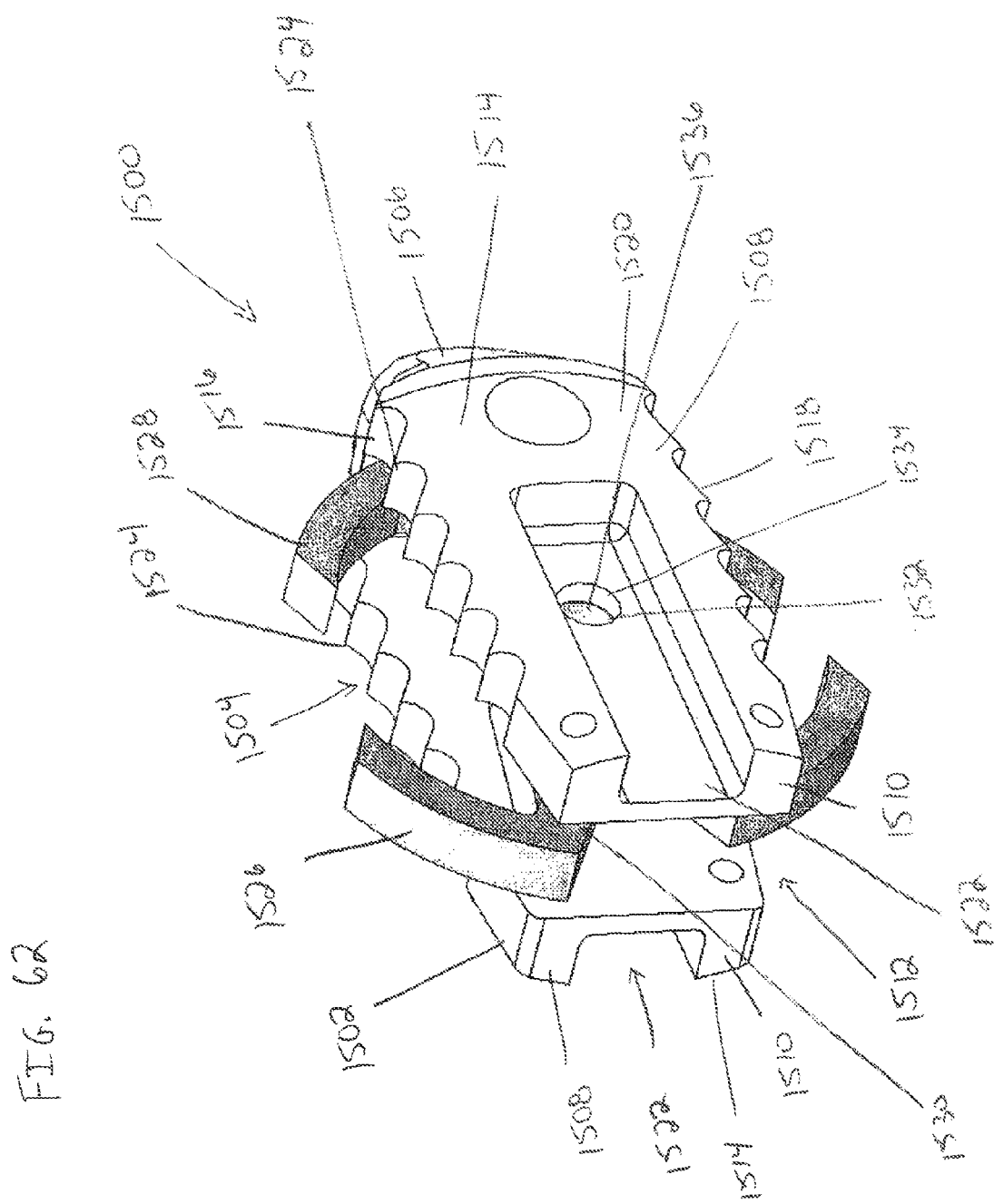
FIG. 62 is a perspective view of an implant device in accordance with another aspect of the invention showing teeth on a body of the implant device with scissor arms extending beyond upper and lower surfaces of the implant body in a securing orientation.

Referring to FIG. 62, an alternative implant device 1500 is shown. The following description will focus on the differences between the implant device 1500 and the implant devices 600 and 1200.

Similar to implant device 1200, the implant device 1500 includes an implant body 1502 having an outer wall 1504. The outer wall includes a leading edge wall 1506 for being initially inserted between adjacent vertebrae. As shown in FIG. 62, the leading edge wall 1506 includes a tapered configuration, similar to implant device 600. Sidewalls 1508 extend from the leading edge wall 1506 and include adjacent distal ends 1510. The outer wall includes a gap 1512 therein between the distal ends 1510 of the sidewalls 1508.

Similar to implant device 600, outwardly facing surfaces 1514 of the sidewalls 1508 have a smooth configuration to provide low friction engagement with the vertebral bodies as the implant body 1502 is inserted therebetween. Once in place, the implant body 1502 can be rotated so that upper and lower surfaces 1516 and 1518 of the implant body 1502 engage the vertebral bodies. To aid in rotation, the sidewalls 1508 can have a convex configuration 1520 and include a tool engagement portion 1522 at the distal ends 1510 thereof to be engaged by an engagement end portion 1416 of a tool 1414.

The upper and lower surfaces 1516 and 1518, as shown in FIG. 62, include gripping portions 1524, such as teeth, formed thereon for providing frictional engagement with the vertebral bodies and resisting movement of the implant body 1502 relative to the vertebral bodies 10.

To further secure the implant body 1502 in place, the implant device 1500 includes scissor arms 1526 and 1528 pivotably connected thereto, similar to implant device 1200. The scissor aims 1526 and 1528 include elongate base arm portions 1530 having an aperture 1532 therein. The sidewalls 1508 include corresponding apertures 1534 sized to receive a pivot pin 1536 therebetween. The apertures 1532 of the base are portions 1530 are sized to pivotably receive the pivot pin 1536 therethrough so that the scissor arms 1526 and 1528 can pivot from an insertion orientation to a secured orientation, similar to implant device 1200.

Generally, as shown in FIG. 62, the scissor arms 1526 and 1528 are similar to and operate the same as the scissor arms 1218 and 1318 of implant device 1200 and 1300.

An alternative implant device 1100 is shown in FIGS. 34-38B. As shown, the implant device 1100 can be used as an anchor for any other type of device requiring a static structure to be mounted on. For example, it is contemplated that the implant shown in FIG. 34 be used as a blocker to prevent an implant, such as an artificial nucleus implant from escaping from a predetermined position between the vertebrae. Alternatively, the implant device 1100 can be used to plug an opening in an annulus between the vertebral bodies 10. In this embodiment, the blocker is acting as an anchor for the implantation of any other type of artificial nucleus (not shown).

In the blocker embodiment shown in FIG. 35, the implant body 1102 acts as a blocking structure while the mechanically deployable rotatable anchoring members or projections 1180, in the form of hooks, are used to statically secure the implant device 1100 within bone. The device for securing an implant to bone can be seen with the mechanically deployable projections 1180 deployed in FIGS. 34, 35, 36A, 37A and 38A and with the mechanically deployable projections retracted in FIGS. 36, 37 and 38. The implant device 1100 can includes gripping surfaces along one or both of the upper and lower surfaces 1110 and 1112 to grip the bone and resist movement of migration of the implant device 1100. Alternatively, as shown in FIGS. 34-38, the implant device 1100 can include a smooth, continuous upper surface 1110 to minimize friction between the upper surface 1110 and adjacent vertebral body 10.

The projections 1180 curve so that they are generally completely received within a recess 1103 extending into the lower surface 1112 of the body 1102 in the insertion orientation. The projections 1180 are connected to a rotatable shaft 1120 which is pivotably connected to the implant body 1102. The shaft 1120 includes a head portion 1124 having a tool engagement portion 1126 for being engaged by a tool. As the tool engagement portion 1126 is engaged and rotated by a tool, the shaft 1120 and projections 1180 rotate so that distal ends 1128 of the rotatable projections 1180 extend out from within the recess 1103 and engage and penetrate the bone in a securing orientation. Locking mechanisms (not shown), such as described above, can be used to resist migration of the rotatable portions 1180 from within the bone.

Preferably, the projections 1180 include an arcuate portion 1181 having a substantially constant radius of curvature. The radius of curvature is configured to correspond to an arc of the circular path traveled by the arcuate portion 1181 as the anchoring member 1180 is pivoted.

The implant devices of the present invention may be fabricated from any suitable materials having desirable strength and biocompatibility. Suitable materials may include, for example, biocompatible metals and related alloys (such as titanium and stainless steel), shape memory metals (such as Nitinol), biocompatible polymers (including, for example, materials of the polyaryletherketone family such as PEEK (polyetheretherketone), PAEK (polyaryletherketone), PEK (polyetherketone), PEKK (polyetherketoneketone), PEKEKK (polyetherketoneetherketoneketone), PEEKK (polyetheretherketoneketone), and PAEEK (polyaryletheretherketone), filled materials such as carbon or glass fiber-reinforced materials), bone substitute materials (such as hydroxyapatite and tricalcium phosphate), composite materials, and/or any combination of the above.

In one preferred form, the implant devices are formed of a PEEK-type material. In another from, the implant device may be formed, in whole or in part, or coated with a calcium phosphate ceramic bone substitute such as hydroxyapatite, tricalcium phosphate, and/or mixtures thereof. Particularly preferred hydroxyapatite and tricalcium phosphate compositions include those disclosed in, for example, U.S. Pat. No. 6,013,591, U.S. Pat. No. RE 39,196, and U.S. Patent Application Publication No. 2005/0031704, which are hereby incorporated in their entirety herein. Coating with the calcium phosphate ceramics can be achieved by any known method, including dip coating-sintering, immersion coating, electrophoretic deposition, hot isostatic pressing, solution deposition, ion-beam sputter coating and dynamic mixing, thermal spraying techniques such as plasma spraying, flame spraying and high-velocity oxy-fuel combustion spraying. In one preferred embodiment, hydroxyapetite coating is achieved by plasma spraying.

In yet another form, the implant device may be formed of a PEEK-type material and coated with such a bone substitute material. In yet another form, the implant device may be formed, in whole or in part, coated with, injected with, incorporate, and/or retain a bone growth stimulating composition such as the bioactive hydrogel matrix described, for example, in U.S. Pat. Nos. 6,231,881, 6,730,315, 6,315,994, 6,713,079, 6,261,587, 5,824,331, 6,068,974, 6,352,707, 6,270,977, 5,614,205, 6,790,455, 5,922,339, and U.S. Patent Application Publication No. 2005/0118230, which are hereby incorporated in their entirety herein.

Alternatively, the implant device of the invention may be formed of two distinct materials. In particular, the implant body may be formed of a first material, such as PEEK or carbon fiber PEEK, and the piercing portions may be made of a metal, such as Ti64. In one example, the piercing portions of implant device 600, 700, and 800 and 900 may be formed of a metal. Additionally, the part or the entire rotatable portion of the implant devices 100, 200, 300, 400, 500, 1100, 1200, 1300 and 1500 may be formed of a material distinct from the material used to form the implant body.

The central cavities 122, 222, 322, 422, 522, 622, 722, 822, 922, 1204 and 1304 provide a region for receiving bone growth material therein. In one embodiment, the implant device 100, 200, 300, 400, 500, 600, 700, 800, 900, 1100, 1200 and 1300 is packed with bone growth filler prior to implantation. In a preferred embodiment, the implant device 100, 200, 300, 400, 500, 600, 700, 800, 900, 1100, 1200 and 1300 can be implanted in the vertebral space and then packed with bone growth filler. Preferably, the bone growth material is inserted through the insertion tool engagement portion 416. In an alternative preferred embodiment, a bioresorbable sponge fixated to the implant device is used to secure the bone growth stimulating composition.

The bone void filler or graft material is preferably a combination of one or more various substances consisting of bone matrix, bone void filler, bone graft extender, biopolymers that stimulate bone growth, bone growth stimulating orthobiologic products, bioactive hydrogel matrix comprising a polypeptide and a long chain carbohydrate, and osteoinductive or osteoconductive materials, medicaments, stem or progenitor cells, and three-dimensional structural frameworks. In some embodiments, the bone matter may be a composition made from de-mineralized bone matrix.

In one embodiment, the bone growth stimulating composition comprises a bioactive hydrogel matrix comprising a polypeptide, such as gelatin, and a long chain carbohydrate, such as dextran, such as described in U.S. Pat. No. 6,231,881 to Usala et al. and U.S. Patent Application Publication No. 2005/0118230 to Hill et al., which are incorporated by reference in their entirety herein. In an alternative embodiment, this bone growth stimulating composition can be integrated with hydroxyapetite or other bone substitutes to provide sustained delivery of the bone growth stimulating compositions.

In one embodiment, the bone void fillers include a moldable putty optimized for implantation which provide significantly greater set time than most bone void fillers, such as one or both of TrioMatrix™ and FortrOss™. The increased set time allows the bone void filler, in the form of moldable putty optimized for implantation, to be extruded into the central cavity as the bone void filler remains "moldable" for a sufficient length of time. Furthermore, TrioMatrix™ and FortrOss™ have superior biological performance for inducing bone growth making them ideal as bone void fillers.

The bone void filler, such as TrioMatrix™, is preferably made from synthetically made hydroxyapatite, synthetically made gelatin carrier, demineralized bone matrix, and the patient's own blood products and/or bone marrow extract. In another form, the bone void filler, such as FortrOss™, is made from the mixing of synthetically made hydroxyapatite, synthetically made gelatin carrier, and the patient's own blood products and/or bone marrow extract.

The implant devices can readily be filled with such a moldable bone void filling putty. Moreover, biologic materials may be introduced to this admixture by the surgeon in the operating room, such as bone morphogenetic proteins (BMP) or bone growth stimulating compositions, to further induce bone growth. In yet another embodiment, bone chips from the patient can be added to the bone void filler.

Preferably, the bone void filler composition, such as FortrOss™, is made of synthetic and autograph materials to eliminate the risk of infection from bone donors and reduce the risk of rejection of the bone filler by the patient's immune system. Autograft materials are tissue that is transplanted from one portion of the patient's body to another. In the instant invention, bio-compatible autograft materials from the patient's own body in the form of blood products or bone chips with synthetic extenders of the autograft material are to be placed in the central cavity that encourage bone growth within and around the device.

Hydroxyapatite (HA) and tricalcium phosphate (TCP) can be used in the bone void filler for facilitating bone fusion. These compositions facilitate fusion by having the characteristic of being "bioactive" which indicates the ability to facilitate a cellular or tissue response, such as, induction of vasculogenesis, promotion of cellular attachment to a scaffold material, and promotion of tissue regeneration.

Figure 33:
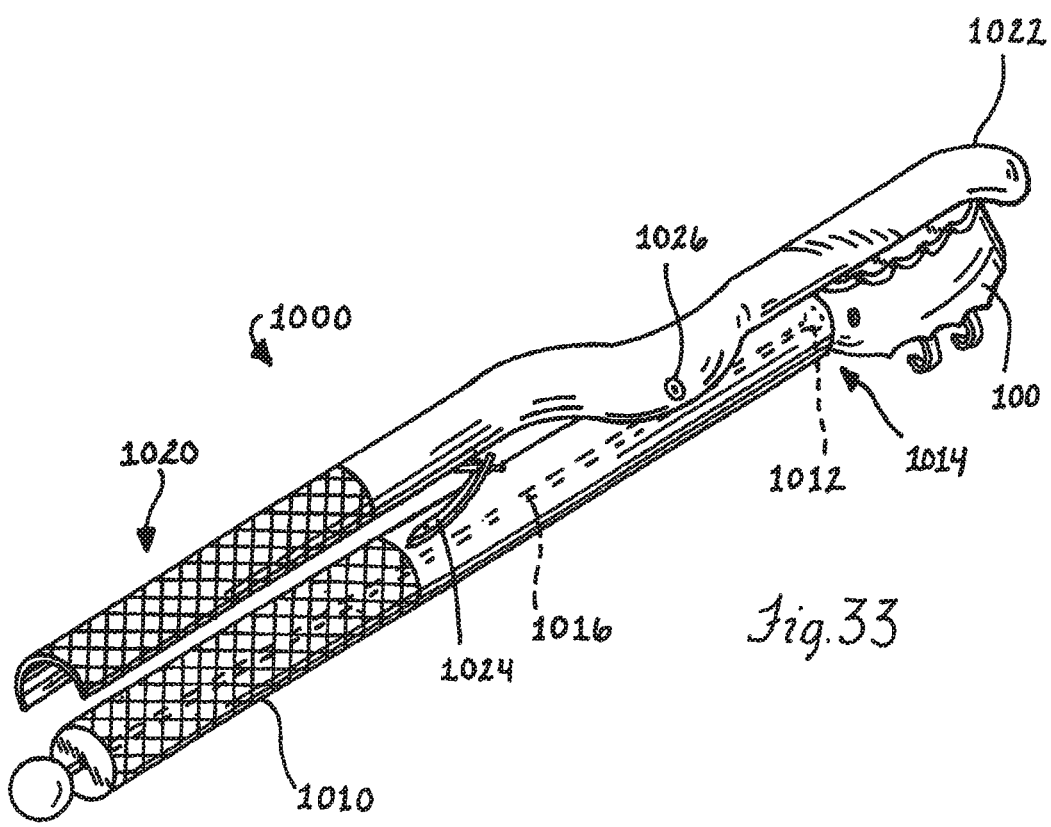
FIG. 33 is a perspective view of the insertion tool.
Figure 37A:
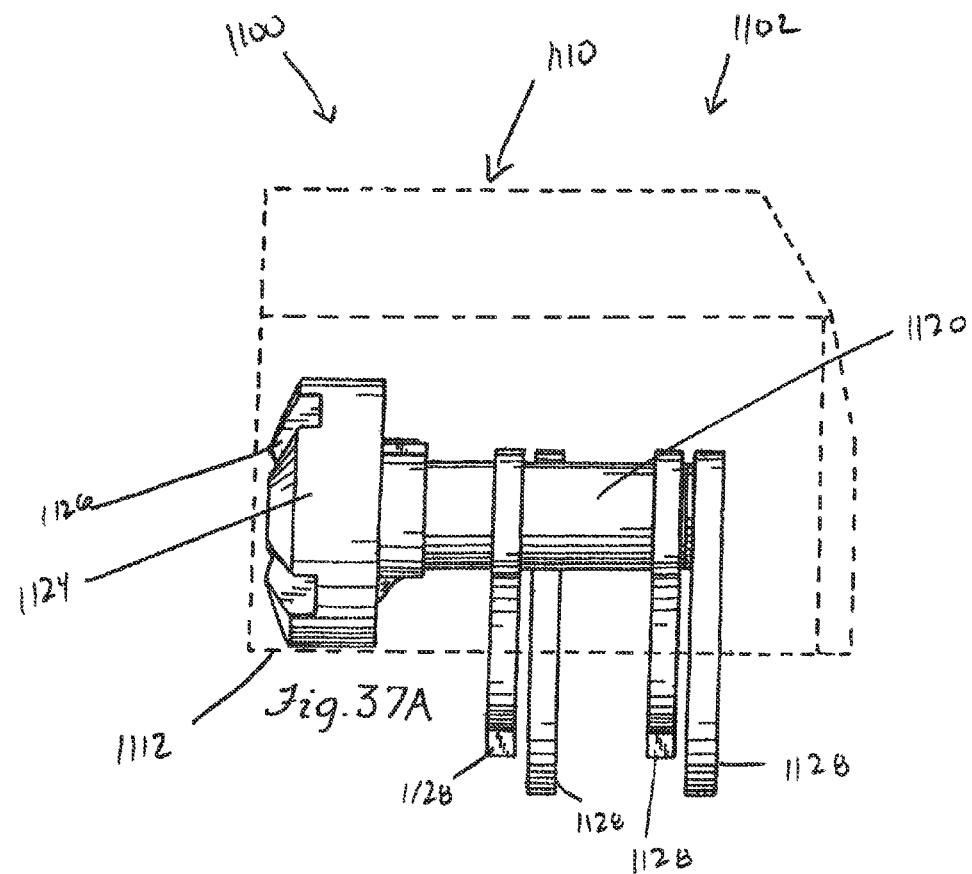
FIG. 37A is a side view of the implant device of FIG. 34 in the securing configuration showing the implant body in phantom.
Figure 37:
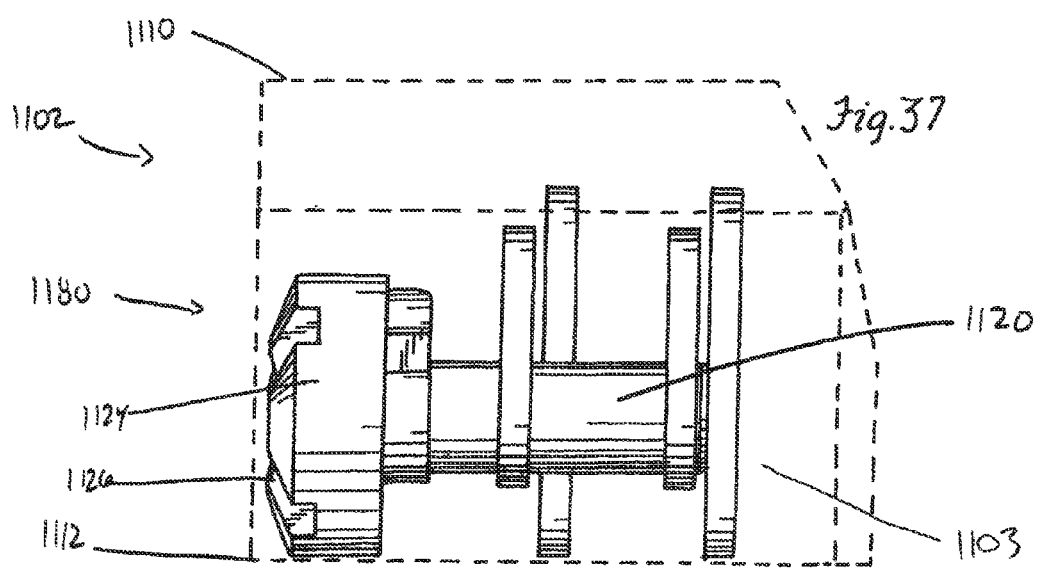
FIG. 37 is a side view of the implant device of FIG. 34 in the insertion configuration showing the implant body in phantom.
Figure 38:
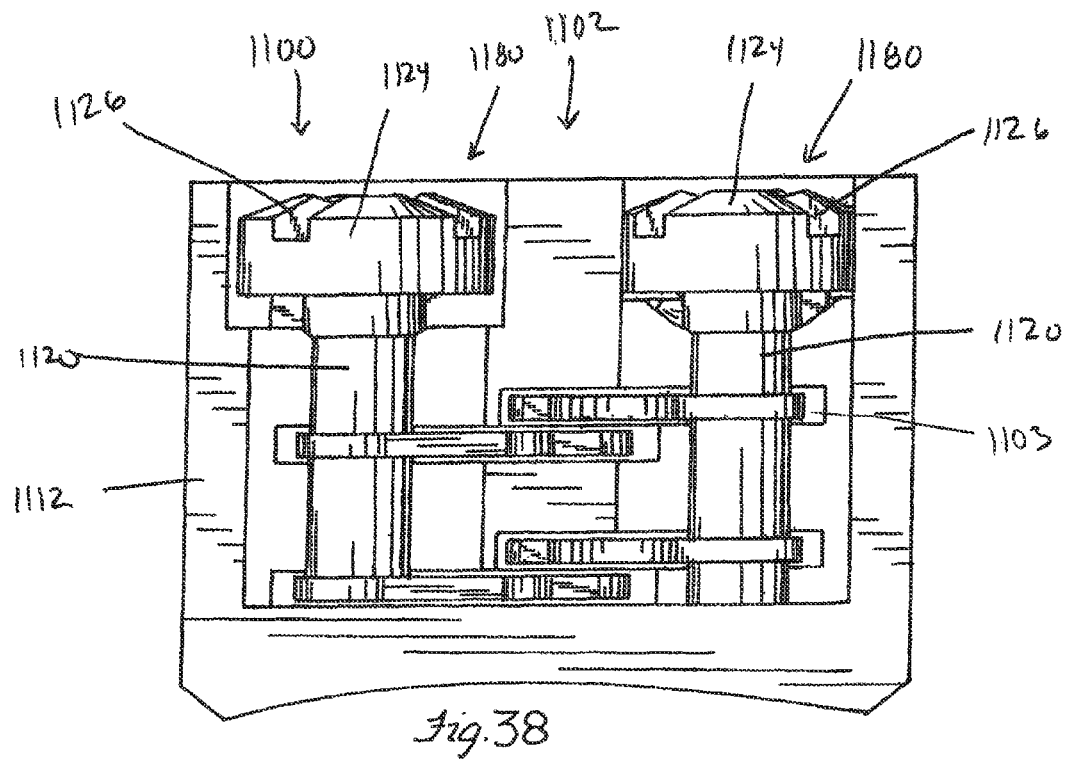
FIG. 38 is a bottom view of the implant device of FIG. 34 in the insertion configuration.
Figure 38A:
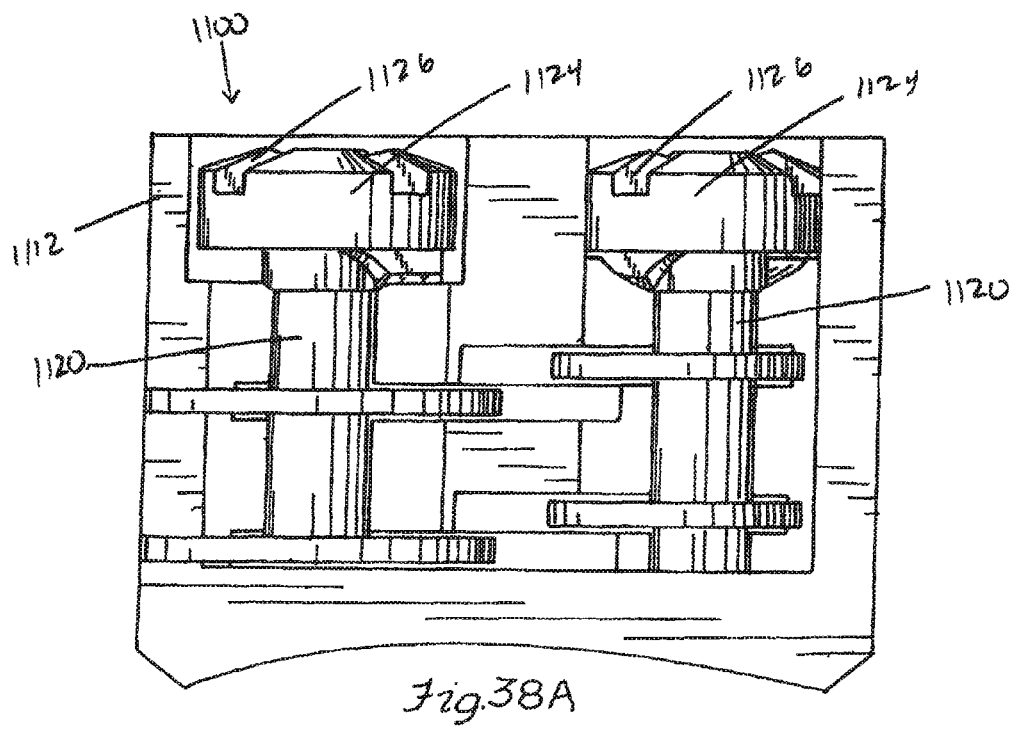
FIG. 38A is a bottom view of the implant device of FIG. 34 in the securing configuration.
Figure 40:
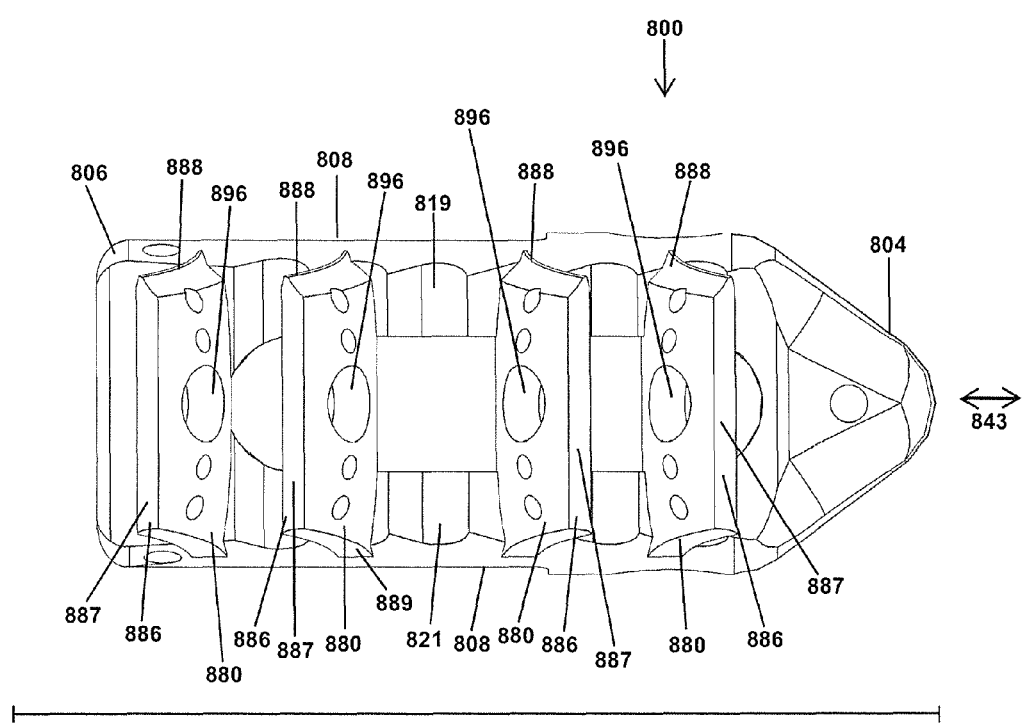
FIG. 40 is a top view of the implant device of FIG. 39 showing the cutting fins extending across a central cavity of the implant body.
Figure 41:
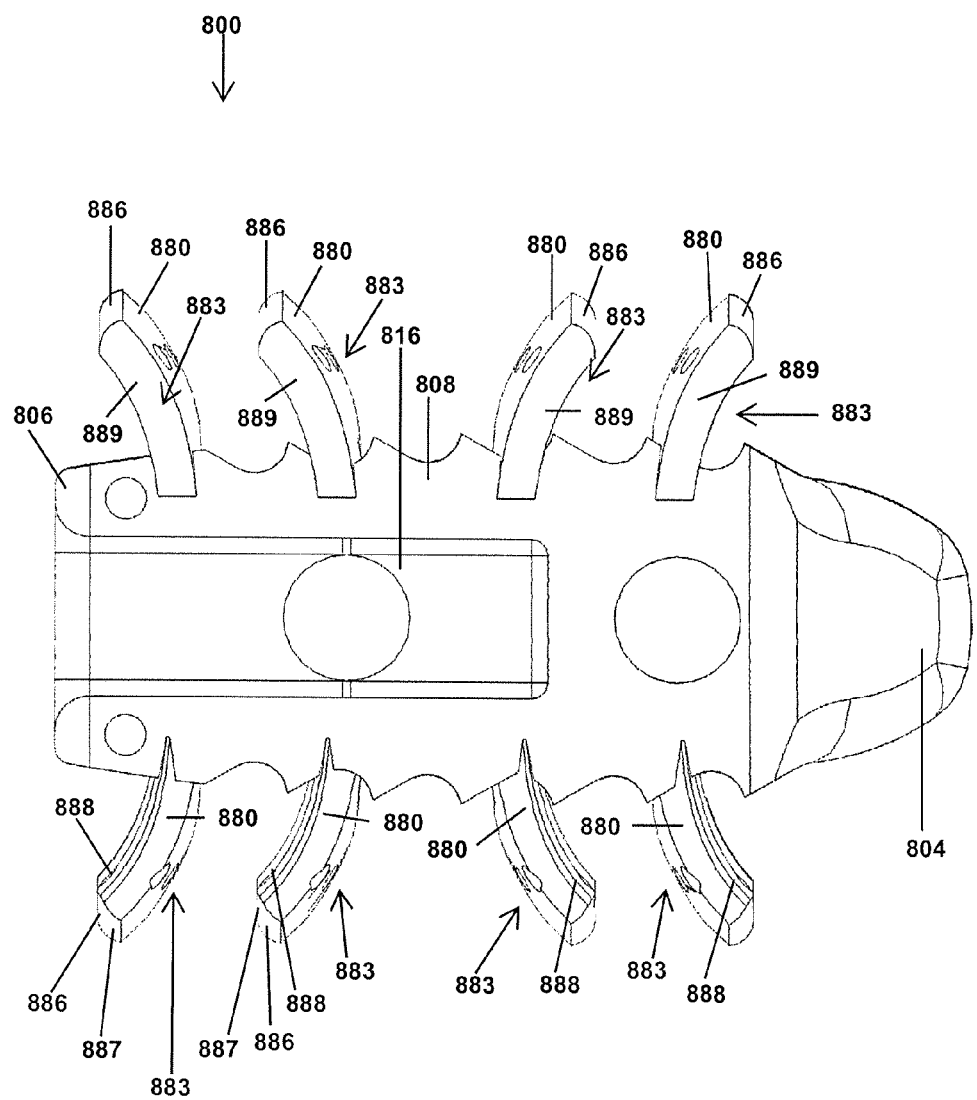
FIG. 41 is a side elevational view of the implant device of FIG. 39 showing the curvature of the cutting fins of the implant device.

The previously described devices for securing an implant to bone will need to be implanted into the human body. An exemplary tool 1414, as shown in FIG. 49, includes an engagement end portion 1416 for engaging an implant device. A preferred embodiment of a tool apparatus 1000 for implanting a device for securing an implant to bone is shown in FIG. 33. The apparatus 1000 for implanting the device has a cannulated main shaft 1010 with a mechanism 1012 located on the distal end 1014 for attaching an implantable device. The distal end 1014 of the main shaft 1010 attaches to the device for securing an implant to bone to allow for minimally invasive surgery from various approaches through the patients body.

The main shaft 1010 has a rotatable rod 1016 located with the main shaft 1010 capable of longitudinal motion within the main shaft 1010. The rotatable rod 1016 allows the piercing portions to be locked into place. The longitudinal motion of the rod 1016 allows for disengagement of the apparatus 1000 from the device.

In addition, an arm 1020 with a counter-force plate 1022 located on the distal end 1014 for securing an implant on the main shaft 1010 is provided as shown in FIG. 33. The counter-force plate 1022 maintains attachment of the device during the insertion of the device into the patient. The plate 1022 is disengaged by compressing a spring 1024 located between the main shaft 1010 and the arm 1020. The main shaft 1010 and the arm 1020 are connected by a pin 1026 that allows the arm 1020 to hinge on the main shaft 1010.

The complete method for operating the device for securing an implant to bone begins with making a surgical incision, distracting the tissue in place, and removing the severely damage tissue. The device is then inserted and positioned in the patient. The rotatable portion is then rotated, along with the piercing portions, so that the piercing portions penetrate the adjacent vertebral bodies. The patient is then closed and the procedure is complete. The bone growth stimulating compounds, the other bone substitutes material, and the patients own body then heals the remaining wounds and causes the implanted device and adjacent bone to fuse into a solid structure to support the patient's body weight.

Those skilled in the art will recognize that a wide variety of modifications, alterations, and combinations can be made with respect to the above described embodiments without departing from the spirit and scope of the invention, and that such modifications, alterations, and combinations, are to be viewed as being within the scope of the invention.

What is claimed is:

1. A spinal implant for being secured between adjacent vertebrae, the spinal implant comprising:
   an implant body configured for insertion between adjacent vertebral bodies, the implant body including an upper surface, a lower surface and a cavity between the upper and lower surfaces;
   a rotatable portion including a wall having a first top surface, a second bottom surface and substantially parallel side surfaces therebetween, the rotatable portion being configured for rotation between an insertion orientation and an implanted orientation; and
   a bone piercing portion of the rotatable portion attached to and extending from one of the side surfaces of the wall and having a leading distal end such that in the insertion orientation the leading distal end is disposed in the cavity and when the rotatable portion is rotated to the implanted orientation, the leading distal end is shifted out of the cavity beyond one of the upper and lower surfaces for penetrating the surface of one of the vertebral bodies.

2. The spinal implant of claim 1 wherein the bone piercing portion includes an arcuate inner surface and an arcuate outer surface such that the bone piercing portion is generally hook shaped.

3. The spinal implant of claim 1 wherein the bone piercing portion is coupled to the wall and extends above the first surface and the upper surface when the rotatable portion is in the implanted orientation.

4. The spinal implant of claim 1 further comprising implant body teeth extending along at least one of the upper and lower surfaces to engage one of the vertebrae.

5. The spinal implant of claim 4 further comprising gripping portions positioned on the first surface and extending in a substantially coplanar manner with the implant body teeth when the rotatable portion is in the implanted orientation.

6. The spinal implant of claim 1 further comprising a tool engaging portion configured to rotate the rotatable portion between the insertion orientation and the implanted orientation.

7. The spinal implant of claim 1 further comprising a securing portion configured to secure the rotatable portion to the implant body, the securing portion including a slotted portion having lower and upper portions with a slot therebetween configured to permit the lower and upper portions to be compressed towards one another as the slotted portion passes through a step in the implant body.

* * * * *